United States Patent
Vaaje-Kostad et al.

(10) Patent No.: US 10,273,512 B2
(45) Date of Patent: *Apr. 30, 2019

(54) METHODS OF DEGRADING OR HYDROLYZING A POLYSACCHARIDE

(71) Applicants: Novozymes A/S, Bagsvaerd (DK);
Novozymes, Inc., Davis, CA (US)

(72) Inventors: Gustav Vaaje-Kostad, Oslo (NO);
Bjorge Westereng, Oslo (NO); Vincent G. H. Eijsink, Oslo (NO); Svein J. Horn, Oslo (NO); Morten Sorliie, Oslo (NO); Zarah Forsberg, Oslo (NO)

(73) Assignees: Novozymes A/S, Bagsvaerd (DK);
Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/660,027

(22) Filed: Jul. 26, 2017

(65) Prior Publication Data

US 2018/0016606 A1    Jan. 18, 2018

Related U.S. Application Data

(62) Division of application No. 13/814,450, filed as application No. PCT/US2011/046838 on Aug. 5, 2011, now Pat. No. 9,758,802.

(30) Foreign Application Priority Data

Aug. 6, 2010   (GB) .................................. 1013317.1
Oct. 6, 2010   (GB) .................................. 1016858.1
Mar. 25, 2011  (GB) .................................. 1105062.2

(51) Int. Cl.
*C12P 19/00*  (2006.01)
*C12P 19/26*  (2006.01)
*C12P 7/10*   (2006.01)
*C12P 19/12*  (2006.01)
*C12P 19/02*  (2006.01)
*C12P 19/14*  (2006.01)

(52) U.S. Cl.
CPC .............. *C12P 19/00* (2013.01); *C12P 7/10* (2013.01); *C12P 19/02* (2013.01); *C12P 19/12* (2013.01); *C12P 19/14* (2013.01); *C12P 19/26* (2013.01); *Y02E 50/16* (2013.01)

(58) Field of Classification Search
CPC .. C12P 7/10; C12P 19/02; C12P 19/12; C12P 19/00; C12P 19/26; C12P 19/14; Y02E 50/16

See application file for complete search history.

(56) References Cited

U.S. PATENT DOCUMENTS

| | | |
|---|---|---|
| 4,540,664 A | 9/1985 | Johnson et al. |
| 7,271,244 B2 | 9/2007 | Dotson et al. |
| 7,361,495 B2 | 4/2008 | Brown et al. |
| 9,758,802 B2 * | 9/2017 | Vaaje-Kolstad .......... C12P 7/10 |
| 2008/0251374 A1 | 10/2008 | McManigal |
| 2010/0129860 A1 | 5/2010 | McFarland et al. |

OTHER PUBLICATIONS

Arantes et al, 2010, Biotechnol Biofuel 3(1,4), 1-11.
Gilbert et al, 2010, Plant Physiol 153(2), 444-455.
Harris et al, 2010, Biochem 49(15), 3305-3316.
Kolstad et al, 2010, Science (330), 219-222.
Himmel et al., 2007, Science 315: 804-807.
Reese et al., 1950, J Bacteriol. 59: 485-497.
Vaaje-Kolstad et al., 2005, J. Biol. Chem. 280: 28492-28497.
Boraston et al., 2004, Biochem. J. 382: 769-781.
Henrissat, 1991, Biochem. J. 280 (Pt 2): 309-316.
Moser et al., 2008, Biotechnol. Bioeng. 100(6): 1066-1077.
Karkehabadi et al., 2008, J. Mol. Biol. 383: 144-154.
Vaaje-Kolstad et al., 2005, J. Biol. Chem. 280: 11313-11319.
Miller et al, 2009, Appl Environ Microbiol 75(19), 6132-6141.
Broun et al, 1998, Science 282, 1315-1317.
Chica et al, 2005, Curr Op Biotechnol 16(4), 378-384.
Devos et al, 2000, Prot—Struc Func Gene 41, 98-107.
Suo et al, 2004, Proc Natl Acad Sci USA 101(25), 9205-9210.
Kisselev et al, 2002, Struc 10, 8-9.
Seffernick et al, 2001, J Bacteriol 183(8), 2405-2410.
Sen et al, 2007, Appl Biochem Biotechnol 143, 212-223.
Vuong et al, 2010, Biotechnol Bioeng 107(2), 195-205.
Whisstock et al, 2003, Qtr Rev Biophys 36(3), 307-340.
Witkowski et al, 1999, Biochem 38(36), 11643-11650.
Wymelenberg et al, 2010, Appl Environ Microbiol 76 (11), 3599-3610.
Martinez et al, PNAS 106(6), 1954-1959.
Chen, 2005, Chemical Industry Press 58-59.
Chen, 2008, Chemical Industry Press, 104.
Eijsink et al, 2008, Trends Biotechnol 26 (5), 228-235.

* cited by examiner

*Primary Examiner* — Ganapathirama Raghu
(74) *Attorney, Agent, or Firm* — Robert Starnes

(57) ABSTRACT

The invention provides a method of degrading or hydrolyzing a polysaccharide, preferably cellulose or chitin, comprising contacting said polysaccharide with one or more oxidohydrolytic enzymes, preferably a CBM33 family protein (preferably CBP21) or a GH61 family protein, wherein said degradation or hydrolysis is carried out in the presence of at least one reducing agent and at least one divalent metal ion. A method of producing an organic substance comprising said method is also provided.

10 Claims, 42 Drawing Sheets
Specification includes a Sequence Listing.

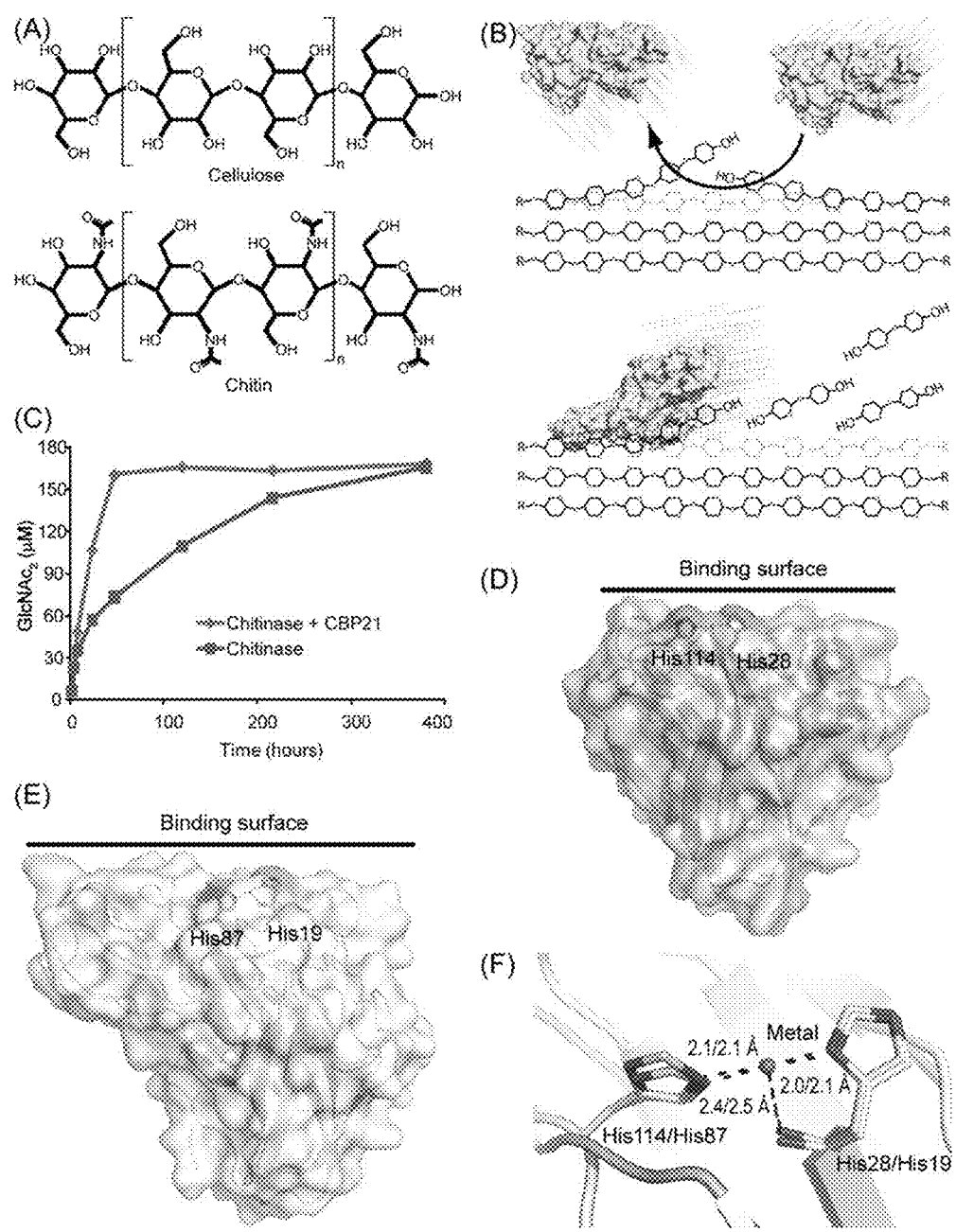
Figs. 1A, 1B, 1C, 1D, 1E, & 1F

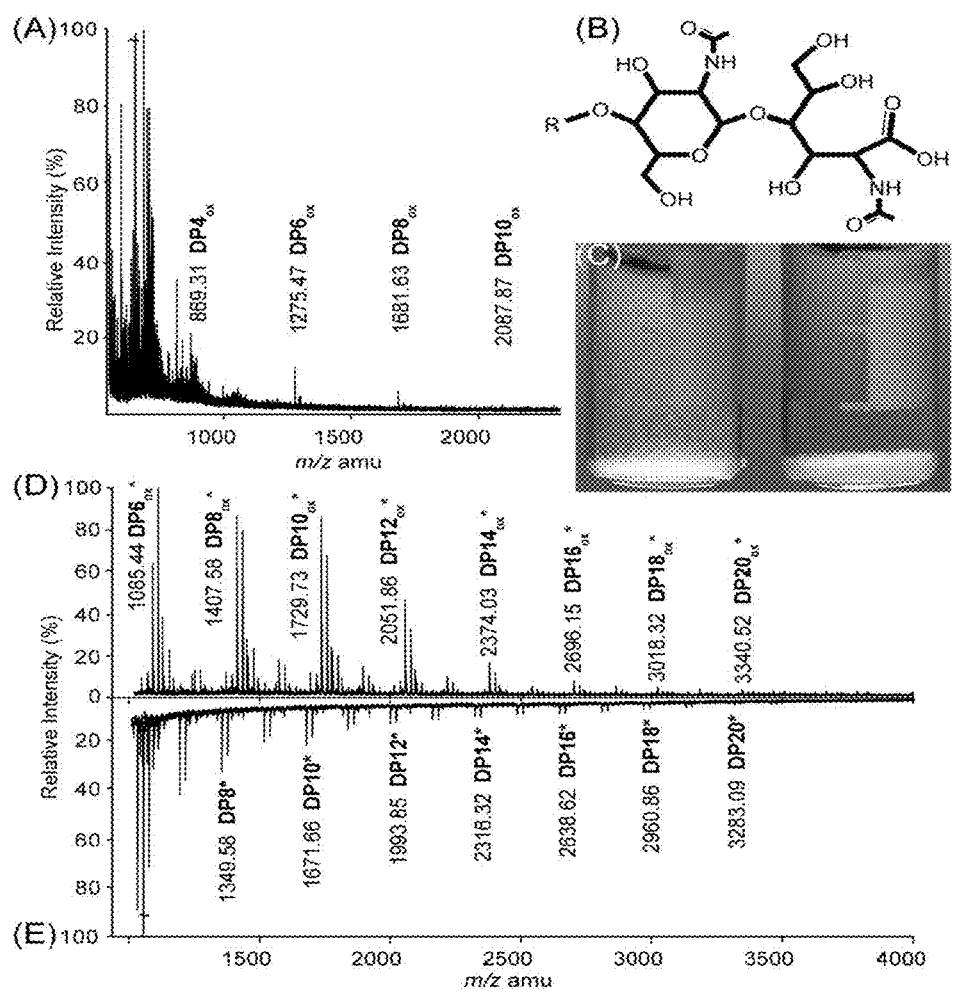
Figs. 2A, 2B, 2C, 2D, & 2E

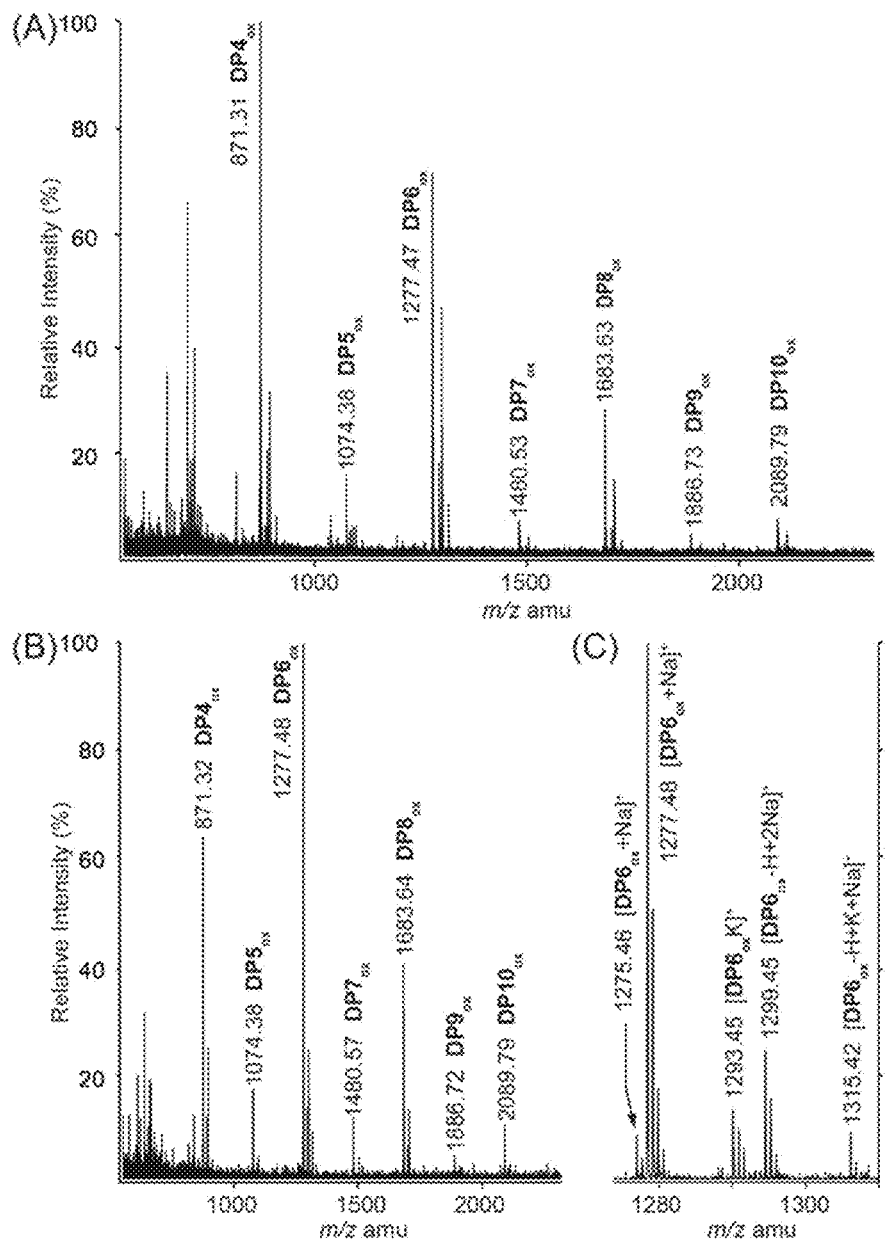
Figs. 7A, 7B, 7C, & 7D

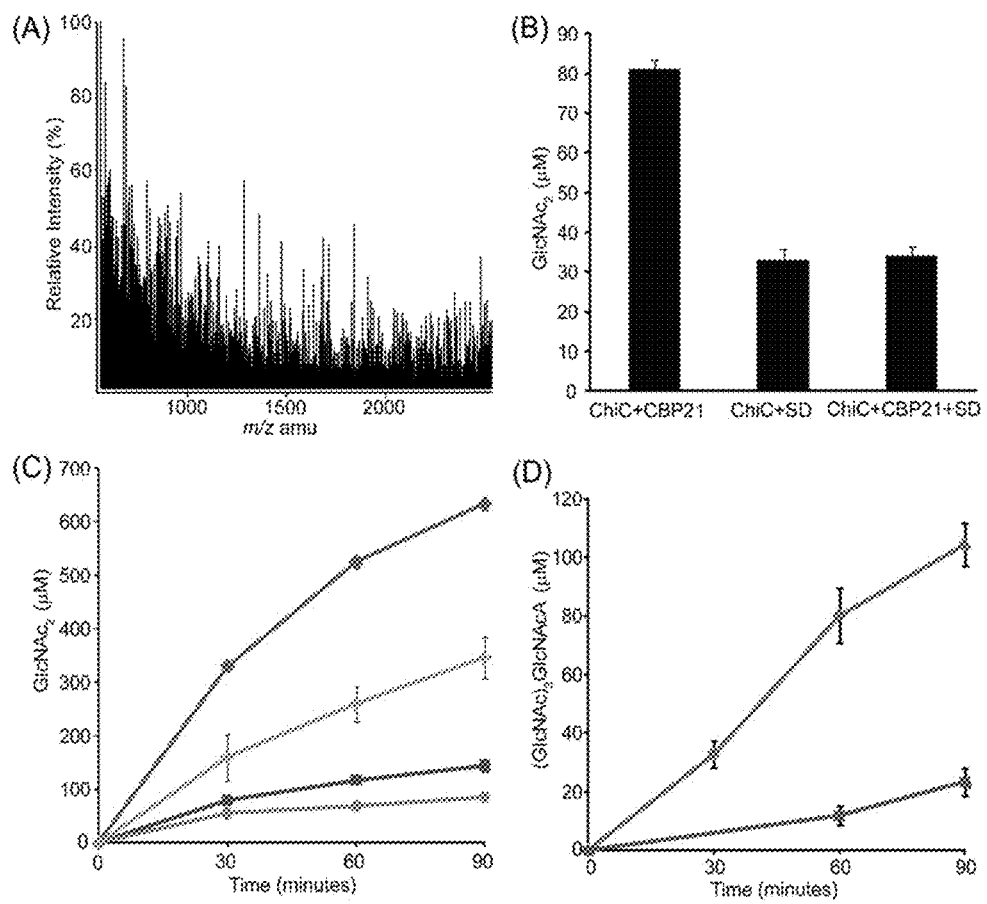
Figs. 8A, 8B, 8C, & 8D

Figs. 13A, 13B, 13C, & 13D

```
TtGH61E    HYTWPRVN-----DGADWQQVRKA................DNWQDNGYVG--DVTS
HjGH61B    HGQVQNFT-----INGQYNQGFIL.YYQ.N.....VA.YYAEDL-DLGFISPDQYTT
HjGH61A    HGHINDIV-----INGVWYQAYDP....YE.....P.YVG..TAADLDNGFVSPDAYQN
            *  :        .    :                         .   *  .   .

TtGH61E    PQIRCFQATPS---PAPSVLNTTAGSTVTYWANPDVY-HP-GPVQFYMARVPDGEDINSW
HjGH61B    PDIVCHKNAAP---GAISATAAA-GSNIVFQWGPGVWPRPYGPIVTYVVECS--GSCTTV
HjGH61A    PDIICHKNATN----AKGHASVKAGDTILFQWVPVPWPHP-GPIVDYLANCN--GDCETV
            *:: *.:          .    *..:  :   . :**  * :  :           .

TtGH61E    NGDGAVWFKVYEDHPTFG-AQLTWPSTGK----SSFAVPIPPCIKSGYYLLPAEQIGLHV
HjGH61B    NKNNLRWVKIQEAGINYN-TQV-WAQQDLINQGNKWTVKIPSSLRPGNYVFRHELLAANG
HjGH61A    DKTTLEFFKIDGVGLLSGGDPGTWASDVLISNNNTWVVKIPDNLAPGNYVLRHEIIALSS
             :.*:        :    .    .  **    :   * *:::*  *  :.  *

TtGH61E    AQSVGGAGFIISCAQLSVTGGGSTEPPNKVAFPGAYSATDPGILINIYPVP--TSYQNP
HjGH61B    ASSANGMQNFPQCVNIAVTGSGTKALPAGTPATQLYKPTDPGILFNPTTI---TSYTIP
HjGH61A    AGQANGASNFPQCFNIAVSGSGSLQ-PSGVLGTDLYHATDPGVLINITSP---LNYIIP
            * .*  * *  :: * ...*.   .   .    *  :**:*:* *       .* *

TtGH61E    GPAVFSC-----------------------------------------------------
HjGH61B    GPALW-------------------------------------------------------
HjGH61A    GPTVVSGLPTSVAQGSSAATATASATVPGGGSGPTSRTTTTARTTQASSRPSSTPPATTS
           **::

TtGH61E    ------------------------------------------------
HjGH61B    ------------------------------------------------
HjGH61A    APAGGPTQTLYGQCGGSGYSGPTRCAPPATCSTLNPYYAQCLN
```

Fig. 32A

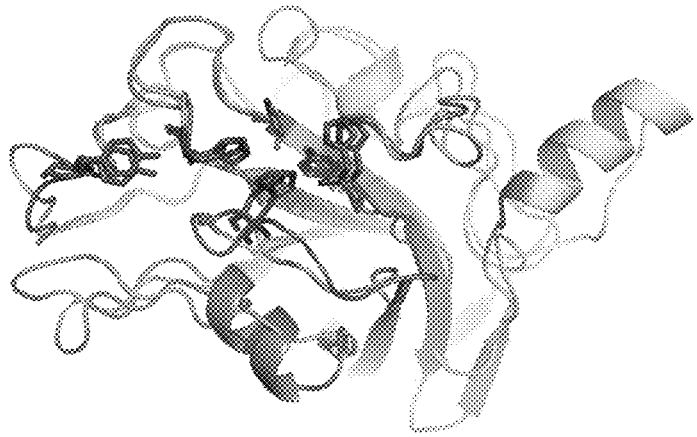

Fig. 32B

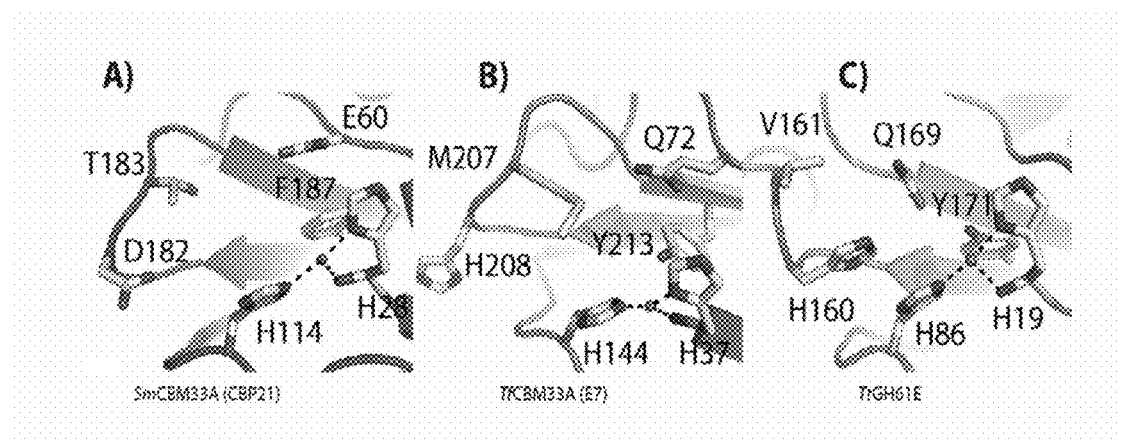
Figs. 33A, 33B, & 33C

SEQUENCE LISTING

<160> NUMBER OF SEQ ID NOS: 22

<210> SEQ ID NO 1

<211> LENGTH: 452
<212> TYPE: PRT
<213> ORGANISM: T. terrestris

<400> SEQUENCE: 1

```
Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys Met Leu Ala Asn Gly Ala Ile Val Phe Leu Ala Ala Ala Leu
225                 230                 235                 240

Gly Val Ser Gly His Tyr Thr Trp Pro Arg Val Asn Asp Gly Ala Asp
                245                 250                 255

Trp Gln Gln Val Arg Lys Ala Asp Asn Trp Gln Asp Asn Gly Tyr Val
            260                 265                 270

Gly Asp Val Thr Ser Pro Gln Ile Arg Cys Phe Gln Ala Thr Pro Ser
        275                 280                 285

Pro Ala Pro Ser Val Leu Asn Thr Thr Ala Gly Ser Thr Val Thr Tyr
    290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
                325                 330                 335

Ala Val Trp Phe Lys Val Tyr Glu Asp His Pro Thr Phe Gly Ala Gln
            340                 345                 350

Leu Thr Trp Pro Ser Thr Gly Lys Ser Ser Phe Ala Val Pro Ile Pro
        355                 360                 365

Pro Cys Ile Lys Ser Gly Tyr Tyr Leu Leu Arg Ala Glu Gln Ile Gly
    370                 375                 380

Leu His Val Ala Gln Ser Val Gly Gly Ala Gln Phe Tyr Ile Ser Cys
```

-continued

```
                385                 390                 395                 400
Ala Gln Leu Ser Val Thr Gly Gly Ser Thr Glu Pro Pro Asn Lys
                    405                 410                 415

Val Ala Phe Pro Gly Ala Tyr Ser Ala Thr Asp Pro Gly Ile Leu Ile
                420                 425                 430

Asn Ile Tyr Tyr Pro Val Pro Thr Ser Tyr Gln Asn Pro Gly Pro Ala
                    435                 440                 445

Val Phe Ser Cys
            450

<210> SEQ ID NO 2
<211> LENGTH: 250
<212> TYPE: PRT
<213> ORGANISM: T. aurantiacus

<400> SEQUENCE: 2

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Lys Tyr Tyr Gly Gly Tyr Leu Val Asn Gln Tyr Pro Tyr Met Ser
            35                  40                  45

Asn Pro Pro Glu Val Ile Ala Trp Ser Thr Thr Ala Thr Asp Leu Gly
50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
                100                 105                 110

Ile Asn Tyr Leu Ala Pro Cys Asn Gly Asp Cys Ser Thr Val Asp Lys
            115                 120                 125

Thr Gln Leu Glu Phe Phe Lys Ile Ala Glu Ser Gly Leu Ile Asn Asp
130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
            195                 200                 205

Gly Ser Asp Asn Pro Ala Gly Thr Leu Gly Thr Ala Leu Tyr His Asp
        210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 3
<211> LENGTH: 276
<212> TYPE: PRT
<213> ORGANISM: T. terrestris

<400> SEQUENCE: 3

Ala Ser Asp Asp Ile Arg Cys Asn Val Gly Thr Ser Arg Pro Thr Val
```

```
1               5                   10                  15
Lys Cys Pro Val Lys Ala Gly Ser Thr Val Thr Ile Glu Met His Gln
                20                  25                  30

Gln Pro Gly Asp Arg Ser Cys Ala Asn Glu Ala Ile Gly Gly Asp His
                35                  40                  45

Tyr Gly Pro Val Met Val Tyr Met Ser Lys Val Asp Asp Ala Val Thr
                50                  55                  60

Ala Asp Gly Ser Ser Gly Trp Phe Lys Val Phe Gln Asp Ser Trp Ala
65                  70                  75                  80

Lys Asn Pro Ser Gly Ser Thr Gly Asp Asp Tyr Trp Gly Thr Lys
                85                  90                  95

Asp Leu Asn Ser Cys Cys Gly Lys Met Asn Val Lys Ile Pro Glu Asp
                100                 105                 110

Ile Glu Pro Gly Asp Tyr Leu Leu Arg Ala Glu Val Ile Ala Leu His
                115                 120                 125

Val Ala Ala Ser Ser Gly Gly Ala Gln Phe Tyr Met Ser Cys Tyr Gln
130                 135                 140

Leu Thr Val Thr Gly Ser Gly Ser Ala Thr Pro Ser Thr Val Asn Phe
145                 150                 155                 160

Pro Gly Ala Tyr Ser Ala Ser Asp Pro Gly Ile Leu Ile Asn Ile His
                165                 170                 175

Ala Pro Met Ser Thr Tyr Val Val Pro Gly Pro Thr Val Tyr Ala Gly
                180                 185                 190

Gly Ser Thr Lys Ser Ala Gly Ser Ser Cys Ser Gly Cys Glu Ala Thr
                195                 200                 205

Cys Thr Val Gly Ser Gly Pro Ser Ala Thr Leu Thr Gln Pro Thr Ser
                210                 215                 220

Thr Ala Thr Ala Thr Ser Ala Pro Gly Gly Gly Ser Gly Cys Thr
225                 230                 235                 240

Ala Ala Lys Tyr Gln Gln Cys Gly Gly Thr Gly Tyr Thr Gly Cys Thr
                245                 250                 255

Thr Cys Ala Ser Gly Ser Thr Cys Ser Ala Val Ser Pro Pro Tyr Tyr
                260                 265                 270

Ser Gln Cys Leu
                275

<210> SEQ ID NO 4
<211> LENGTH: 197
<212> TYPE: PRT
<213> ORGANISM: Serratia marescens

<400> SEQUENCE: 4

Met Asn Lys Thr Ser Arg Thr Leu Leu Ser Leu Gly Leu Leu Ser Ala
1               5                   10                  15

Ala Met Phe Gly Val Ser Gln Gln Ala Asn Ala His Gly Tyr Val Glu
                20                  25                  30

Ser Pro Ala Ser Arg Ala Tyr Gln Cys Lys Leu Gln Leu Asn Thr Gln
                35                  40                  45

Cys Gly Ser Val Gln Tyr Glu Pro Gln Ser Val Glu Gly Leu Lys Gly
                50                  55                  60

Phe Pro Gln Ala Gly Pro Ala Asp Gly His Ile Ala Ser Ala Asp Lys
65                  70                  75                  80

Ser Thr Phe Phe Glu Leu Asp Gln Gln Thr Pro Thr Arg Trp Asn Lys
                85                  90                  95
```

```
Leu Asn Leu Lys Thr Gly Pro Asn Ser Phe Thr Trp Lys Leu Thr Ala
                100                 105                 110

Arg His Ser Thr Thr Ser Trp Arg Tyr Phe Ile Thr Lys Pro Asn Trp
            115                 120                 125

Asp Ala Ser Gln Pro Leu Thr Arg Ala Ser Phe Asp Leu Thr Pro Phe
        130                 135                 140

Cys Gln Phe Asn Asp Gly Gly Ala Ile Pro Ala Ala Gln Val Thr His
145                 150                 155                 160

Gln Cys Asn Ile Pro Ala Asp Arg Ser Gly Ser His Val Ile Leu Ala
                165                 170                 175

Val Trp Asp Ile Ala Asp Thr Ala Asn Ala Phe Tyr Gln Ala Ile Asp
            180                 185                 190

Val Asn Leu Ser Lys
            195

<210> SEQ ID NO 5
<211> LENGTH: 194
<212> TYPE: PRT
<213> ORGANISM: Enterococcus faecalis

<400> SEQUENCE: 5

Met Lys Lys Ser Leu Leu Thr Ile Val Leu Ala Phe Ser Phe Val Leu
1               5                   10                  15

Gly Gly Ala Ala Leu Ala Pro Thr Val Ser Glu Ala His Gly Tyr Val
            20                  25                  30

Ala Ser Pro Gly Ser Arg Ala Phe Phe Gly Ser Ser Ala Gly Gly Asn
        35                  40                  45

Leu Asn Thr Asn Val Gly Arg Ala Gln Trp Glu Pro Gln Ser Ile Glu
    50                  55                  60

Ala Pro Lys Asn Thr Phe Ile Thr Gly Lys Leu Ala Ser Ala Gly Val
65                  70                  75                  80

Ser Gly Phe Glu Pro Leu Asp Glu Gln Thr Ala Thr Arg Trp His Lys
                85                  90                  95

Thr Asn Ile Thr Thr Gly Pro Leu Asp Ile Thr Trp Asn Leu Thr Ala
                100                 105                 110

Gln His Arg Thr Ala Ser Trp Asp Tyr Tyr Ile Thr Lys Asn Gly Trp
            115                 120                 125

Asn Pro Asn Gln Pro Leu Asp Ile Lys Asn Phe Asp Lys Ile Ala Ser
        130                 135                 140

Ile Asp Gly Lys Gln Glu Val Pro Asn Lys Val Val Lys Gln Thr Ile
145                 150                 155                 160

Asn Ile Pro Thr Asp Arg Lys Gly Tyr His Val Ile Tyr Ala Val Trp
                165                 170                 175

Gly Ile Gly Asp Thr Val Asn Ala Phe Tyr Gln Ala Ile Asp Val Asn
            180                 185                 190

Ile Gln

<210> SEQ ID NO 6
<211> LENGTH: 222
<212> TYPE: PRT
<213> ORGANISM: Thermobifida fusca

<400> SEQUENCE: 6

Met His Arg Tyr Ser Arg Thr Gly Lys His Arg Trp Thr Val Arg Ala
1               5                   10                  15

Leu Ala Val Leu Phe Thr Ala Leu Leu Gly Leu Thr Gln Trp Thr Ala
```

```
            20                  25                  30
Pro Ala Ser Ala His Gly Ser Val Ile Asn Pro Ala Thr Arg Asn Tyr
            35                  40                  45
Gly Cys Trp Leu Arg Trp Gly His Asp His Leu Asn Pro Asn Met Gln
        50                  55                  60
Tyr Glu Asp Pro Met Cys Trp Gln Ala Trp Gln Asp Asn Pro Asn Ala
 65                  70                  75                  80
Met Trp Asn Trp Asn Gly Leu Tyr Arg Asp Trp Val Gly Gly Asn His
                85                  90                  95
Arg Ala Ala Leu Pro Asp Gly Gln Leu Cys Ser Gly Gly Leu Thr Glu
            100                 105                 110
Gly Gly Arg Tyr Arg Ser Met Asp Ala Val Gly Pro Trp Lys Thr Thr
            115                 120                 125
Asp Val Asn Asn Thr Phe Thr Ile His Leu Tyr Asp Gln Ala Ser His
            130                 135                 140
Gly Ala Asp Tyr Phe Leu Val Tyr Val Thr Lys Gln Gly Phe Asp Pro
145                 150                 155                 160
Thr Thr Gln Pro Leu Thr Trp Asp Ser Leu Glu Leu Val His Gln Thr
            165                 170                 175
Gly Ser Tyr Pro Pro Ala Gln Asn Ile Gln Phe Thr Val His Ala Pro
            180                 185                 190
Asn Arg Ser Gly Arg His Val Val Phe Thr Ile Trp Lys Ala Ser His
            195                 200                 205
Met Asp Gln Thr Tyr Tyr Leu Cys Ser Asp Val Asn Phe Val
            210                 215                 220

<210> SEQ ID NO 7
<211> LENGTH: 364
<212> TYPE: PRT
<213> ORGANISM: Streptomyces coelicolor

<400> SEQUENCE: 7

Met Val Arg Arg Thr Arg Leu Leu Thr Leu Ala Ala Val Leu Ala Thr
 1               5                  10                  15
Leu Leu Gly Ser Leu Gly Val Thr Leu Leu Gly Gln Gly Arg Ala
            20                  25                  30
Glu Ala His Gly Val Ala Met Met Pro Gly Ser Arg Thr Tyr Leu Cys
            35                  40                  45
Gln Leu Asp Ala Lys Thr Gly Thr Gly Ala Leu Asp Pro Thr Asn Pro
        50                  55                  60
Ala Cys Gln Ala Ala Leu Asp Gln Ser Gly Ala Thr Ala Leu Tyr Asn
 65                  70                  75                  80
Trp Phe Ala Val Leu Asp Ser Asn Ala Gly Gly Arg Gly Ala Gly Tyr
                85                  90                  95
Val Pro Asp Gly Thr Leu Cys Ser Ala Gly Asp Arg Ser Pro Tyr Asp
            100                 105                 110
Phe Ser Ala Tyr Asn Ala Ala Arg Ser Asp Trp Pro Arg Thr His Leu
            115                 120                 125
Thr Ser Gly Ala Thr Ile Pro Val Glu Tyr Ser Asn Trp Ala Ala His
            130                 135                 140
Pro Gly Asp Phe Arg Val Tyr Leu Thr Lys Pro Gly Trp Ser Pro Thr
145                 150                 155                 160
Ser Glu Leu Gly Trp Asp Asp Leu Glu Leu Ile Gln Thr Val Thr Asn
            165                 170                 175
```

Pro Pro Gln Gln Gly Ser Pro Gly Thr Asp Gly His Tyr Tyr Trp
            180                 185                 190

Asp Leu Ala Leu Pro Ser Gly Arg Ser Gly Asp Ala Leu Ile Phe Met
        195                 200                 205

Gln Trp Val Arg Ser Asp Ser Gln Glu Asn Phe Phe Ser Cys Ser Asp
    210                 215                 220

Val Val Phe Asp Gly Gly Asn Gly Glu Val Thr Gly Ile Arg Gly Ser
225                 230                 235                 240

Gly Ser Thr Pro Asp Pro Asp Pro Thr Pro Thr Pro Thr Asp Pro Thr
            245                 250                 255

Thr Pro Pro Thr His Thr Gly Ser Cys Met Ala Val Tyr Ser Val Glu
            260                 265                 270

Asn Ser Trp Ser Gly Gly Phe Gln Gly Ser Val Glu Val Met Asn His
            275                 280                 285

Gly Thr Glu Pro Leu Asn Gly Trp Ala Val Gln Trp Gln Pro Gly Gly
            290                 295                 300

Gly Thr Thr Leu Gly Gly Val Trp Asn Gly Ser Leu Thr Ser Gly Ser
305                 310                 315                 320

Asp Gly Thr Val Thr Val Arg Asn Val Asp His Asn Arg Val Val Pro
            325                 330                 335

Pro Asp Gly Ser Val Thr Phe Gly Phe Thr Ala Thr Ser Thr Gly Asn
            340                 345                 350

Asp Phe Pro Val Asp Ser Ile Gly Cys Val Ala Pro
            355                 360

<210> SEQ ID NO 8
<211> LENGTH: 400
<212> TYPE: PRT
<213> ORGANISM: Cellulomonas flavigena DSM 20109

<400> SEQUENCE: 8

Met Pro Arg His Arg Ser Thr Arg Arg Ala Leu Ala Gly Leu Ala Ala
1               5                   10                  15

Thr Ala Val Val Thr Thr Ala Leu Val Thr Val Pro Thr Val Ala Gln
            20                  25                  30

Ala His Gly Gly Leu Thr Asn Pro Pro Thr Arg Thr Tyr Ala Cys Tyr
        35                  40                  45

Gln Asp Gly Leu Ala Gly Ala Ala Ala Gly Glu Ala Gly Asn Ile
    50                  55                  60

Arg Pro Arg Asn Ala Ala Cys Val Asn Ala Phe Asp Asn Glu Gly Asn
65                  70                  75                  80

Tyr Ser Phe Tyr Asn Trp Tyr Gly Asn Leu Leu Gly Thr Ile Ala Gly
            85                  90                  95

Arg His Glu Thr Ile Ala Asp Gly Lys Val Cys Gly Pro Asp Ala Arg
            100                 105                 110

Phe Ala Ser Tyr Asn Thr Pro Ser Ser Ala Trp Pro Thr Thr Lys Val
        115                 120                 125

Thr Pro Gly Gln Thr Met Thr Phe Gln Tyr Ala Ala Val Ala Arg His
    130                 135                 140

Pro Gly Trp Phe Thr Thr Trp Ile Thr Lys Asp Gly Trp Asn Gln Asn
145                 150                 155                 160

Glu Pro Ile Gly Trp Asp Asp Leu Glu Pro Ala Pro Phe Asp Arg Val
            165                 170                 175

Leu Asp Pro Pro Leu Arg Glu Gly Gly Pro Ala Gly Pro Glu Tyr Trp
            180                 185                 190

```
Trp Asn Val Lys Leu Pro Ser Asn Lys Ser Gly Lys His Val Leu Phe
            195                 200                 205

Asn Ile Trp Glu Arg Thr Asp Ser Pro Glu Ser Phe Tyr Asn Cys Val
210                 215                 220

Asp Val Asp Phe Gly Gly Gly Thr Val Thr Pro Ser Pro Thr Pro
225                 230                 235                 240

Ser Val Thr Pro Thr Arg Thr Pro Thr Pro Ser Pro Thr Pro Ser Val
            245                 250                 255

Thr Pro Ser Pro Thr Pro Ser Val Thr Pro Thr Pro Thr Pro Thr Pro
            260                 265                 270

Thr Pro Thr Pro Ser Pro Thr Pro Thr Leu Thr Val Thr Pro Thr Pro
            275                 280                 285

Thr Pro Thr Ser Val Pro Gly Asp Ser Val Cys Glu Leu Glu Val Asp
            290                 295                 300

Thr Ser Ser Ala Trp Pro Gly Gly Phe Gln Gly Thr Val Thr Val Phe
305                 310                 315                 320

Asn Ala Thr Met Glu Pro Val Asn Gly Trp Gln Val Ser Trp Lys Phe
                325                 330                 335

Thr Asn Gly Glu Thr Ile Ala Gln Ser Trp Ser Gly Val Thr Ser Gln
            340                 345                 350

Ser Gly Ser Thr Val Thr Val Lys Asn Ala Asp Trp Asn Ser Thr Ile
            355                 360                 365

Ala His His Asn Ala Val Asn Phe Gly Phe Ile Gly Ser Gly Thr Pro
            370                 375                 380

Lys Ala Val Thr Asp Ala Thr Leu Asn Gly Lys Pro Cys Ile Val Arg
385                 390                 395                 400

<210> SEQ ID NO 9
<211> LENGTH: 362
<212> TYPE: PRT
<213> ORGANISM: Cellulomonas flavigena

<400> SEQUENCE: 9

Met Phe Ile Pro Thr Arg Ser Arg Phe Gly Arg Leu Ala Arg Leu Ala
1               5                   10                  15

Leu Ala Val Pro Leu Ala Leu Ala Ala Thr Gly Ile Val Ala Thr Ser
                20                  25                  30

Ala Ser Ala His Gly Ser Val Thr Asp Pro Pro Ser Arg Asn Tyr Gly
            35                  40                  45

Cys Trp Glu Arg Glu Gly Gly Thr His Met Asp Pro Ala Met Ala Gln
50                  55                  60

Arg Asp Pro Met Cys Trp Gln Ala Phe Gln Ala Asn Pro Asn Thr Met
65                  70                  75                  80

Trp Asn Trp Asn Gly Asn Phe Arg Glu Gly Val Gly Gly Arg His Glu
                85                  90                  95

Gln Val Ile Pro Asp Asp Gln Leu Cys Ser Ala Gly Lys Thr Gln Asn
                100                 105                 110

Gly Leu Tyr Ala Ser Leu Asp Thr Pro Gly Pro Trp Ile Met Lys Thr
            115                 120                 125

Val Pro His Asn Phe Thr Leu Thr Leu Thr Asp Gly Ala Met His Gly
            130                 135                 140

Ala Asp Tyr Met Arg Ile Tyr Val Ser Lys Ala Gly Tyr Asp Pro Thr
145                 150                 155                 160

Thr Asp Pro Leu Gly Trp Asp Asp Ile Glu Leu Ile Lys Glu Thr Gly
```

```
                    165                 170                 175
Arg Tyr Gly Thr Thr Gly Leu Tyr Gln Ala Asp Val Ser Ile Pro Ser
            180                 185                 190

Asn Arg Thr Gly Arg Ala Val Leu Phe Thr Ile Trp Gln Ala Ser His
        195                 200                 205

Leu Asp Gln Pro Tyr Tyr Ile Cys Ser Asp Ile Asn Ile Asn Gly Thr
    210                 215                 220

Ala Pro Thr Gln Gln Pro Thr Gln Gln Pro Thr Gln Gln Pro Thr Gln
225                 230                 235                 240

Gln Pro Thr Gln Gln Pro Thr Gln Gln Pro Thr Gln Gln Pro Thr Gln
                245                 250                 255

Gln Pro Thr Gln Gln Pro Thr Gln Pro Thr Gln Asn Pro Gly Thr
            260                 265                 270

Gly Ala Cys Thr Ala Thr Val Lys Ala Ala Ser Thr Trp Gly Asn Gly
        275                 280                 285

Trp Gln Gly Glu Val Thr Val Thr Ala Gly Ser Ser Ala Ile Asn Gly
    290                 295                 300

Trp Lys Val Thr Val Gly Gly Ala Ser Ile Thr Gln Ala Trp Ser Gly
305                 310                 315                 320

Ser Tyr Ser Gly Gly Thr Phe Ser Asn Ala Glu Trp Asn Gly Lys Leu
                325                 330                 335

Ala Ala Gly Ala Ser Thr Thr Ala Gly Phe Ile Ala Ser Gly Thr Pro
            340                 345                 350

Gly Thr Leu Thr Ala Thr Cys Thr Ala Ala
        355                 360

<210> SEQ ID NO 10
<211> LENGTH: 368
<212> TYPE: PRT
<213> ORGANISM: Cellulomonas flavigena DSM 20109

<400> SEQUENCE: 10

Met Ser Arg Ile Ser Pro Leu Arg Arg Val Ala Ala Ala Cys Gly Ala
1               5                   10                  15

Leu Ala Ile Gly Ala Ala Thr Val Val Gly Ser Ile Ala Leu Ala Ala
            20                  25                  30

Pro Ala Ser Ala His Gly Ala Val Ser Asp Pro Pro Ser Arg Ile Tyr
        35                  40                  45

Gly Cys Trp Glu Arg Trp Ala Ser Asn Phe Thr Asp Pro Ala Met Ala
    50                  55                  60

Thr Ser Asp Pro Gln Cys Trp Asp Ala Trp Gln Ser Glu Pro Gln Ala
65                  70                  75                  80

Met Trp Asn Trp Asn Gly Met Phe Lys Glu Gly Ala Ala Gly Gln His
                85                  90                  95

Glu Gln Ser Ile Pro Asp Gly Lys Leu Cys Ser Ala Asp Asn Pro Leu
            100                 105                 110

Tyr Ala Ala Ala Asp Asp Pro Gly Pro Trp Arg Thr Thr Pro Val Asp
        115                 120                 125

His Asp Phe Arg Leu Thr Leu His Asp Pro Ser Asn His Gly Ala Asp
    130                 135                 140

Tyr Leu Lys Ile Tyr Val Thr Lys Gln Gly Tyr Asp Ala Arg Ser Glu
145                 150                 155                 160

Ala Leu Thr Trp Ala Asp Leu Glu Leu Val Lys Thr Thr Gly Arg Tyr
                165                 170                 175
```

```
Ala Thr Ser Ser Pro Tyr Val Thr Asp Val Ser Val Pro Arg Asp Arg
            180                 185                 190

Thr Gly His His Val Val Phe Thr Ile Trp Gln Ala Ser His Leu Asp
            195                 200                 205

Gln Pro Tyr Tyr Gln Cys Ser Asp Val Thr Phe Gly Gly Gly Gly Thr
            210                 215                 220

Pro Thr Thr Ser Pro Thr Thr Pro Ala Pro Thr Pro Thr Thr Pro Ala
225                 230                 235                 240

Pro Thr Thr Pro Ala Pro Thr Pro Thr Pro Ala Pro Thr Thr Pro
                245                 250                 255

Ala Pro Thr Thr Pro Ala Pro Thr Thr Pro Ala Pro Thr Thr Pro Ala
            260                 265                 270

Pro Thr Gln Pro Ala Asp Gly Ala Cys Thr Ala Ala Ile Glu Val Val
            275                 280                 285

Ser Ala Trp Gln Gly Gly Tyr Gln Ala Thr Val Thr Val Thr Ala Gly
            290                 295                 300

Ser Gly Gly Leu Asp Gly Trp Thr Val Thr Val Pro Gly Ala Thr Ile
305                 310                 315                 320

Thr Gln Ala Trp Asn Gly Thr Ala Thr Gly Ser Thr Ile Thr Ala Ala
            325                 330                 335

Gly Trp Asn Gly Thr Val Ala Ala Gly Gly Thr Ala Gly Val Gly Phe
            340                 345                 350

Leu Gly Ser Gly Ser Pro Asp Gly Leu Thr Ala Thr Cys Ala Ala Ala
            355                 360                 365

<210> SEQ ID NO 11
<211> LENGTH: 313
<212> TYPE: PRT
<213> ORGANISM: Cellulomonas flavigena DSM 20109

<400> SEQUENCE: 11

Met Arg Ser His Ala Leu Pro Arg Ser Ala Arg Pro Thr Pro Gly Arg
1               5                   10                  15

Leu Leu Leu Ser Val Leu Ala Val Ile Ala Leu Ala Phe Ala Val Leu
            20                  25                  30

Thr Val Ala Pro Ala Pro Ser Ala Gln Ala His Gly Trp Ile Ser Asp
        35                  40                  45

Pro Pro Ser Arg Gln Asp Leu Cys Tyr Thr Gly Ala Val Ser Asn Cys
    50                  55                  60

Gly Pro Val Met Tyr Glu Pro Trp Ser Val Glu Ala Lys Lys Gly Ser
65                  70                  75                  80

Met Gln Cys Ser Gly Gly Arg Phe Thr Glu Leu Asp Asn Glu Ser
            85                  90                  95

Arg Ser Trp Pro Arg Gln Asn Leu Lys Thr Asn Gln Val Phe Thr Trp
            100                 105                 110

Asp Ile Val Ala Asn His Ser Thr Ser Thr Trp Glu Tyr Phe Val Asp
            115                 120                 125

Gly Arg Leu His Thr Thr Ile Asp Asp Lys Gly Ala Leu Pro Pro Asn
            130                 135                 140

Arg Phe Thr His Thr Ile Asn Asn Leu Pro Glu Gly Asn His Lys Ile
145                 150                 155                 160

Phe Val Arg Trp Asn Ile Ala Asp Thr Val Asn Ala Phe Tyr Gln Cys
            165                 170                 175

Ile Asp Ala Tyr Ile Thr Pro Gly Gly Thr Pro Gly Pro Thr Gln Gln
            180                 185                 190
```

```
Pro Thr Gln Gln Pro Thr Gln Gln Pro Thr Gln Gln
        195                 200                 205

Pro Thr Gln Gln Pro Thr Gln Gln Pro Gly Asn Gly
        210                 215                 220

Ala Cys Thr Ala Thr Phe Lys Thr Asn Ala Trp Gly Asn Gly Tyr
225                 230                 235                 240

Gln Gly Glu Ile Thr Val Thr Ala Gly Ser Ser Ala Ile Arg Gly Trp
                245                 250                 255

Lys Val Thr Val Asn Gly Ala Thr Ile Thr Gln Ala Trp Ser Ser Gln
                260                 265                 270

Leu Ser Gly Ser Thr Leu Ser Asn Ala Ser Trp Asn Gly Ser Leu Asn
                275                 280                 285

Ala Gly Ala Ser Thr Thr Leu Gly Phe Ile Ala Asn Gly Thr Pro Ser
290                 295                 300

Gly Val Thr Ala Thr Cys Ala Ala Ala
305                 310
```

<210> SEQ ID NO 12
<211> LENGTH: 397
<212> TYPE: PRT
<213> ORGANISM: Cellvibrio japonicus Ueda 107

<400> SEQUENCE: 12

```
Met Phe Asn Thr Arg His Leu Leu Ala Gly Val Ser Gln Leu Val Lys
1               5                   10                  15

Pro Ala Ser Met Met Ile Leu Ala Met Ala Ser Thr Leu Ala Ile His
                20                  25                  30

Glu Ala Ser Ala His Gly Tyr Val Ser Ser Pro Lys Ser Arg Val Ile
            35                  40                  45

Gln Cys Lys Glu Asn Gly Ile Glu Asn Pro Thr His Pro Ala Cys Ile
        50                  55                  60

Ala Ala Lys Ala Ala Gly Asn Gly Gly Leu Tyr Thr Pro Gln Glu Val
65                  70                  75                  80

Ala Val Gly Gly Val Arg Asp Asn His Asp Tyr Tyr Ile Pro Asp Gly
                85                  90                  95

Arg Leu Cys Ser Ala Asn Arg Ala Asn Leu Phe Gly Met Asp Leu Ala
                100                 105                 110

Arg Asn Asp Trp Pro Ala Thr Ser Val Thr Pro Gly Ala Arg Glu Phe
            115                 120                 125

Val Trp Thr Asn Thr Ala Ala His Lys Thr Lys Tyr Phe Arg Tyr Tyr
        130                 135                 140

Ile Thr Pro Gln Gly Tyr Asp His Ser Gln Pro Leu Arg Trp Ser Asp
145                 150                 155                 160

Leu Gln Leu Ile His Asp Ser Gly Pro Ala Asp Gln Glu Trp Val Ser
                165                 170                 175

Thr His Asn Val Ile Leu Pro Tyr Arg Thr Gly Arg His Ile Ile Tyr
                180                 185                 190

Ser Ile Trp Gln Arg Asp Trp Asp Arg Asp Ala Ala Glu Gly Phe Tyr
            195                 200                 205

Gln Cys Ile Asp Val Asp Phe Gly Asn Gly Thr Gly Thr Gly Ser Ser
        210                 215                 220

Ser Ser Val Ala Ser Val Val Ser Val Thr Ser Ser Ser Val
225                 230                 235                 240

Ala Ser Ser Val Ala Ser Ser Leu Ser Asn Asp Thr Cys Ala Thr Leu
```

```
            245                 250                 255
Pro Ser Trp Asp Ala Ser Thr Val Tyr Thr Asn Pro Gln Gln Val Lys
            260                 265                 270

His Asn Ser Lys Arg Tyr Gln Ala Asn Tyr Trp Thr Gln Asn Gln Asn
            275                 280                 285

Pro Ser Thr Asn Ser Gly Gln Tyr Gly Pro Trp Leu Asp Leu Gly Asn
            290                 295                 300

Cys Val Thr Ser Gly Gly Ser Ser Val Ala Ser Ser Ser Val Ala
305                 310                 315                 320

Ser Ser Val Ala Ser Ser Val Thr Ser Ser Val Ala Ser Ser Val Val
            325                 330                 335

Ser Gly Asn Cys Ile Ser Pro Val Tyr Val Asp Gly Ser Ser Tyr Ala
            340                 345                 350

Asn Asn Ala Leu Val Gln Asn Asn Gly Ser Glu Tyr Arg Cys Leu Val
            355                 360                 365

Gly Gly Trp Cys Thr Val Gly Gly Pro Tyr Ala Pro Gly Thr Gly Trp
            370                 375                 380

Ala Trp Ala Asn Ala Trp Glu Leu Val Arg Ser Cys Gln
385                 390                 395

<210> SEQ ID NO 13
<211> LENGTH: 337
<212> TYPE: PRT
<213> ORGANISM: Cellvibrio japonicus Ueda 107

<400> SEQUENCE: 13

Met Asn Asn Lys Phe Val Lys Met Gly Gly Met Gly Ala Leu Leu Leu
1               5                   10                  15

Ala Phe Ser Ala Leu Ser Phe Gly His Gly Phe Val Asp Ser Pro Gly
            20                  25                  30

Ala Arg Asn Tyr Phe Cys Gly Ala Val Thr Lys Pro Asp His Val Met
            35                  40                  45

Asn Gly Val Ala Arg Tyr Pro Glu Cys Ala Gly Ala Phe Ala Asn Asp
        50                  55                  60

Phe Asn Gly Gly Tyr Ser Tyr Met Ser Val Leu Thr His His Gln Gly
65                  70                  75                  80

Arg Lys Val Leu Gly Pro Val Ala Arg Asn Val Cys Gly Phe Asp Ser
                85                  90                  95

Glu Thr Trp Asn Gly Gly Lys Thr Pro Trp Asp Asn Ala Ile Asn Trp
            100                 105                 110

Pro Val Asn Asn Ile Asn Ser Gly Thr Leu Thr Phe Ser Trp Asp Ile
            115                 120                 125

Ser Asn Gly Pro His Phe Asp Asp Thr Ser Asp Phe Arg Tyr Trp Ile
        130                 135                 140

Thr Lys Pro Gly Phe Val Tyr Gln Val Gly Arg Glu Leu Thr Trp Ala
145                 150                 155                 160

Asp Phe Glu Asp Gln Pro Phe Cys Asp Leu Ala Tyr Asn Asp Asp Asn
                165                 170                 175

Pro Gly Ala Tyr Pro Asn Val Arg Ala Asp Lys Pro Asn Thr His Phe
            180                 185                 190

His Thr Thr Cys Thr Val Pro Ala Arg Thr Gly Arg His Val Ile Tyr
            195                 200                 205

Ala Glu Trp Gly Arg Glu Pro Pro Thr Tyr Glu Arg Phe His Gly Cys
            210                 215                 220
```

```
Ile Asp Val Gln Ile Gly Gly Gly Ser Asn Ser Ser Val Pro Val Ser
225                 230                 235                 240

Ser Ser Ser Ser Ser Arg Ser Ser Ser Ser Ser Leu Ala Pro Ser
            245                 250                 255

Ser Ser Ser Arg Ser Ser Ser Ser Ser Ser Val Ser Ser Ser Arg
        260                 265                 270

Ser Ser Ser Ser Ser Val Val Ser Ser Ser Ser Ser Arg Pro Ala
        275                 280                 285

Ser Ser Ser Ser Ser Ser Thr Gly Gly Ser Thr Glu Tyr Cys Asn Trp
290                 295                 300

Tyr Gly Trp Gln Val Ala Ile Cys Lys Asn Thr Thr Ser Gly Trp Ser
305                 310                 315                 320

Asn Glu Asn Gln Gln Thr Cys Ile Gly Arg Asp Thr Cys Asn Ala Pro
                325                 330                 335

Arg
```

<210> SEQ ID NO 14
<211> LENGTH: 356
<212> TYPE: PRT
<213> ORGANISM: Streptomyces coelicolor A3(2)

<400> SEQUENCE: 14

```
Met Pro Ala Pro Ser Ala Ser Arg Arg Ala Ala Val Ala Val Ala
1               5                   10                  15

Gly Leu Ala Pro Leu Ala Leu Thr Thr Leu Ala Ala Pro Ala Ser
                20                  25                  30

Ala His Gly Ser Met Gly Asp Pro Val Ser Arg Val Ser Gln Cys His
            35                  40                  45

Ala Glu Gly Pro Glu Asn Pro Lys Ser Ala Ala Cys Arg Ala Ala Val
    50                  55                  60

Ala Ala Gly Gly Thr Gln Ala Leu Tyr Asp Trp Asn Gly Ile Arg Ile
65                  70                  75                  80

Gly Asn Ala Ala Gly Lys His Gln Glu Leu Ile Pro Asp Gly Arg Leu
                85                  90                  95

Cys Ser Ala Asn Asp Pro Ala Phe Lys Gly Leu Asp Leu Ala Arg Ala
            100                 105                 110

Asp Trp Pro Ala Thr Gly Val Ser Ser Gly Ser Tyr Thr Phe Lys Tyr
        115                 120                 125

Arg Val Thr Ala Pro His Lys Gly Thr Phe Lys Val Tyr Leu Thr Lys
130                 135                 140

Pro Gly Tyr Asp Pro Ser Lys Pro Leu Gly Trp Gly Asp Leu Asp Leu
145                 150                 155                 160

Ser Ala Pro Val Ala Thr Ser Thr Asp Pro Val Ala Ser Gly Gly Phe
                165                 170                 175

Tyr Thr Phe Ser Gly Thr Leu Pro Glu Arg Ser Gly Lys His Leu Leu
            180                 185                 190

Tyr Ala Val Trp Gln Arg Ser Asp Ser Pro Glu Ala Phe Tyr Ser Cys
        195                 200                 205

Ser Asp Val Thr Phe Gly Gly Asp Gly Asp Gly Asp Gly Asp Gly Gly
    210                 215                 220

Ser Gly Ser Gly Ala Ala Thr Gly Asp Asp Thr Ala Ser Gly Asp Ala
225                 230                 235                 240

Glu Ala Gly Ala Ala Pro Ala Pro Glu Ala Ser Ala Pro Ser Glu Glu
                245                 250                 255
```

```
Gln Leu Ala Ala Ala Glu Lys Ser Thr Ile Glu His His Gly His
            260                 265                 270

Gly Asp Gln Asp Ala Ala Thr Thr Thr Asp Pro Thr Asp Pro Ala Ala
        275                 280                 285

Ala Pro Glu Glu Ala Pro Gly Thr Ala Ala Glu Pro His Gln Val Lys
    290                 295                 300

Ala Ala Gly Gly Gly Thr Glu Asn Leu Ala Glu Thr Gly Gly Asp Ser
305                 310                 315                 320

Thr Thr Pro Tyr Ile Ala Val Gly Gly Ala Ala Leu Ala Leu Gly
                325                 330                 335

Ala Ala Val Leu Phe Ala Ser Val Arg Arg Arg Ala Thr Thr Gly Gly
            340                 345                 350

Arg His Gly His
        355

<210> SEQ ID NO 15
<211> LENGTH: 323
<212> TYPE: PRT
<213> ORGANISM: Hypocrea jecorina

<400> SEQUENCE: 15

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Pro Ile Val Val
            20                  25                  30

Gly Trp Thr Ala Ala Asp Leu Asp Asn Gly Phe Val Ser Pro Asp Ala
        35                  40                  45

Tyr Gln Asn Pro Asp Ile Ile Cys His Lys Asn Ala Thr Asn Ala Lys
    50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
        115                 120                 125

Ala Ser Asp Val Leu Ile Ser Asn Asn Asn Thr Trp Val Val Lys Ile
    130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Leu Ile
        195                 200                 205

Asn Ile Tyr Thr Ser Pro Leu Asn Tyr Ile Ile Pro Gly Pro Thr Val
    210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Gly Ser Gly Pro Thr Ser
                245                 250                 255

Arg Thr Thr Thr Thr Ala Arg Thr Thr Gln Ala Ser Ser Arg Pro Ser
            260                 265                 270
```

```
Ser Thr Pro Ala Thr Thr Ser Ala Pro Ala Gly Gly Pro Thr Gln
    275                 280                 285

Thr Leu Tyr Gly Gln Cys Gly Gly Ser Gly Tyr Ser Gly Pro Thr Arg
    290                 295                 300

Cys Ala Pro Pro Ala Thr Cys Ser Thr Leu Asn Pro Tyr Tyr Ala Gln
305                 310                 315                 320

Cys Leu Asn

<210> SEQ ID NO 16
<211> LENGTH: 228
<212> TYPE: PRT
<213> ORGANISM: Hypocrea jecorina

<400> SEQUENCE: 16

His Gly Gln Val Gln Asn Phe Thr Ile Asn Gly Gln Tyr Asn Gln Gly
1               5                   10                  15

Phe Ile Leu Asp Tyr Tyr Tyr Gln Lys Gln Asn Thr Gly His Phe Pro
            20                  25                  30

Asn Val Ala Gly Trp Tyr Ala Glu Asp Leu Asp Leu Gly Phe Ile Ser
        35                  40                  45

Pro Asp Gln Tyr Thr Thr Pro Asp Ile Val Cys His Lys Asn Ala Ala
    50                  55                  60

Pro Gly Ala Ile Ser Ala Thr Ala Ala Gly Ser Asn Ile Val Phe
65                  70                  75                  80

Gln Trp Gly Pro Gly Val Trp Pro His Pro Tyr Gly Pro Ile Val Thr
                85                  90                  95

Tyr Val Val Glu Cys Ser Gly Ser Cys Thr Thr Val Asn Lys Asn Asn
            100                 105                 110

Leu Arg Trp Val Lys Ile Gln Glu Ala Gly Ile Asn Tyr Asn Thr Gln
        115                 120                 125

Val Trp Ala Gln Gln Asp Leu Ile Asn Gln Gly Asn Lys Trp Thr Val
    130                 135                 140

Lys Ile Pro Ser Ser Leu Arg Pro Gly Asn Tyr Val Phe Arg His Glu
145                 150                 155                 160

Leu Leu Ala Ala His Gly Ala Ser Ser Ala Asn Gly Met Gln Asn Tyr
                165                 170                 175

Pro Gln Cys Val Asn Ile Ala Val Thr Gly Ser Gly Thr Lys Ala Leu
            180                 185                 190

Pro Ala Gly Thr Pro Ala Thr Gln Leu Tyr Lys Pro Thr Asp Pro Gly
        195                 200                 205

Ile Leu Phe Asn Pro Tyr Thr Thr Ile Thr Ser Tyr Thr Ile Pro Gly
    210                 215                 220

Pro Ala Leu Trp
225

<210> SEQ ID NO 17
<211> LENGTH: 28
<212> TYPE: DNA
<213> ORGANISM: Artificial sequence
<220> FEATURE:
<223> OTHER INFORMATION: Primer

<400> SEQUENCE: 17
cgaagatcta cgcctctgcc tttggttc                                        28

<210> SEQ ID NO 18
```

```
<211> LENGTH: 35
<212> TYPE: DNA
<213> ORGANISM: Artificial sequence
<220> FEATURE:
<223> OTHER INFORMATION: Primer

<400> SEQUENCE: 18
gagacgtggt cgtatgtatg tgcgccgact tgatg                              35

<210> SEQ ID NO 19
<211> LENGTH: 37
<212> TYPE: DNA
<213> ORGANISM: Artificial sequence
<220> FEATURE:
<223> OTHER INFORMATION: Primer

<400> SEQUENCE: 19
caagtcggcg cacatacata cgaccacgtc tccctcc                            37

<210> SEQ ID NO 20
<211> LENGTH: 35
<212> TYPE: DNA
<213> ORGANISM: Artificial sequence
<220> FEATURE:
<223> OTHER INFORMATION: Primer

<400> SEQUENCE: 20
ccaacagtcg tagctatcaa ccctcgagca ttaac                              35

<210> SEQ ID NO 21
<211> LENGTH: 70
<212> TYPE: DNA
<213> ORGANISM: Artificial sequence
<220> FEATURE:
<223> OTHER INFORMATION: Primer

<400> SEQUENCE: 21
cagaagcttt caatgatacc acgcaatctc tccatcaccg agacaatcac caacagtcgt   60
agctatcaac                                                          70

<210> SEQ ID NO 22
<211> LENGTH: 196
<212> TYPE: PRT
<213> ORGANISM: Streptomyces coelicolor

<400> SEQUENCE: 22
```

His Gly Val Ala Met Met Pro Gly Ser Arg Thr Tyr Leu Cys Gln Leu
1               5                   10                  15

Asp Ala Lys Thr Gly Thr Gly Ala Leu Asp Pro Thr Asn Pro Ala Cys
            20                  25                  30

Gln Ala Ala Leu Asp Gln Ser Gly Ala Thr Ala Leu Tyr Asn Trp Phe
        35                  40                  45

Ala Val Leu Asp Ser Asn Ala Gly Gly Arg Gly Ala Gly Tyr Val Pro
    50                  55                  60

Asp Gly Thr Leu Cys Ser Ala Gly Asp Arg Ser Pro Tyr Asp Phe Ser
65                  70                  75                  80

Ala Tyr Asn Ala Ala Arg Ser Asp Trp Pro Arg Thr His Leu Thr Ser
                85                  90                  95

Gly Ala Thr Ile Pro Val Glu Tyr Ser Asn Trp Ala Ala His Pro Gly
            100                 105                 110

Asp Phe Arg Val Tyr Leu Thr Lys Pro Gly Trp Ser Pro Thr Ser Glu
        115                 120                 125

-continued

```
Leu Gly Trp Asp Asp Leu Glu Leu Ile Gln Thr Val Thr Asn Pro Pro
    130                 135                 140

Gln Gln Gly Ser Pro Gly Thr Asp Gly Gly His Tyr Tyr Trp Asp Leu
145             150                 155                     160

Ala Leu Pro Ser Gly Arg Ser Gly Asp Ala Leu Ile Phe Met Gln Trp
            165                 170                 175

Val Arg Ser Asp Ser Gln Glu Asn Phe Phe Ser Cys Ser Asp Val Val
            180                 185                 190

Phe Asp Gly Gly
        195
```

METHODS OF DEGRADING OR HYDROLYZING A POLYSACCHARIDE

CROSS-REFERENCE TO RELATED APPLICATIONS

This application is a divisional application of U.S. application Ser. No. 13/814,450 filed on Feb. 5, 2013, now U.S. Pat. No. 9,758,802, which is a 35 U.S.C. § 371 national application of PCT/US2011/046838 filed on Nov. 5, 2011, which claims priority or the benefit under 35 U.S.C. § 119 of GB Application No. 1105062.2 filed on Mar. 25, 2011, GB Application No. 1016858.1 filed on Oct. 6, 2010, and GB Application No. 1013317.1 filed on Aug. 6, 2010, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods of degrading or hydrolyzing a polysaccharide, such as chitin or cellulose, comprising contacting said polysaccharide with an oxido-hydrolytic enzyme, such as CBP21 or a GH61 protein, wherein said degradation or hydrolysis is carried out in the presence of at least one reducing agent and at least one divalent metal ion. The invention also extends to the use of additional saccharolytic enzymes such as hydrolases and beta-glucosidases to increase the level or extent of degradation and to fermentation of the resulting sugars to generate an organic substance such as an alcohol, preferably ethanol, which may be used as a biofuel.

Description of the Related Art

Efficient enzymatic conversion of crystalline polysaccharides is crucial for an economically and environmentally sustainable bioeconomy, but remains unfavourably inefficient.

The transition to a more environmental friendly economy has spurred research on enzymes capable of efficiently degrading recalcitrant carbohydrates, such as cellulose and chitin (FIG. 1A), for the production of biofuels (Himmel et al., 2007, Science 315: 804). Cellulose is the most abundant organic molecule on the earth and offers a renewable and seemingly inexhaustible feedstock for the production of fuels and chemicals. Chitin is a common constituent of fungal cell walls, shells of crustaceans and exoskeletons of insects. It is the second most abundant polymer in nature and each year more than one billion tons of chitin are produced in the biosphere, mainly by insects, fungi, crustaceans and other marine organisms. Chitin is abundantly available as a by-product from aquaculture, one of the fastest growing bioproduction industries on earth.

The conversion of cellulosic feedstocks into ethanol has the advantages of the ready availability of large amounts of feedstock, the desirability of avoiding burning or land filling the materials and the cleanness of the ethanol fuel. Wood, agricultural residues, herbaceous crops and municipal solid wastes have been considered as feedstocks for ethanol production. These materials primarily consist of cellulose, hemicellulose and the non-polysaccharide lignin. Once the cellulose is converted to glucose, the glucose is easily fermented by yeast into ethanol.

A variety of microorganisms exist for fermenting the products of hydrolysis of polysaccharides to yield desirable end products such as alcohol. Selection of appropriate microorganisms allows the products of hydrolysis of cellulose, chitin and other polysaccharides to be fermented to yield useful products, such as alcohol.

The predominant polysaccharide in the primary cell wall of biomass is cellulose, the second most abundant is hemicellulose and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Bacteria and fungi have evolved complex enzymatic systems enabling their growth on plant material rich in cellulose, but these organisms typically require weeks, months or even years to decompose a fallen log or a tilled corn stalk. Likewise, microorganisms contain enzymatic systems for degrading chitin. Bacterial chitinase helps to provide a carbon source for bacterial growth. Insects produce chitinase to digest their cuticle at each molt. In plants, chitinase is thought to provide a protective role against parasitic fungi. For chemical or fuel production from these same cellulose- and chitin-containing materials, industry requires affordable chemical or enzymatic systems that can do the job in hours or in days.

Traditionally, enzyme systems capable of degrading such carbohydrates were considered to consist of two types of hydrolytic enzymes called glycoside hydrolases: endo-acting enzymes that cut randomly in the carbohydrate chain and processive exo-acting enzymes (chito- or cellobiohydrolases), which degrade the polymers from chain ends (FIG. 1B). Although this model is generally accepted, it remains difficult to understand how, e.g., an endoglucanase would be capable of pulling a single polysaccharide chain out of its crystalline environment and forcing the chain productively into its active site cleft (FIG. 1B).

Ever since cellulases caught the interest of biochemists, there have been speculations about the possible existence of a substrate-disrupting factor that could make the crystalline substrate more accessible to hydrolytic enzyme (Reese et al., 1950, J Bacteriol. 59: 485). Recently, it was discovered that microorganisms that breakdown chitin indeed produce a protein that increases substrate accessibility and potentiates hydrolytic enzymes (Vaaje-Kolstad et al., 2005, J. Biol. Chem. 280: 28492; FIGS. 1C and 1D). The first example was a single-domain protein called CBP21 (CBP for Chitin-Binding Protein) produced by the chitinolytic bacterium Serratia marcescens. This protein has been classified as carbohydrate-binding module (CBM) and belongs to family CBM33 as defined by the CAZy nomenclature (Boraston et al., 2004, Biochem. J. 382: 769, Henrissat, 1991, Biochem. J. 280 (Pt 2): 309). Another example concerns two CBM33-containing proteins from Thermobifida fusca, called E7 and E8, which potentiate chitin hydrolysis by chitinase and cellulose hydrolysis by cellulases (Moser et al., 2008, Biotechnol. Bioeng. 100(6): 1066-77). Like CBP21, E7 is a single domain protein only comprising a CBM33 domain. E8 is a three-domain protein, meaning that it carries two domains in addition to a CBM33 domain.

It has recently been shown that proteins presently classified as family 61 glycoside hydrolases (GH61) in the CAZy nomenclature act synergistically with cellulases (Harris et al., 2010, *Biochemistry* 49: 3305) and are structurally similar to CBM33 proteins (Harris et al., 2010, supra; Karkehabadi et al., 2008, *J. Mol. Biol.* 383: 144; FIG. 1E). While CBM33 and GH61 have little sequence similarity, the structural similarity is evident (FIGS. 1D and 1E), including a diagnostic fully conserved arrangement of the N-terminal amino group, an N-terminal histidine and one other histidine residue (FIG. 1F; Karkehabadi et al., 2008, supra) forming a promiscuous metal-binding site (see below). On the basis of available literature data, including a recent comprehensive study of several GH61 proteins, it seems highly unlikely that GH61 proteins are endoglucanases, as originally thought (Harris et al., 2010, supra). Like CBM33 proteins, GH61 proteins do not have a substrate-binding cleft or pocket, nor do they possess a characteristic arrangement of acidic amino acids that could indicate a glycoside hydrolase activity. Instead, both types of proteins show an almost flat substrate-binding surface (FIGS. 1D and 1E; Harris et al., 2010, supra; Vaaje-Kolstad et al., 2005, *J. Biol. Chem.* 280: 11313). All in all, these results and observations show that CBM33 and GH61 proteins have similar functions, i.e., potentiating the efficacy of known hydrolytic enzymes (glycoside hydrolases) acting on crystalline polysaccharides. Furthermore, these results and observations strongly suggest that these proteins do so employing the same type of mechanism. So far, this mechanism has remained elusive.

The present invention provides methods of degrading or hydrolyzing a polysaccharide, such as chitin or cellulose, comprising contacting said polysaccharide with an oxidohydrolytic enzyme in the presence of at least one reducing agent and at least one divalent metal ion.

SUMMARY OF THE INVENTION

The present invention relates to methods of degrading or hydrolyzing a polysaccharide comprising contacting said polysaccharide with one or more oxidohydrolytic enzymes, wherein said degradation or hydrolysis is carried out in the presence of at least one reducing agent and at least one divalent metal ion.

The present invention also relates to methods of producing soluble saccharides, wherein said method comprises degrading or hydrolyzing a polysaccharide by the method defined above, wherein said degradation or hydrolysis releases said soluble saccharides and optionally isolating said soluble saccharides.

The present invention also relates to methods of producing an organic substance, comprising the steps of: (i) degrading or hydrolyzing a polysaccharide by the method defined above to produce a solution comprising soluble saccharides; (ii) fermenting said soluble saccharides, to produce said organic substance as the fermentation product; and optionally, (iii) recovering said organic substance.

The present invention also relates to a process for producing a fermentation product, comprising: (a) saccharifying a cellulosic material with an enzyme composition comprising an endoglucanase, a cellobiohydrolase, a beta-glucosidase, a GH61 polypeptide having cellulolytic enhancing activity, and a CBM33; (b) fermenting the saccharified cellulosic material with one or more fermenting microorganisms to produce the fermentation product; and (c) recovering the fermentation product from the fermentation.

BRIEF DESCRIPTION OF THE FIGURES

FIG. 1A shows repetitive disaccharide units in cellulose and chitin. FIG. 1B shows a schematic representation of the degradation of chitin or cellulose by endo-acting (top) and (processive) exo-acting glycoside hydrolases (bottom). FIG. 1C shows the effect of CBP21 on chitinase efficiency; the chitinase is chitinase C (ChiC), a family 18 endochitinase from *S. marcescens* (data from Vaaje-Kolstad et al., 2005, *J. Biol. Chem.* 280: 28492). FIG. 1D shows the crystal structure of CBP21 (Vaaje-Kolstad et al., 2005, *J. Biol. Chem.* 280: 11313). The side chains of the conserved histidine residues on the flat binding surface are shown in stick representation. FIG. 1E shows the crystal structure of a GH61E from *Thielavia terrestris* (Harris et al., 2010, *Biochemistry* 49: 3305). The side chains of the conserved histidine residues on the binding surface are shown in stick representation. FIG. 1F shows a detailed view of the conserved arrangement of the two histidines and the N-terminal amino group in CBP21 (dark grey) and GH61E (light grey), superimposed using PyMol. FIGS. 1D, 1E, and 1F were generated using PyMol.

FIG. 2A shows a MALDI-TOF MS spectrum showing oxidized soluble chitooligosaccharides generated by CBP21 acting on beta-chitin whiskers. This represents the very first time that such oxidized products were detected. FIG. 2B shows a chitin chain with a GlcNAcA unit. FIG. 2C shows 2.0 mg/mL beta-chitin treated with 1.0 µM CBP21 in the presence (left vial) or absence (right vial) of 1.0 mM ascorbic acid. After the incubation with or without ascorbic acid, the tubes were treated in an identical manner: They were shaken and then left for one minute for the chitin material to settle/sediment. The figure shows that the disrupted material in the left vial sediments much more slowly. This figure shows the enormous potential of CBP21 in disrupting crystalline chitin when applied under optimal conditions, i.e., in the presence of a reducing agent and a divalent metal ion. FIG. 2D shows a MALDI-TOF MS spectrum of products obtained after incubating beta-chitin (2.0 mg/mL) with 1.0 µM AnCDA (an overexpressed and purified chitin deacetylase from *Aspergillus nidulans*), 1.0 µM CBP21 and 1.0 mM ascorbic acid for 16 hours, showing oxidized deacetylated chitooligosaccharides (all major products contain two acetylated sugars). A control reaction without CBP21 did not yield soluble products (results not shown). FIG. 2E shows a MALDI-TOF MS spectrum of products obtained after incubating beta-chitin (2.0 mg/mL) with 1.0 µM AnCDA and 0.5 µM ChiC for 8 hours, showing deacetylated chitooligosaccharides (all major products contain one acetylated sugar). MS peaks are labelled by observed atomic mass and the degree of polymerization (DP) of the oligosaccharide. Labels always refer to the peak of highest intensity in the respective cluster (which comprises several adducts; see FIGS. 3A-3D). "ox" indicates the presence of a GlcNAcA at the chain end opposite to the non-reducing end. Asterisks indicate a deacetylated product. 100% relative intensity represents $2.5 \times 10^4$, $1.1 \times 10^3$ and $5.4 \times 10^4$ arbitrary units (a.u.), in FIGS. 2A, 2D, and 2E, respectively. See FIGS. 3A-3D for additional experiments for product verification.

FIG. 3A shows GlcNAcA containing products of CBP21 degraded beta-chitin are in equilibrium with the 1,5 δ-lactone and at low pH this equilibrium should become observable (Pocker & Green, 1973, *J. Am. Chem. Soc.* 95: 113). A sample with hexameric products was adjusted to pH~3.0 with acetic acid and incubated for four hours at room temperature. The sample was then analyzed by MALDI-TOF MS. The spectrum clearly shows both the acid form and the 1,5 δ-lactone which differ by 18 atomic mass units (amu), representing a water molecule. The equilibrium between the two forms will eventually lead to exchange of both oxygens added during the reaction with oxygens from solvent water. Indeed when product samples obtained after carrying out the reaction in $H_2^{18}O$ (see Examples) were adjusted to low pH, we observed not only a lactone and an acid showing a mass increase of 2 amu compared to reactions performed in $H_2^{16}O$, but also, after some time, an acid showing a mass increase of 4 amu (results not shown). FIG. 3B shows details of the mass spectrum for $DP6_{ox}$. The fact that the mass difference between $Na^+$ and $K^+$ corresponds to the mass of an oxygen atom could complicate interpretation. However, the similar ratios between the single sodium and potassium adducts and their corresponding sodium salt of sodium/potassium adduct (often observed for sugar acids) indicate that the product indeed is an oxidized hexamer. A second verification of the identity of the products observed by MALDI-TOF MS was done by adding LiCl to a final concentration of 33 mM to the sample before MALDI-TOF MS analysis to generate new diagnostic adducts. FIG. 3C shows products corresponding to the Li-adduct of the acid and the Li-adduct of the Li-salt of the acid were observed, thus confirming the identity of Na- and K-adducts observed in FIG. 3B. Peaks in all MALDI-TOF MS spectra are labelled according to their observed atomic mass and the degree of polymerization (DP) of the oligosaccharide. "ox" stands for oxidized. FIG. 3D shows superposed PSD spectra for the hexamer fraction obtained upon CBP21 treatment of beta-chitin in $H_2^{16}O$ (black) and $H_2^{18}O$ (grey). Inserts provide detailed views of parts of the spectrum. The data show that the Y-ions differ by 2 amu, whereas the B ions show identical masses regardless of the type of water used. The data are fully compatible with the chemical structure shown above the mass spectrum and show that the heavy oxygen atom is introduced at the oxidized reducing end. Note that the chemical structure shown has been simplified for the purpose of clarity: most hydroxyl groups as well as C6 are lacking. 100% relative intensity represents $4.6 \times 10^4$, $1.1 \times 10^4$, $0.8 \times 10^3$ and $1.8 \times 10^4$ a.u. in FIGS. 3A, 3B, 3C, and 3D, respectively.

FIG. 5A shows after 4 days of incubation of 2 mg/mL beta-chitin with 1.0 μM CBP21 and 1.0 mM ascorbic acid at pH 8.0, soluble products are dominated by even numbered short oligosaccharides with acidic reducing ends. Due to the low solubility of chitin oligosaccharides longer oligosaccharides are not observed (see Examples for the detection of longer products). FIG. 5B shows each acidic oligosaccharide species was observed as H-, Na- and K-adducts and Na- and K-adducts of the acidic oligosaccharide Na-salt. 100% relative intensity represents $3.5 \times 10^3$ a.u.

FIG. 6A shows a typical product spectrum showing the periodicity of even and odd numbered products that was also observed in the MALDI-TOF MS analysis (e.g., FIG. 2D and FIGS. 5A and 5B). Note that the alpha- and beta-anomers of non-oxidized oligosaccharides would be separated under these chromatographic conditions. The fact that only single peaks are observed confirms the modification of the reducing end. Peak identities were determined using MALDI-TOF MS (results not shown). FIG. 6B shows initial reaction velocities of CBP21 mediated chitin solubilization into hexameric products (full lines) or pentameric products (dashed lines) in the presence of 5.0 (grey lines, circular data points), 1.0 (dark grey lines, square data points) and 0.2 mM (black lines, triangular data points) ascorbic acid. These results show that the velocity of the reaction depends on the ascorbic acid concentration and that odd-numbered products are generated at a slower rate than even-numbered products.

FIGS. 7A and 7B show MALDI-TOF MS analysis of products detected after treating 2.0 mg/mL beta-chitin with 1.0 μM CBP21 and 1.0 mM ascorbic acid in Tris buffered $H_2^{18}O$ pH 8.0 (FIG. 7A) or in Tris buffered $H_2^{16}O$ pH 8.0 saturated with $^{18}O_2$ (FIG. 7B). All major products show a mass increase of 2 amu compared to reactions performed in solutions not containing isotope labeled water or molecular oxygen (see FIGS. 2A, 5A, and 5 5B). FIG. 7C shows adducts of the oxidized hexameric product shown in FIG. 7B. Note the small amount of non-isotope labeled product (indicated by the arrow), most likely resulting from the initial stage of the reaction where $^{16}O_2$ was still present (prior to $^{18}O_2$ saturation; see Materials and Methods). 100% relative intensity represents $6.8 \times 10^3$ and $2.0 \times 10^3$ a.u. in FIGS. 7A, 7B, and 7C, respectively. FIG. 7D shows a scheme for the enzymatic reaction catalyzed by CBP21. In the final oxidized product, one oxygen comes from molecular oxygen and one from water.

FIGS. 8A, 8B, 8C, and 8D show the effect of various potentially inhibiting factors on CBP21 activity. Sodium dithionite (SD) is a well known oxygen scavenger routinely used to create a oxygen free (anaerobic) environments for enzyme reactions. FIG. 8A shows a MALDI-TOF MS spectrum of a reaction mixture containing 2.0 mg/mL beta-chitin, 1.0 μM CBP21, 1.0 mM ascorbic acid and 10 mM sodium dithionite, incubated for 16 hours at 37° C. under anaerobic conditions (all vials were degassed with a Schlenk line). The spectrum shows baseline noise and no peaks of noteworthy intensity; in other words, there are no detectable amounts of CBP21 generated products. 100% relative intensity represents $0.9 \times 10^2$ a.u. FIG. 8B shows that the potentiating effect of CBP21 on chitinase (ChiC) is abolished by adding sodium dithionite (SD). Reaction conditions: 0.1 mg/mL beta-chitin, 0.1 µM ChiC, 1.0 mM ascorbic acid, 10 mM sodium dithionite, 1.0 µM CBP21, incubated for 16 hours at 37° C. under anaerobic conditions (all vials were degassed with a Schlenk line). End product quantities were analyzed by HPLC. FIG. 8C shows additional control experiments, showing product development during incubation of 0.45 mg/mL beta-chitin with 0.5 µM ChiC and 1 mM reduced glutathione (which has the same effect as ascorbic acid; see FIG. 11) in 20 mM Tris-HCl, pH 8.0. Further additions/conditions were 1.0 M CBP21 (standard conditions for maximum activity; dark line on filled diamonds), 1.0 µM CBP21 in a solution with reduced oxygen concentration obtained by gas exchange (line on plusses; note that the results displayed in FIG. 7C, showing the presence of $^{16}O_2$ even after extensive gas exchange in the Schlenk line, show that truly anaerobic conditions were not obtained), 1.0 µM CBP21 and 2 mM potassium cyanide, a well known $O_2$ mimic (line on filled squares) and no CBP21, no further additions (standard control experiment; line on filled circles). Addition of 2.0 mM sodium azide, a known inhibitor of heam proteins, did not inhibit CBP21 activity and the curves were similar to the curve on filled diamonds. CBP21 was also fully inhibited by oxyrace (Oxyrace Inc., Mansfield, Ohio), a bacterial oxidase that uses lactate as hydrogen donor in order to create an anaerobic environment (results not shown). FIG. 8D shows the production of $GlcNAc_3GlcNAcA$ (i.e., an oxidized tetramer) during a reaction of 0.45 mg/mL beta-chitin, 1.0 µM CBP21 and 1.0 mM reduced glutathione in 20 mM Tris-HCl pH 8.0 in the absence (line on filled diamonds) or presence (line on filled squares) of 2.0 mM potassium cyanide. This result shows that cyanide inhibits the oxidation reaction. Data shown in FIGS. 8B, 8C, and 8D are mean+/−SD (N=3); error bars (not visible for every point) indicate SD.

FIG. 10A shows that incubation of 1.0 µM $CBP21^{H114A}$ with 2.0 mg/mL beta-chitin, 1.0 mM ascorbic acid in 20 mM Tris, pH 8.0 for 16 hours at 37° C. did not lead to production of soluble oxidized oligosaccharides. 100% relative intensity represents $3.5 \times 10^4$ a.u. FIG. 10B shows product release upon degradation of 0.1 mg/mL beta-chitin with 0.5 µM ChiC in 1.0 mM ascorbic acid, 20 mM Tris, pH 8.0, in the presence or absence of $CBP21^{WT}$ (top grey line on filled triangles and dark grey line on filled diamonds, respectively) and in the presence of $CBP21^{H114A}$ (grey line on filled squares). The dark grey lines on filled circles show a reaction without CBP21 and without ascorbic acid. The data clearly show that His114 is essential for the function of CBP21 as $CBP21^{H114A}$ is unable to boost chitinase activity, even in the presence of ascorbic acid.

FIGS. 5 5A and 5B and 6 FIGS. 6A and 6B show that the activity of CBP21 is increased in the presence of ascorbic acid. Reductants such as reduced glutathione and Fe(II)SO$_4$ had similar effects on the kinetics of the degradation reaction (results not shown). 100% relative intensity represents $1.5 \times 10^4$ and $0.8 \times 10^3$ a.u. in FIGS. 11A and 11B, respectively.

FIG. 16A shows the production of non-oxidized dimers (top line with diamonds), oxidized trimers (line on triangles) and oxidized tetramers (obscured line on squares) produced during incubation of 0.45 mg/mL beta-chitin, 1.0 µM CBP21, 0.5 µM ChiC and 1.0 mM reduced glutathione in 20 mM Tris-HCl pH 8.0 (hydrolysis of oxidized oligosaccharides by ChiC produces only minimal amounts of oxidized dimers; the three products shown represent the large majority of oligomers produced under these conditions). After five hours, approximately 4.9% of the total sugars (theoretical number based on chitin concentration) are oxidized*. FIG. 16B shows production of oxidized sugars during incubation of 0.45 mg/mL beta-chitin, 1.0 µM CBP21 and 1.0 mM reduced glutathione in 20 mM Tris-HCl pH 8.0. The degree of oxidation was determined by rapid conversion of the treated chitin with a large dose of a chitinase cocktail followed by UHPLC detection of oxidized dimers (filled diamonds) and trimers (filled triangles), as described in the Materials and Methods section. The linear part of the reaction represents an oxidation rate of approximately 1 per minute. Maximum levels are reached after 2-3 hours and represent a degree of oxidation of 7.6% of the total sugars (theoretical number based on chitin concentration)*. Data in both panels are mean+/−SD (N=3); error bars (not visible for every point) indicate SD.

Figure 3A:
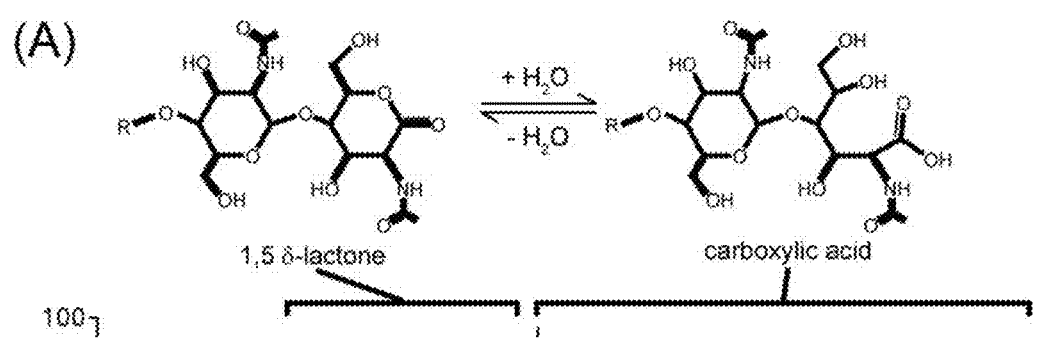
FIGS. 3A, 3B, 3C, and 3D show controls of product identities by MALDI-TOF.
Figure 3B:
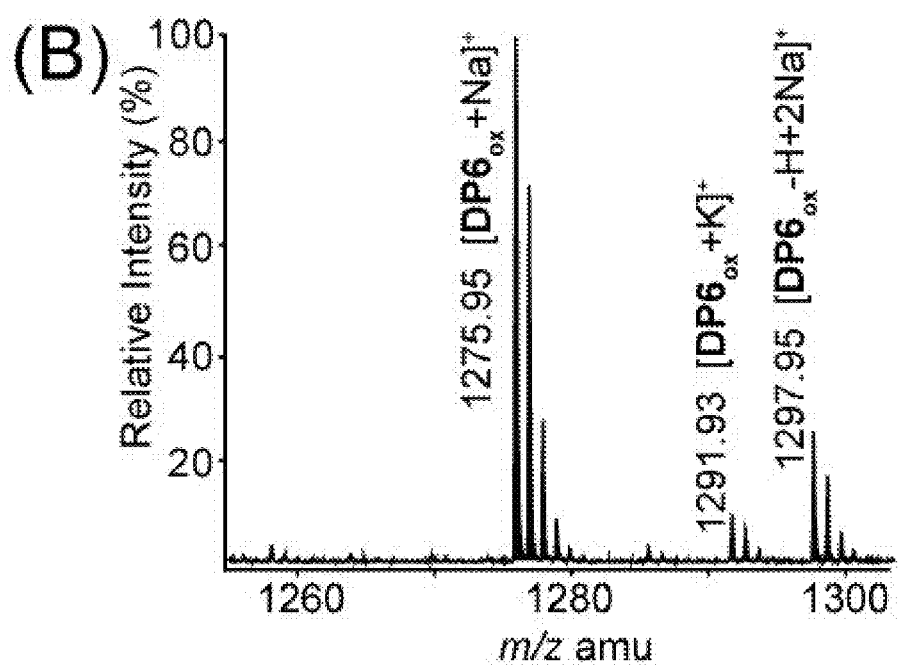
Figure 3C:
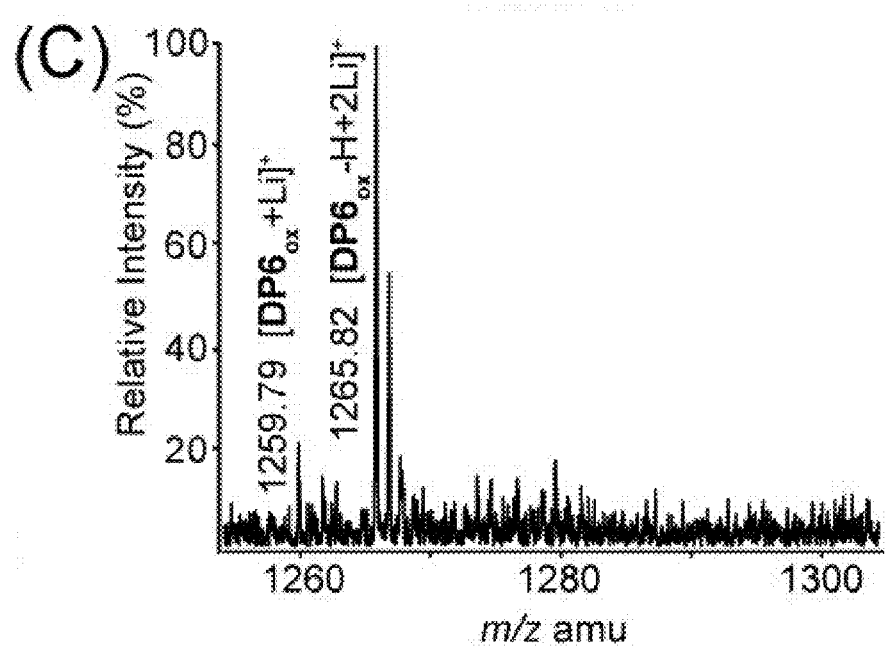
Figure 3D:
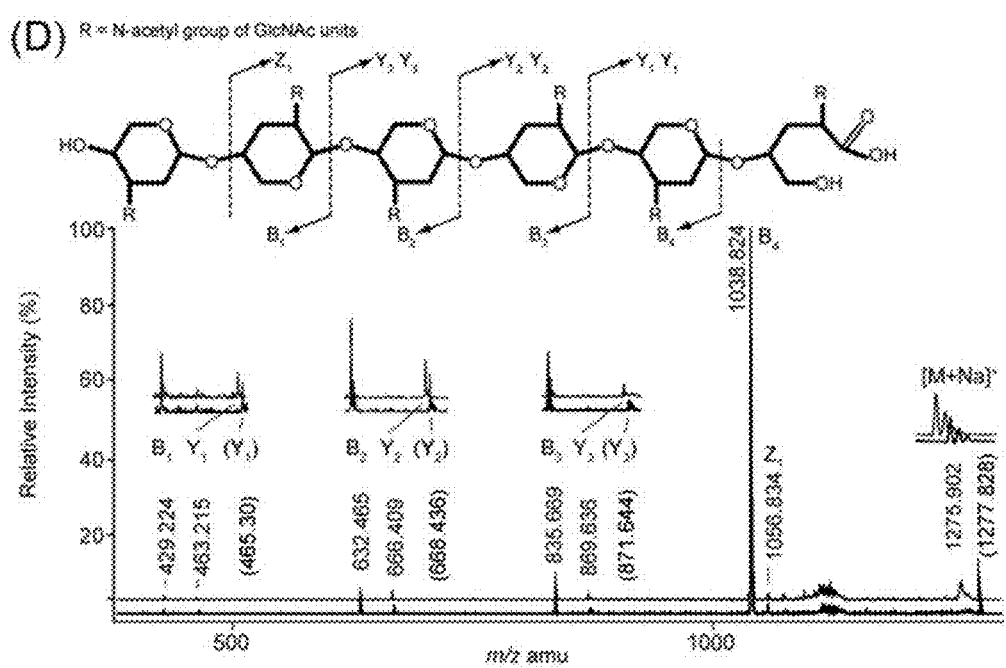

* The end concentrations of oxidized trimer and tetramer are 53 and 55 µM, respectively, giving rise to a total of 108 µM GlcNAcA. The molar concentration of GlcNAc in the solution is 2217 µM. Thus the degree of oxidation is 108/2217; in other words 4.9% of the sugars are GlcNAcA.  The rates calculated for oxidized dimer and oxidized trimer are 0.68 and 0.60 µM/min. When added, the rate of oxidized products generated is 1.28 µM/min and when taking the CBP21 concentration into account (1.0 µM), the rate of oxidohydrolysis is 1.28 per minute. * At the maximum levels reached, CBP21 has produced 93 µM and 75 µM oxidized dimer and oxidized trimer, respectively, which adds up to 168 µM GlcNAcA. The molar concentration of GlcNAc in the solution is 2217 µM. Thus the degree of oxidation is 168/2217; in other words 7.6% of the sugars are GlcNAcA.

Figure 17:
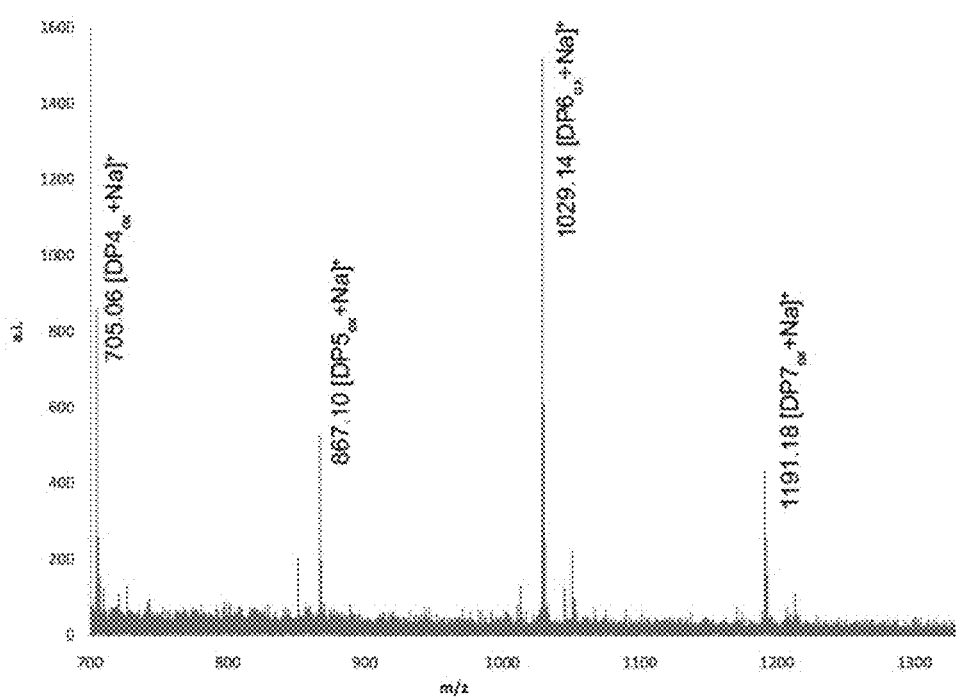

FIG. 17 shows MALDI-TOF MS analysis of soluble products generated by a CBM33 protein (1 µM CelS2) incubated with microcrystalline cellulose (2.0 mg/ml AVICEL®) in 20 mM Tris-HCl buffer pH 8.0 in the presence of 1.0 mM ascorbic acid (external electron donor), incubated for 20 hours, at 50° C. with horizontal agitation at 250 rpm. The main peaks are annotated with molecular weight and degree of polymerization (DP). All annotated peaks are Na-adducts of oxidized cellooligosaccharides (hence the subscript "ox"). More detailed analysis of the adduct clusters is shown in FIG. 18.

Figure 18:
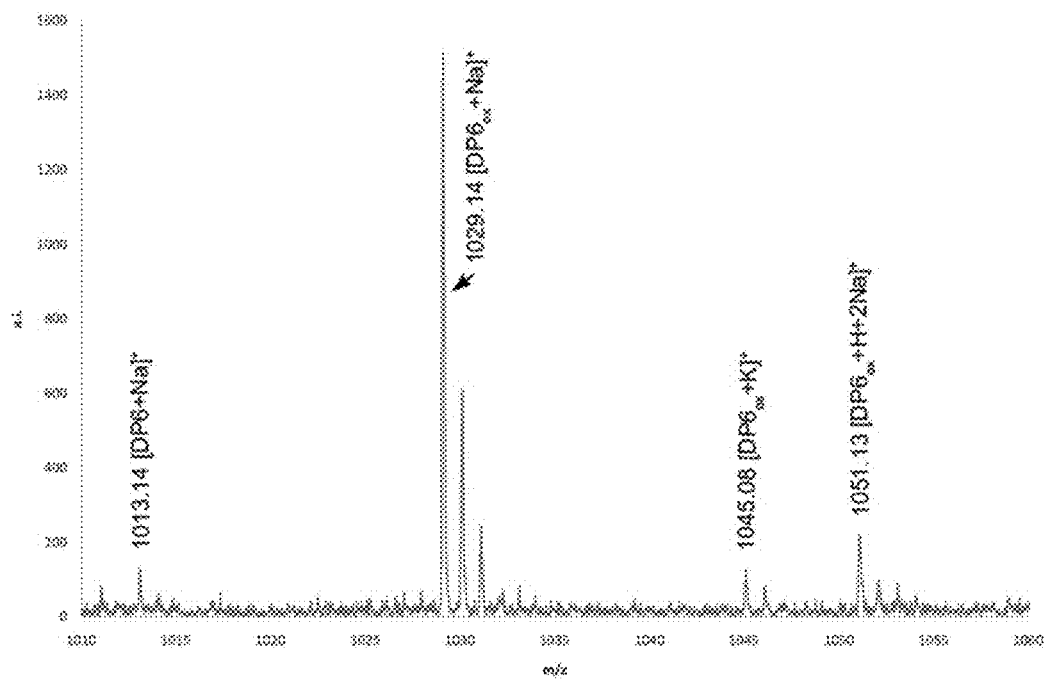

FIG. 18 shows MALDI-TOF MS analysis of the adduct cluster of the oxidized cellooligosaccharide hexamer generated by CelS2 (from the same sample as described in FIG. 17 legend). Peaks are annotated with molecular weight, degree of polymerization (DP); "ox" indicates oxidation. The spectrum shows small quantities of the native hexameric oligosaccharide (m/z=1013.14). The native oligosaccharides may arise from CelS2 substrate cleavage near the reducing end or liberation due to substrate disruption (see also FIG. 19). The dominant peak represents the Na-adduct of the oxidized hexamer (m/z=1029.14). Additionally, peaks representing the K-adduct of the oxidized hexamer (m/z=1045.08) and the Na-adduct of the Na-salt of the oxidized hexamer (m/z=1051.13) can also be observed.

Figure 19:
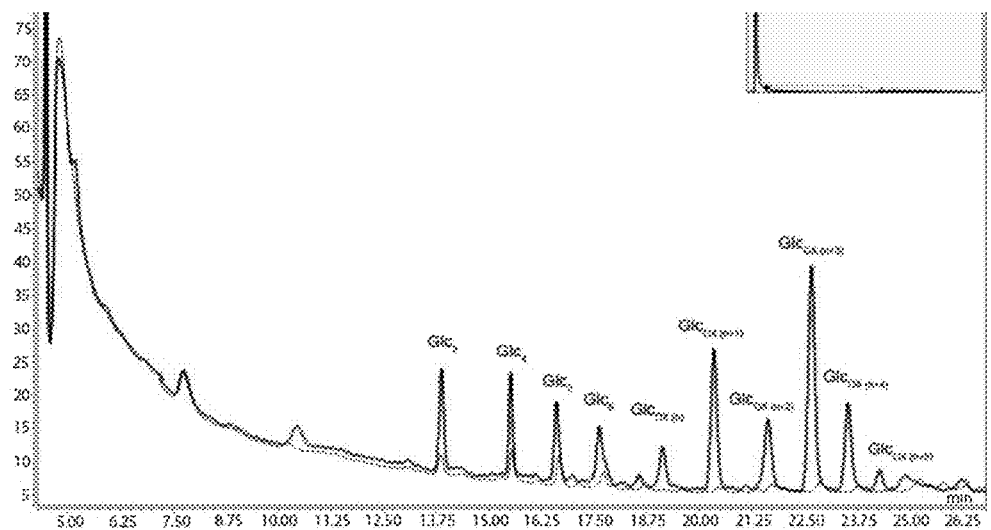

FIG. 19 shows HPAEC analysis of soluble products generated after incubation of 1.0 µM CelS2 with 10 mg/ml AVICEL® in 50 mM Tris-HCl pH 8.0, 1 mM $MgCl_2$, at 50° C., 900 rpm (horizontal agitation) in the presence ("pink", upper line) or absence ("dark purple", lower line) of 0.5 mM reduced gluathione (external electron donor). In the absence of reduced glutathione only small amounts of native cellooligosaccharides are observed (Glc3-Glc6) whereas larger amounts of both native cellooligosaccharides and oxidized cellooligosaccharides are observed when reduced glutathione is present. The DP of the oxidized cellooligosaccharides is indicated by n, where n=3 (the shortest labelled oxidized cellooligosaccharide has a DP of three (=n)). The presence of small amounts of native cellooligosaccharides was also seen in the control reaction without added CelS2 (10 mg/ml AVICEL® in 50 mM Tris-HCl pH 8.0 in the presence and absence of 0.5 mM reduced glutathione; results not shown). Thus, the substrate itself contains some shorter soluble non-oxidized cello-oligomers that are released upon incubation, even without CelS2. It is well known from the literature that AVICEL® has a relatively low degree of polymerization (Wallis et al., 1992, *Carbohydrate Polymers* 17: 103-110). Additionally, chain cleavage by CelS2 near the reducing end of a cellulose chain will give rise to such products. Peak annotation was performed by comparing the chromatogram with the chromatogram obtained for a chemically prepared mixture of oxidized cellooligosaccharides with lengths varying from DP1 to DP10. Note the periodicity of the oxidized cellooligosaccharides also observed by MALDI-TOF MS analysis (FIG. 17).

Figure 20:
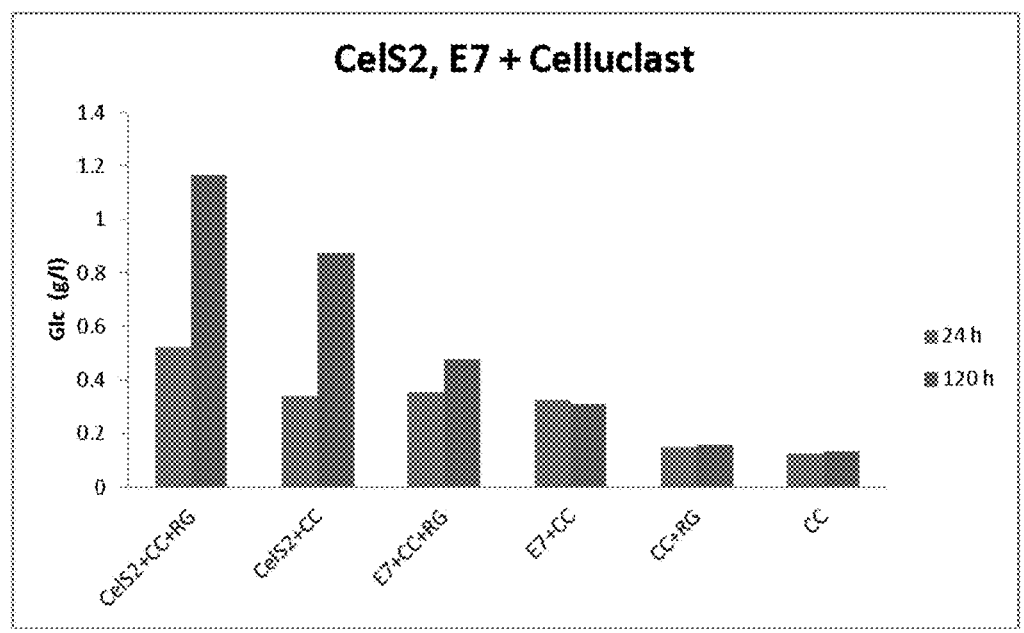

FIG. 20 shows total sugar (g/l) ([Glc]+cellobiose which is reported as [Glc]) after incubation of 1 µM CelS2 or E7 and 0.05 µl/ml CELLUCLAST™ ("CC") with 10 mg/ml filter paper for 24 or 120 hours in the presence or absence of 1 mM reduced glutathione ("RG"). Reactions were run in 50 mM Bis-tris/HCl pH 6.5, 1 mM $MgCl_2$, at 50° C. and 900 rpm (horizontal agitation). Control reactions containing the cellulosic substrate suspended in the same buffer as used for the enzyme assays gave no detectable signal for either glucose or cellobiose.

Figure 21:
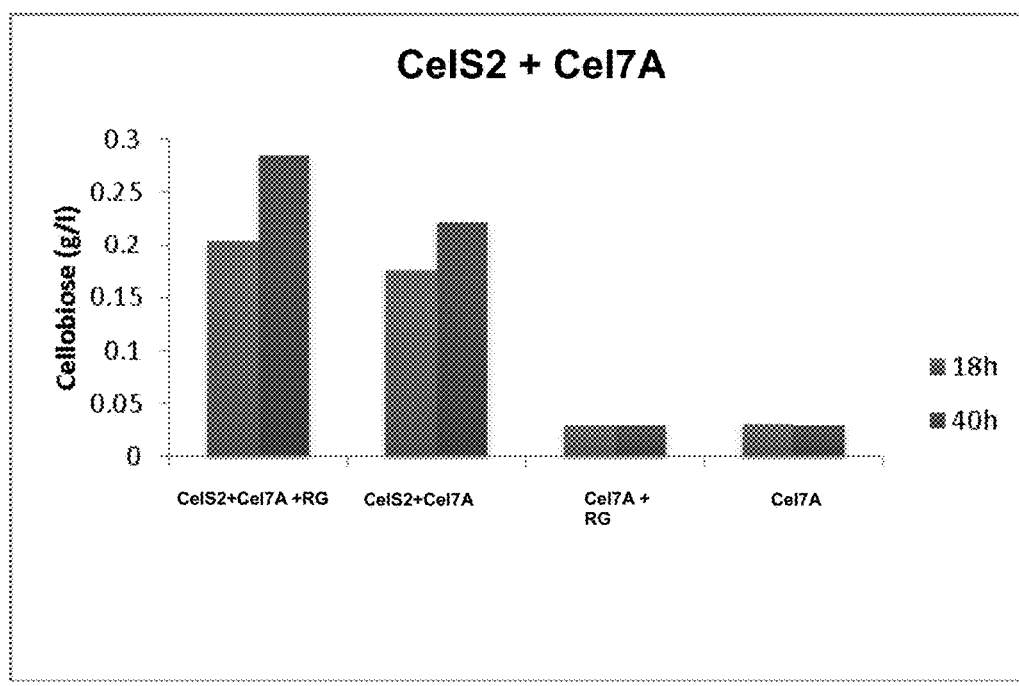

FIG. 21 shows cellobiose concentration (g/l) after 18 or 40 hours incubation of 1.0 µM CelS2 and 5 µg/ml Cel7A ("Cel7A") with 10 mg/ml filter paper in the presence or absence of 1 mM reduced glutathione ("RG"). These reactions were conducted in 50 mM sodium acetate pH 5.5, 1 mM $MgCl_2$, at 50° C., 900 rpm (horizontal incubation). Only the cellobiose concentration was quantified as the amount of glucose was minor (less than 5% of the total sugar). Control reactions containing the cellulosic substrate suspended in the same buffer as used for the enzyme assays gave no detectable signal for either glucose or cellobiose.

Figure 22:
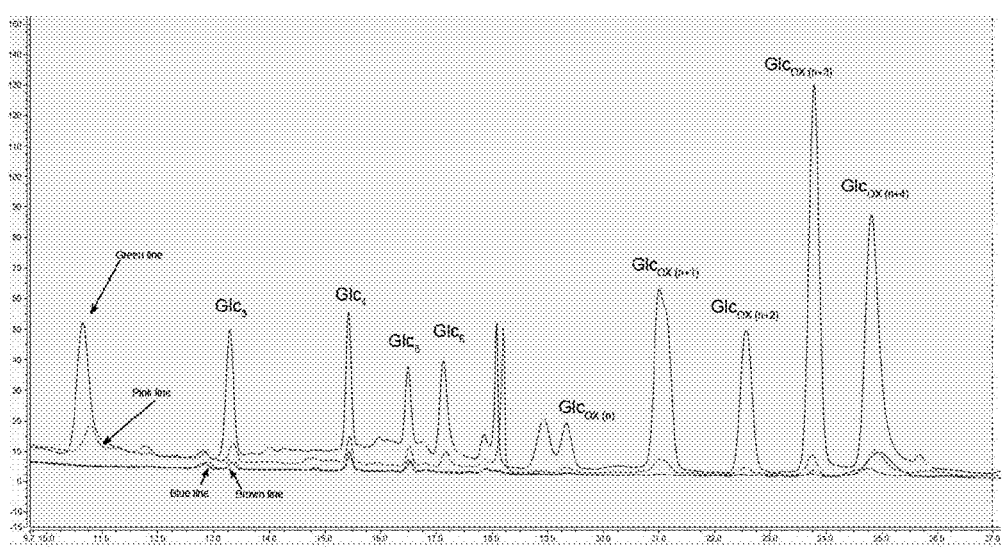

FIG. 22 shows HPAEC profiles showing products obtained after incubating CelS2 (1.0 µM) with microcrystalline cellulose (10 mg/ml AVICEL®) in 20 mM Tris-HCl buffer pH 8.0 in the presence of 1.0 mM ascorbic acid (external electron donor), in the presence (line labelled "pink", lower line) or absence (line labelled "green" line, upper line) of 2.0 mM potassium cyanide. Products were analyzed after incubation for 24 hours at 50° C. with vertical agitation at 900 rpm. The two remaining (lower) lines represent the same conditions as noted above (CelS2+ cyanide; "blue" line, buffer+cyanide; "brown" line), in the absence of ascorbic acid. The DP of the oxidized cellooligosaccharides is indicated (n=3), i.e., the shortest visible oxidized cellooligosaccharide has a DP of three (GlcNAc-GclNAc-GlcNAcA).

Figures 23A, 23B:
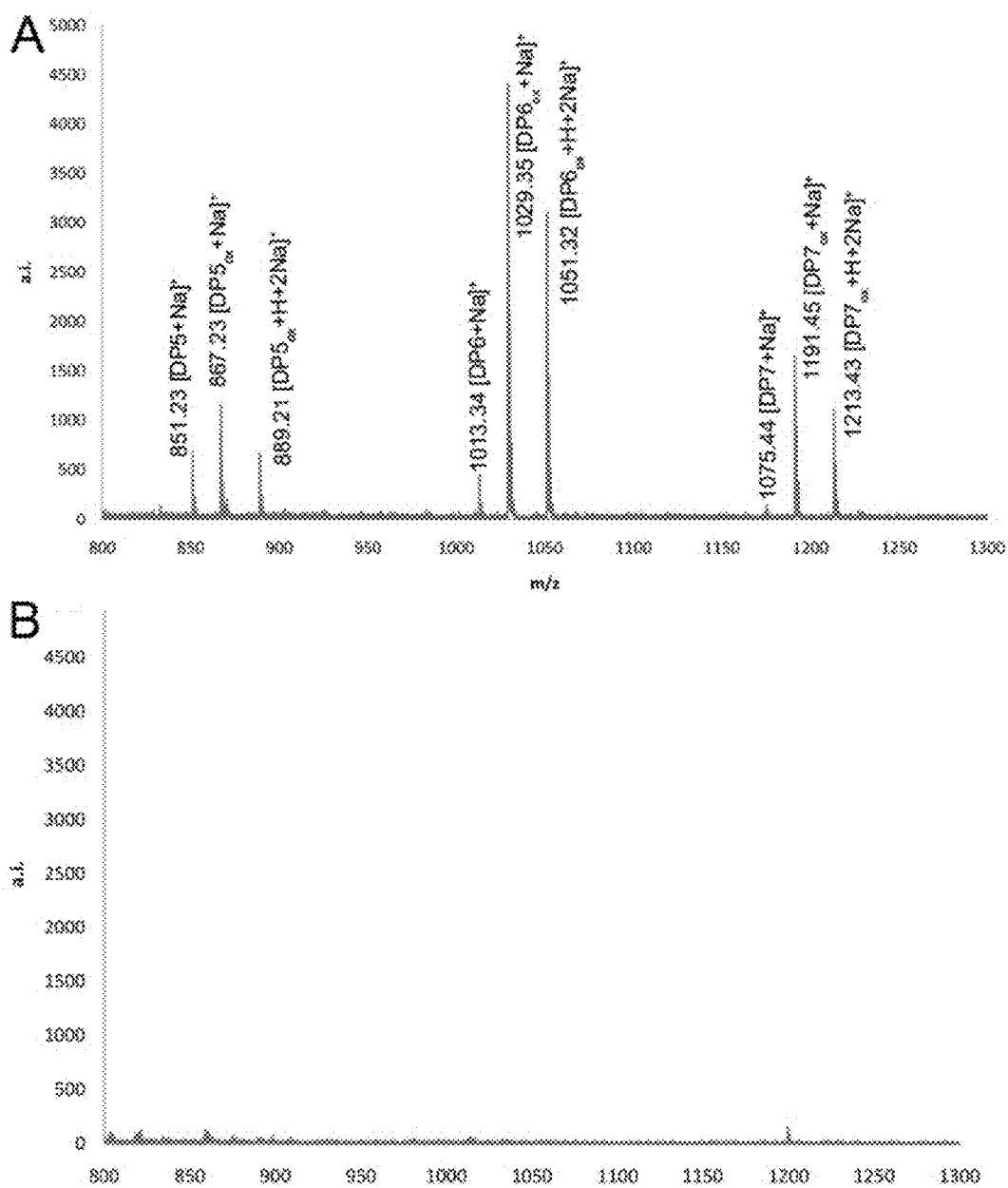

FIG. 23A shows MALDI-TOF MS analysis of soluble products generated by 1 µM CelS2-WT and FIG. 23B shows MALDI-TOF MS analysis of soluble products generated by 1 µM CelS2-H144 upon incubation with microcrystalline cellulose (10 mg/ml AVICEL®) in 20 mM Tris-HCl buffer pH 8.0 in the presence of 1.0 mM ascorbic acid (external electron donor), for 24 hours at 50° C. with horizontal agitation at 250 rpm. The main peaks are annotated with molecular weight and degree of polymerization (DP). All annotated peaks are Na adducts of native cellooligosaccharides, oxidized cellooligosaccharides (denoted "ox") or the sodium salts of oxidized cellooligosaccharides. Neither native nor oxidized cellooligosaccharides can be observed for the reaction with CelS2-H144 (FIG. 23B). The low intensity peak observed at 1199.55 m/z does not correspond to any oligosaccharide resulting from cellulose oxidation or hydrolysis and is likely to be a background component. The presence of native cellooligosaccharides is likely to be the result of the low mean DP of the substrate (AVICEL®; Wallis et al., 1992, *Carbohydrate Polymers* 17: 103-110); chain cleavage by CelS2 near the reducing end of a cellulose chain will also give rise to such products. See legend to FIG. 19 for additional discussion.

Figure 24:
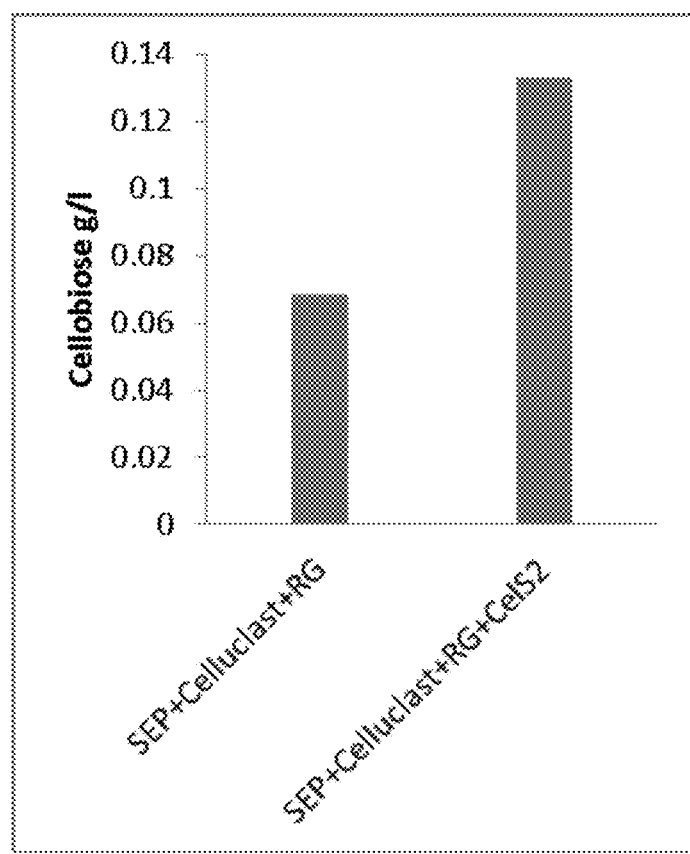

FIG. 24 shows the effect of CelS2 (1.0 µM) on the degradation of steam exploded saw dust from poplar (SEP; 2.0 mg/ml) by CELLUCLAST™ (0.016 µl/ml) in 20 mM sodium acetate buffer pH 5.5, 1.0 mM $MgCl_2$, 1.0 mM reduced glutathione (RG; external electron donor) incubated for 20 hours at 50° C., 250 rpm (horizontal agitation). The figure shows cellobiose release after 20 hours.

Figure 25:
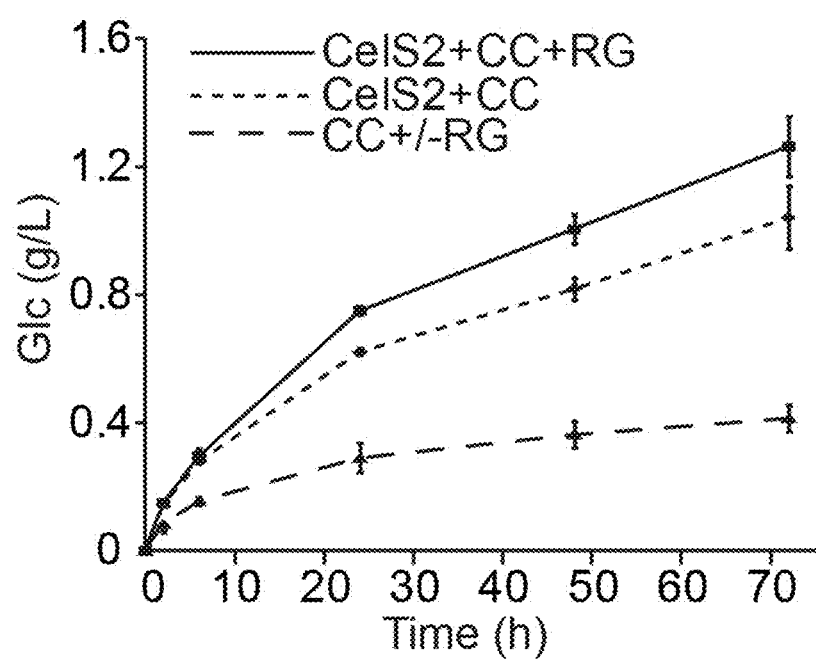

FIG. 25 shows degradation of high molecular weight filter paper cellulose (10 mg/ml) in 20 mM sodium acetate buffer pH 5.5 by 0.8 µg/ml CELLUCLAST™ (CC), in the presence or absence of 40 µg/ml CelS2 and 0.5 mM reduced glutathione (RG) as shown by the increase of soluble cellooligosaccharides (Glc and $Glc_2$; converted to total Glc) over time. In reactions where no CelS2 was present, 40 µg/ml purified BSA was added in order to maintain an identical protein load. Under these conditions, reactions with only CelS2 did not yield detectable amounts of Glc or $Glc_2$ (not shown). The chitin-active CBM33, CBP21, did not affect CC efficiency (not shown). RG had no effect in reactions with only CC; only one of the two overlapping curves is shown. Data are mean+/−SD (N=3); error bars indicate SD.

Figure 26:
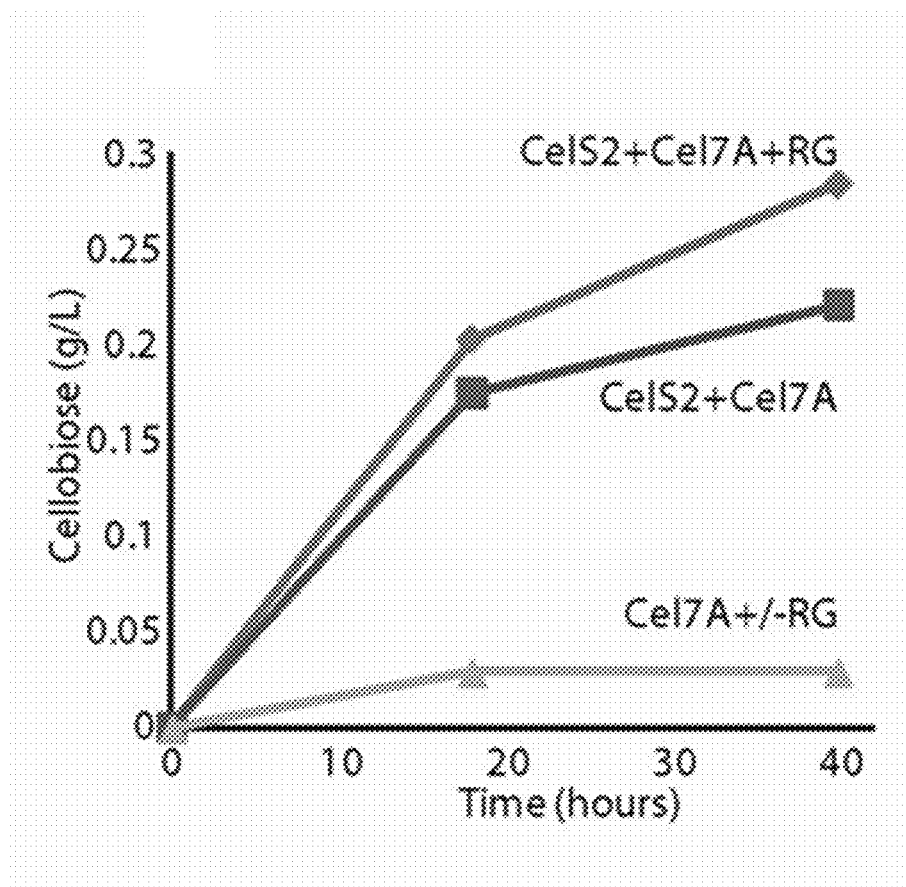

FIG. 26 shows degradation of cellulose in a reaction of 10 mg/ml filter paper with a combination of 40 µg/ml CelS2 (or 40 µg/ml BSA to compensate for the protein load in reactions without CelS2) and 5 µg/ml purified HjCel7A in 1 mM $MgCl_2$, 20 mM sodium acetate buffer, pH 5.5. By far the major products of these reactions are cellooligosaccharides released by the cellulases (whose activity is boosted by CelS2). In the case of HjCel7A, the main product is cellobiose and formation of this product is shown. RG, indicates the presence of a reductant, in this case reduced glutathione. The label "+/−RG" indicates that production curves for Cel7A alone (no CelS2 present) with and without RG were essentially identical. The reactions were run at 50° C.

Figure 27:
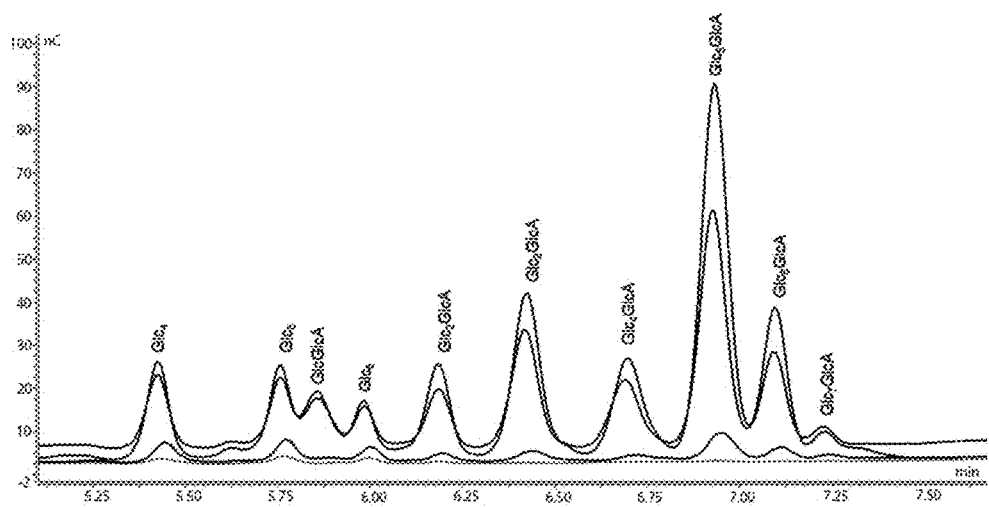

FIG. 27 shows HPAEC profiles of products obtained after incubating AVICEL® with the N-terminal CBM33 domain of CelS2 in the absence of reductant (bottom line) and in the presence of reduced glutathione (2nd from bottom line), gallic acid (darker of upper lines) or ascorbic acid (lighter of upper lines), which all serve as external electron donor. 1 µM of the N-terminal CBM33 domain of CelS2 was incubated with 10 mg/ml AVICEL® in the presence of 0.8 mM of one of the reductants, or in the absence of any reductant. Reactions were run in 50 mM succinate buffer pH 5.5, 1 mM $MgCl_2$, at 50° C. and 900 rpm (vertical agitation) for 20 hours.

Figure 28:
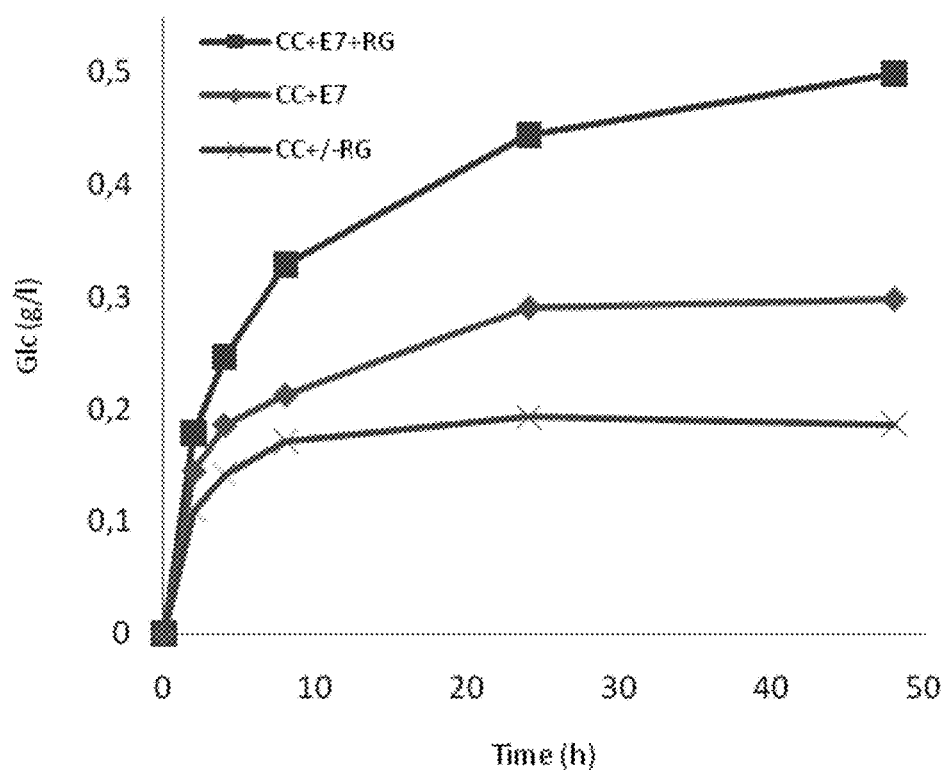

FIG. 28 shows total sugar (g/l) [Glc] (glucose and cellobiose reported as [Glc]) released after incubation of 0.08 µl/ml CELLUCLAST™ (CC) in the presence or absence of 1 µM E7 and 2 mM reduced glutathione (RG) as external electron donor with 2 mg/ml filter paper cellulose. Reactions were incubated in 20 mM sodium acetate buffer pH 5.5, 1 mM $MgCl_2$, at 50° C. and 900 rpm (horizontal agitation) for up to 50 hours. RG had no effect in reactions with only CC; only one of the two overlapping curves is shown. Control reactions with filter paper suspended in the same buffer as used for the enzyme assays, or E7 in absence of cellulases did not yield detectable amounts of Glc or $Glc_2$ (not shown).

Figure 29:
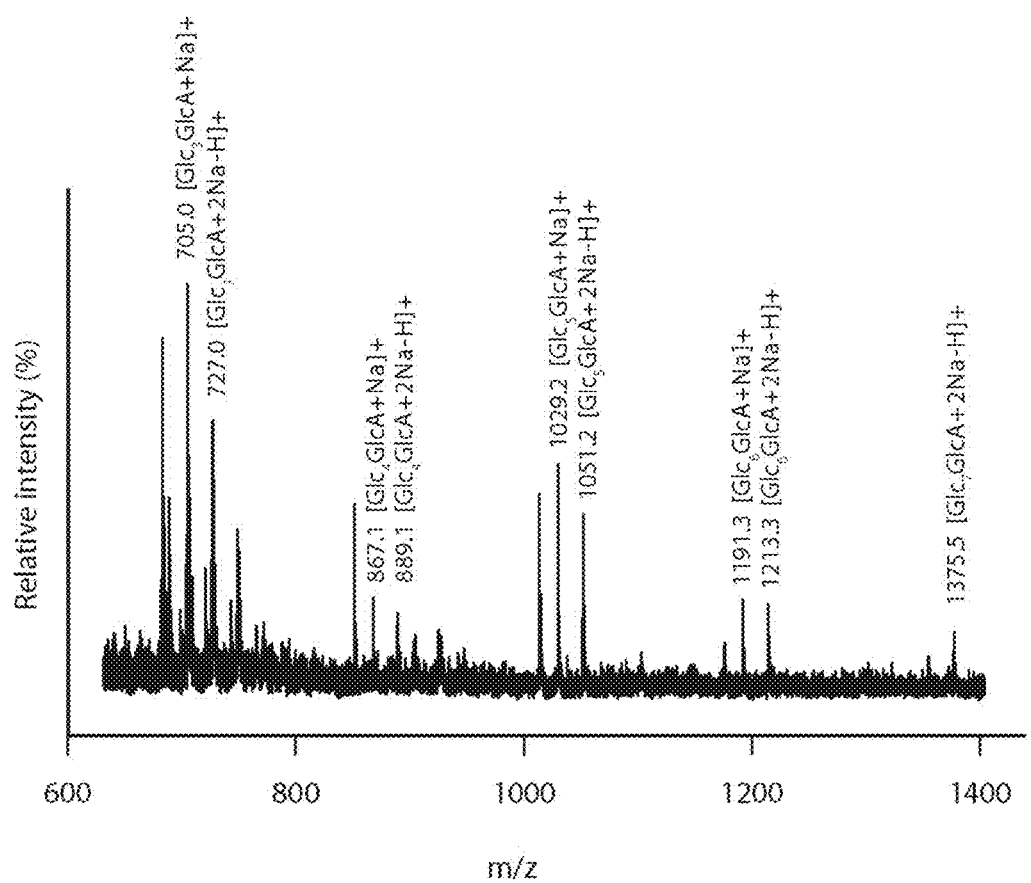

FIG. 29 shows MALDI-TOF MS analysis of soluble products generated by 1 µM E7 incubated with 10 mg/ml AVICEL® in 20 mM Tris-HCl buffer pH 8.0 and 1 mM $MgCl_2$ in the presence of 1 mM ascorbic acid as external electron donor, incubated for 20 hours, at 50° C. with vertical agitation at 900 rpm. The oxidized oligosaccharides ($Glc_{3-7}GlcA$) are observed as sodium adducts, and as sodium adducts of the oligosaccharide sodium salts, and annotated with their molecular weights (m/z); native cellooligosaccharides are also present but have been excluded from annotation. Such native oligosaccharides might be the result of CBM33 cleavage near the reducing end of the substrate.

Figure 30:
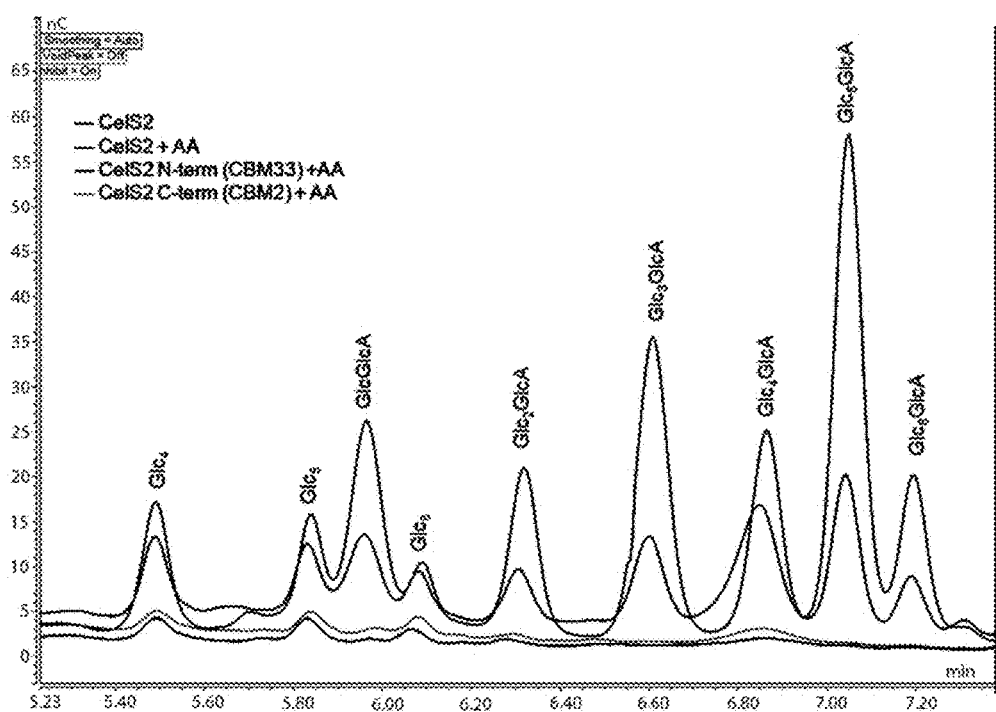

FIG. 30 shows HPAEC profiles of products generated by 1 µM full length CelS2 in the presence (top grey line) or the absence (bottom dark grey line) of 1 mM ascorbic acid (AA), or by the N-terminal CBM33 domain of CelS2 in the presence of AA (second top, dark line), or by the C-terminal CBM2 domain of CelS2 in the presence of AA (second bottom, dark line) upon incubation with 10 mg/ml AVICEL®. Products were analyzed after 20 hours of incubation in 20 mM ammonium acetate buffer pH 5.0, 1 mM $MgCl_2$ at 50° C. and 900 rpm (vertical agitation). The chromatogram is enlarged to emphasize the oxidized cello-oligosaccharides produced by the full length CelS2 and the N-terminal CBM33 domain of CelS2.

Figure 31:
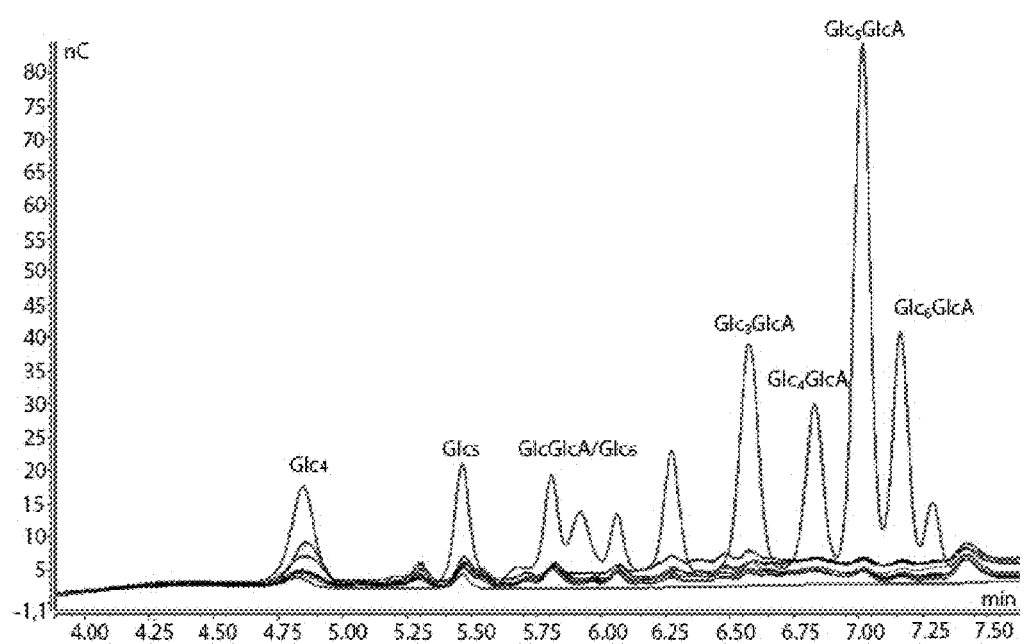

FIG. 31 shows reactivation of activity by adding metals to EDTA treated N-terminal CBM33 domain of CelS2. 0.8 mg/ml CBM33 was incubated with 400 µM EDTA for 3 hours at 20° C. This EDTA treated enzyme (40 µg/ml) was incubated with 10 mg/ml AVICEL® in 50 mM MES buffer pH 6.6 containing 1.7 mM reduced glutathione and one of 6 different metal ions (10 µM; $Mg^{2+}$, $Fe^{3+}$, $Zn^{2+}$, $Co^{2+}$, $Ca^{2+}$, $Cu^{2+}$). The remaining concentration of EDTA in these reaction mixtures was 20 µM. The superimposed HPAEC chromatograms show products released after 20 hours of incubation at 50° C. Only $Cu^{2+}$ (top, grey line) reactivated the enzyme under these conditions and when using these low metal concentrations.

FIG. 32A shows an alignment of GH61 sequences using ClustalW. The HjGH61A sequences were aligned to a profile created by structurally aligning TtGH61E and HjGH61B. N-terminal signal peptides present in the natural primary gene products were removed from the sequences prior to producing the alignment. FIG. 32B shows the structural superposition of TtGH61E and HjGH61B. The side chains of six conserved active site and surface residues each shaded in grey in the alignment of FIG. 32A are shown in dark grey in FIG. 32B. An insertion present in HjGH61B is shown in the shaded section in FIG. 32A and in the 3 turn helix in FIG. 32B.

FIG. 33A shows the structure of CBP21. FIG. 33B shows a comparison of the structure of CBP21 with a structural model of E7. FIG. 33C shows a comparison of the structure of CBP21 with the structure of TtGH61E Note the similarity between E7 and TtGH61E (Met and Val at positions 207 and 161 respectively are both hydrophobic residues; the corresponding residue in CBP21, T183, is more polar). CBP21 lacks a histidine (CBP21 has D182), a tyrosine (CBP21 has F187) and a glutamine (CBP21 has E60) that are conserved in the two GH61s shown. Residues are numbered as they appear in the primary gene product, i.e., a protein with an N-terminal signal peptide. Mature correctly processed proteins start with a histidine, which would then be histidine 1 (such as shown in the alignment of FIG. 32A). H28, H37 and H19 correspond to this histidine 1 in FIGS. 33A, 33B, and 33C, respectively.

Figure 34:
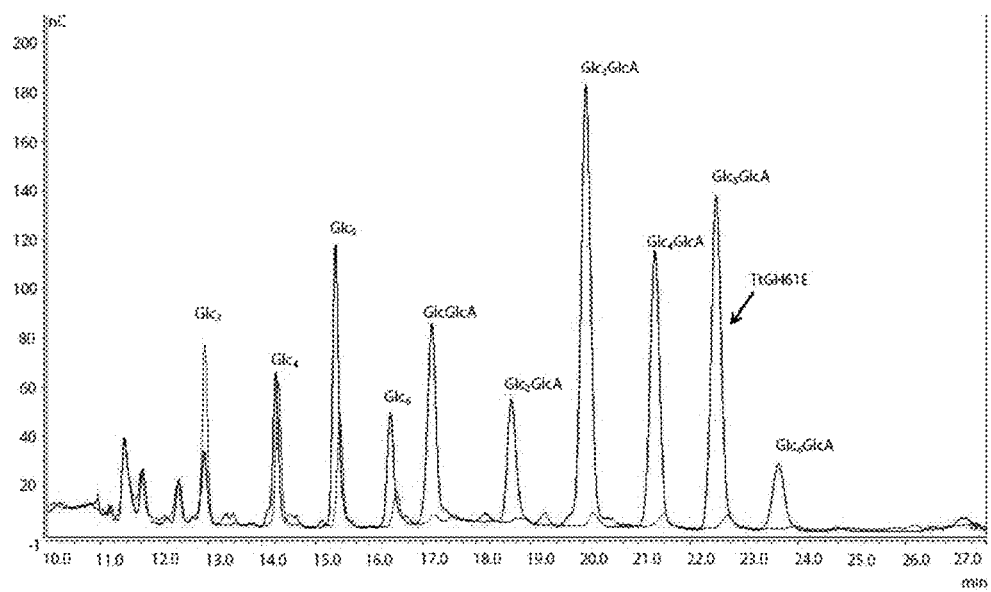

FIG. 34 shows HPAEC chromatograms for production of oligosaccharides from microcrystalline cellulose (AVICEL®) by TtGH61E (upper curve, with higher peaks) and TaGH61A (lower curve). GH61 proteins (140 µg/ml) were incubated at 50° C. with 10 mg/ml AVICEL® in 50 mM MES buffer pH 6.6 containing 2.4 mM ascorbic acid (a reductant) for 24 hours with horizontal agitation at 700 rpm.

Figure 35:
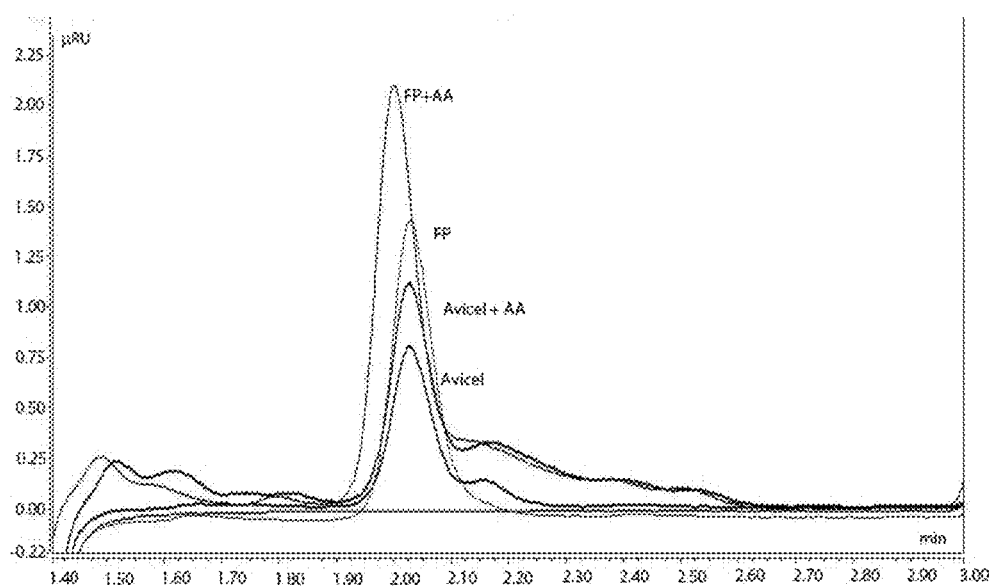

FIG. 35 shows chromatograms (Rezex RFQ-Fast Fruit H+ column) for production of glucose from AVICEL® and Filter Paper by CELLIC™ CTec2 (final concentration of added protein was 1.1 µg/mL) in the presence or absence of ascorbic acid. The enzymes were incubated at 50° C. with 10 mg/ml substrate (AVICEL® or filter paper) in 50 mM MES buffer pH 6.6 with or without 0.5 mM ascorbic acid for 24 hours with horizontal agitation at 700 rpm.

DETAILED DESCRIPTION OF THE INVENTION

Surprisingly, the inventors have now found that CBM33 and GH61 proteins as oxidohydrolases exploit molecular oxygen and water to introduce chain breaks on the surfaces of crystalline polysaccharides, i.e., on the surface of a solid phase, to open up the inaccessible polysaccharide material for hydrolysis by normal glycoside hydrolases. Although not wishing to be bound by theory it is believed that the carbohydrate chain is oxidized by molecular oxygen and chain cleavage is accomplished by a concomitant hydrolysis (FIG. 7D). In view of this mechanism we refer to the enzymes as oxidohydrolases. However, these enzymes may alternatively be referred to herein as polysaccharide degrading enzymes (or simply enzymes) in view of their ability to effect or assist cleavage of glycosidic bonds in polysaccharides. Enzymatic cleavage of crystalline polysaccharides in a reaction dependent on reactive oxygen species has so far not been described.

These enzymes have flat surfaces that bind to the flat, solid, well-ordered surfaces of crystalline material and catalyze chain breaks. The chain break will result in disruption of crystalline packing and increased substrate accessibility, an effect that may be augmented by the modification of one of the new chain ends. At the cleavage point one of the new ends is a normal non-reducing end (indicated by R—OH in FIG. 7D). The other new end would have been a new reducing end if the cleavage had been performed by a normal glycoside hydrolase. However, in this case the product is different and the last sugar is oxidized to become 2-(acetylamino)-2-deoxy-D-gluconic acid (FIG. 7D). This novel "acidic chain end" will interfere with normal crystal packing because it will not have the normal chair conformation of the sugar ring and because it carries a charge. Effects on non-crystalline substrates are also possible.

Genes encoding these oxidohydrolases (such as genes encoding members of the CBM33 or GH61 families) are abundant in chitin- and cellulose-degrading microorganisms. As assessed by gene sequences, CBM33 and GH61 proteins are found both as single-domain proteins (i.e., consisting of a CBM33 or GH61 domain only) and as multi-domain proteins (i.e., consisting at least one more domain, often a domain that is putatively involved in substrate binding). When the CBM33 or GH61 domain containing proteins have more than one domain, the additional domains are usually coupled to the C-terminus of the CBM33 or GH61 domain because the N-terminus of the CBM33 or GH61 domain is essential for oxidohydrolytic activity. Knowledge of the mode of action of these enzymes has allowed their catalytic efficiency to be optimized to achieve more efficient enzymatic conversion of biomass into sugars which may be used for fermentation.

In view of the identification of the role of molecular oxygen in catalysis, it has now been found that the efficiency of the reaction can be improved by the addition of reductants that can act as electron donor and/or generate reactive oxygen species. In the presence of divalent metal ions reductants improve enzymatic conversion of recalcitrant polysaccharides.

Thus, in a first aspect, the present invention provides a method of degrading or hydrolyzing a polysaccharide comprising contacting said polysaccharide with one or more oxidohydrolytic enzymes, wherein said degradation or hydrolysis is carried out in the presence of at least one reducing agent and at least one divalent metal ion.

As referred to herein "degrading" said polysaccharide refers to degradation by disruption of the glycosidic bonds connecting the sugar monomers in the polysaccharide polymer.

The degradation of said polysaccharide is enhanced by the use of said reducing agents and metals relative to performance of said method without those means, thus the rate or degree of disruption of the glycosidic bonds that connect the sugar monomers is increased. This may readily be determined by measuring the product formation, e.g., at certain defined time points or by measuring the amount of undegraded polysaccharide substrate which remains, e.g., at certain defined time points. This can be carried out using methods that are well known in the art, based on, e.g., determination of liberated reducing sugars (Horn et al., 2004, *Carbohydrate Polymers* 56(1): 35-39 and references therein) or determination of liberated fragments, e.g., cellulose or chitin fragments, e.g., by quantitative analysis of chromatograms obtained upon High Performance Liquid Chromatography (Hoell et al., 2005, *Biochim. Biophys. Acta* 1748(2): 180-190). Preferably said measure of degradation is assessed in the presence of one or more relevant saccharolytic enzymes as described hereinafter.

If the rate of degradation (e.g., hydrolysis), i.e., the number of bonds disrupted (e.g., hydrolyzed) in a certain time period is greater when the substrate has been exposed to the oxidohydrolytic enzyme in the presence rather than absence of reducing agents and metal ions, then the rate of degradation is considered to be enhanced. Preferably the use of reducing agents and metal ions reduces the time taken for degradation (either complete or to the same level of partial degradation, e.g., when additional saccharolytic enzymes are used, see hereinafter) by at least 2, 3, 4, 5, 6, 7, 8, 9 or 10 fold. Alternatively expressed, the use of reducing agents and metal ions increases the rate of degradation by at least 2, 3, 4, 5, 6, 7, 8, 9 or 10 fold.

"Hydrolyzing" refers to the chemical reaction in which water reacts with a compound to produce other compounds and involves the splitting of a bond and the addition of the hydrogen cation and the hydroxide anion from the water. In the case of hydrolysis of polysaccharides glycosidic bonds are cleaved by hydrolysis. The hydrolysis of polysaccharides to soluble sugars is referred to as "saccharification". Hydrolysis of polysaccharides as referred to herein results in degradation of the polysaccharide into smaller polysaccharides, including oligosaccharides and saccharide monomers such as glucose.

Hydrolysis of the polysaccharide may be partial or complete. In the case of complete hydrolysis, complete saccharification is achieved, i.e., only soluble sugars (e.g., mono- and di-saccharides) remain. In partial hydrolysis, in addition to soluble sugars, larger oligosaccharides and polysaccharides remain. As described herein methods of the invention include methods in which only oxidohydrolytic enzymes are used for degradation or in which both oxidohydrolytic enzymes and saccharolytic enzymes are used for degradation. In the former case, preferably at least 0.05-10%, e.g., 0.05 to 5%, preferably 0.1 to 1% of the glycosidic bonds of the starting polysaccharide are degraded (i.e., disrupted, e.g., hydrolyzed) into oligosaccharides which may be separate from the polysaccharide substrate or may remain associated despite cleavage. In the latter case in which saccharolytic enzymes are also used, preferably at least 50% (especially preferably 60, 70, 80, 90, 95, 96, 97, 98, 99 or 100%) of the glycosidic bonds of the starting polysaccharide are degraded, e.g., hydrolyzed. Alternatively expressed, in the latter case, preferably at least 50% (especially preferably 60, 70, 80, 90, 95, 96, 97, 98, 99 or 100%) of the starting polysaccharide is hydrolyzed into mono- or di-saccharides.

In relation to cellulose, the level of degradation may be assessed by determining the increase in the level of cellobiose and/or glucose.

As referred to herein said "polysaccharide" is a polymeric carbohydrate structure, formed of repeating units (either mono- or di-saccharides) joined together by glycosidic bonds and having the general formula $(C_6H_{10}O_5)_n$, e.g., in which $40 \leq n \leq 3000$. Preferably said polysaccharide is at least partially crystalline, i.e., is in a crystalline form or has crystalline portions, i.e., a form or portion which shows a repeating, three-dimensional pattern of atoms, ions or molecules having fixed distances between the constituent parts.

Preferably said polysaccharide is cellulose, hemicellulose or chitin and may be in isolated form or may be present in impure form, e.g., in a cellulose-, hemicellulose- or chitin-containing material (i.e., a polysaccharide-containing material), which optionally may contain other polysaccharides, e.g., in the case of cellulose, hemicellulose and/or pectin may also be present.

By way of example, the cellulose-containing material may be stems, leaves, hulls, husks and cobs of plants or leaves, branches and wood of trees. The cellulose-containing material can be, but is not limited to, herbaceous material, agricultural residues, forestry residues, municipal solid wastes, waste paper and pulp and paper mill residues. The cellulose-containing material can be any type of biomass including, but not limited to, wood resources, municipal solid waste, wastepaper, crops and crop residues (see, for example, Wiselogel et al., 1995, in "*Handbook on Bioethanol*" (Charles E. Wyman, editor), pp. 105-118). Preferably the cellulose-containing material is in the form of lignocellulose, e.g., a plant cell wall material containing lignin, cellulose and hemicellulose in a mixed matrix.

In a preferred aspect, the cellulose-containing material is corn stover. In another preferred aspect, the cellulose-containing material is corn fiber, corn cobs, switch grass or rice straw. In another preferred aspect, the cellulose-containing material is paper and pulp processing waste. In another preferred aspect, the cellulose-containing material is woody or herbaceous plants. In another preferred aspect, the cellulose-containing material is bagasse.

"Cellulose" is a polymer of the simple sugar glucose covalently bonded by beta-1,4-linkages. Cellulose is a straight chain polymer: unlike starch, no coiling or branching occurs and the molecule adopts an extended and rather stiff rod-like conformation, aided by the equatorial conformation of the glucose residues. The multiple hydroxyl groups on the glucose from one chain form hydrogen bonds with oxygen molecules on the same or on a neighbour chain, holding the chains firmly together side-by-side and forming microfibrils with high tensile strength.

Compared to starch, cellulose is also much more crystalline. Whereas starch undergoes a crystalline to amorphous transition when heated beyond 60-70° C. in water (as in cooking), cellulose requires a temperature of 320° C. and pressure of 25 MPa to become amorphous in water.

Several different crystalline structures of cellulose are known, corresponding to the location of hydrogen bonds between and within strands. Natural cellulose is cellulose I, with structures $I_\alpha$ and $I_\beta$. Cellulose produced by bacteria and algae is enriched in $I_\alpha$ while cellulose of higher plants consists mainly of $I_\beta$. Cellulose in regenerated cellulose fibers is cellulose II. The conversion of cellulose I to cellulose II is not reversible, suggesting that cellulose I is metastable and cellulose II is stable. With various chemical treatments it is possible to produce the structures cellulose III and cellulose IV.

"Hemicellulose" is derived from several sugars in addition to glucose, especially xylose but also including mannose, galactose, rhamnose and arabinose. Hemicellulose consists of shorter chains than cellulose; around 200 sugar units. Furthermore, hemicellulose is branched, whereas cellulose is unbranched.

"Chitin" is defined herein as any polymer containing beta-(1-4) linked N-acetylglucosamine residues that are linked in a linear fashion. Crystalline chitin in the alpha form (where the chains run anti-parallel), beta form (where the chains run parallel) or gamma form (where there is a mixture of parallel and antiparallel chains), amorphous chitin, colloidal chitin, chitin forms in which part (e.g., up to 5, 10, 15 or 20%) of the N-acetylglucosamine sugars are deacetylated are all included within the definition of this term.

Other forms of chitin that are found in nature include copolymers with proteins and these copolymers, which include protein chitin matrices that are found in insect and crustacean shells and any other naturally occurring or synthetic copolymers comprising chitin molecules as defined herein, are also included within the definition of "chitin".

The term "chitin" thus includes purified crystalline alpha, beta and gamma preparations, or chitin obtained or prepared from natural sources, or chitin that is present in natural sources. Examples of such natural sources include squid pen, shrimp shells, crab shells, insect cuticles and fungal cell walls. Examples of commercially available chitins are those available from sources such as France Chitin, Hov-Bio, Sigma, Sekagaku Corp, amongst others.

As referred to herein "contacting" said polysaccharide with an oxidohydrolytic enzyme refers to bringing the two entities together in an appropriate manner to allow the catalytic properties of the enzyme to be effective.

The precise kinetics of the reaction between the oxidohydrolytic enzyme and the polysaccharide will depend on many factors, such as the type of polysaccharide to be degraded, the amount of enzyme present, the temperature and the pH. The type of polysaccharide and its degree of amorphousness will vary with the substrate source and isolation/purification process, but can be assessed, for example, by measuring the degree of crystallinity of the substrate (which is a method known in the art).

Taking these considerations into account one can determine appropriate incubation times and conditions to maximize degradation (e.g., hydrolysis with glycoside hydrolases). Exemplary methods are discussed below.

Thus, the polysaccharide and oxidohydrolytic enzyme are mixed together or contacted with one another to allow their interaction. This may simply involve directly mixing solutions of the different components or applying the enzyme to the polysaccharide-containing material.

As referred to herein "one or more" preferably denotes 2, 3, 4, 5 or 6 or more of the recited enzymes. When more than one of the enzymes is used they may be selected in line with the substrate to be used, e.g., to provide complementary or synergistic action. Thus, for example, oxidohydrolytic enzymes may be combined which are effective on different regions of the substrate, e.g., different crystal faces. Preferred combinations are described hereinafter.

As used herein an "oxidohydrolytic enzyme" is an enzyme which uses molecular oxygen or an activated form thereof ("reactive oxygen species") for cleavage of glucoside bonds in polysaccharides, preferably chitin or cellulose. The newly generated chain ends are one normal non-reducing end and an oxidized "acidic" end that, in the case of chitin is a 2-(acetylamino)-2-deoxy-D-gluconic acid and in the case of cellulose is a gluconic acid.

Preferably said enzyme has a metal binding site and requires the presence of a divalent metal ion for full activity. The structural environment of this metal ion is diagnostic (and unifying) for the CBM33 and GH61 enzymes. The metal is bound by at least three ligands that are fully conserved in both families: (1) a histidine that is in position 1 of the mature protein (i.e., the N-terminal residue of the protein after the signal peptide for secretion has been cleaved off); (2) the N-terminal amino group of the mature protein; and (3) another histidine residue that is fully conserved.

Oxidohydrolases belonging to the CBM33 or GH61 family can be identified by analysis of gene sequences (and the corresponding predicted amino acid sequences of the gene products), using standard bioinformatic methods. For example one can use an existing multiple sequence alignment of CBM33 or GH61 enzymes, for example represented by a Hidden Markov Model, to search for homologous sequences in sequence databases. Sequences retrieved by such searches would be highly likely to be active oxidohydrolases. More certainty may be obtained by (1) checking that the gene encodes a protein with a signal peptide for secretion, using, e.g., the programme SignalP; (2) checking that the N-terminal residue after cleavage of the signal peptide (cleavage site to be predicted using, e.g., SignalP) is a histidine; (3) checking that there is another histidine in the protein sequence that aligns with a fully or almost fully (>90%) conserved histidine in the multiple sequence alignment; (4) using model-building by homology, using automated servers such as Swiss-Model, to check that this second histidine is likely to be located close to the N-terminus and the N-terminal histidine.

The skilled person can readily determine by experiment whether a protein is an oxidohydrolytic enzyme according to the above described definition by determining if it can cleave glucoside bonds and if this process becomes more effective in the presence of molecular oxygen, a reductant and a divalent metal ion. In addition, one may test whether the putative oxidohydrolase works synergistically with known saccharolytic enzyme preparations and whether the magnitude of this synergistic effect depends on the presence of reductants and divalent metal ions. Experiments such as those conducted in the examples may be used, thus the effect of reductants and metal ions on enzymatic activity may be assessed.

Preferably said oxidohydrolytic enzyme contains at least one domain that on the basis of sequence similarity as analyzed in, e.g., the current Pfam or CAZy databases is classified as a CBM33 or GH61 family protein. When the CBM33 or GH61 containing proteins have more than one domain, the additional domains are usually coupled to the C-terminus of the CBM33 or GH61 domain because the N-terminus of the CBM33 or GH61 domain is essential for oxidohydrolytic activity (see below). The CBM33 family has been classified by the CAZy (CArbohydrate-Active EnZymes) system as a carbohydrate-binding module family implying the absence of enzymatic activity. GH61 proteins have been classified as glycoside hydrolases. However, neither classification is correct in view of the results presented by the inventors and clearly the CAZy classification of these two protein families needs to be corrected. The CAZy classification is based on sequence similarity, grouping protein domains that share a certain minimal level of sequence similarity into one family. The CBM33 and GH61 domains share similar functions and they share a similar structural fold, the core of which being a twisted beta-sheet sandwich like fold, similar to that seen for fibronectin type-Ill domains (FIGS. 1D and 1E). They also share a fully conserved, diagnostic surface-located structural element (FIG. 1F) consisting of a histidine in position 1 of the mature protein (i.e., the protein after the signal peptide driving secretion has been cleaved off), another fully conserved histidine residue that is known to be crucial for catalytic activity and an N-terminal amino group that acts with these two histidines in binding a metal ion. Despite these many unifying and diagnostic characteristics, the two families share little sequence identity and will therefore most likely remain in two different families even after correction of the CAZy classification.

The oxidohydrolytic enzyme is preferably a class GH61 protein. Thus the oxidohydrolytic enzyme of the invention may contain, consist or consist essentially of a GH61 domain or GH61 protein or a biologically active fragment thereof. In this context, "consists essentially of" indicates that additional amino acids may be present in the protein, in addition to those that make up the GH61 domain or protein. Preferably there are 1-3, 1-5, 1-10, 10-20, 20-30, 30-40, 40-50, 50-60, 60-70, 70-80, 80-90 or 90-100 or more additional amino acids present. These additional amino acids are in general present C terminal to the GH61 domain.

As mentioned above, the oxidohydrolytic enzyme can comprise a GH61 domain or protein. Additional modules or domains may thus be present in the protein, which, when present are preferably at the C-terminus.

In a preferred feature a native GH61 domain or protein or a biologically active fragment thereof is used though variants of the native form may be used, some of which are described hereinafter.

Oxidohydrolytic enzymes which comprise or consist of a GH61 domain or protein or its fragments or variants are referred to herein, collectively, as GH61 proteins or GH61 family members or proteins.

Examples of suitable native proteins in this family are provided in the table below which provides relevant database accession numbers which are hereby incorporated by reference.

| Protein Name | Organism | GenBank | Uniprot |
|---|---|---|---|
| Cel1 | *Agaricus bisporus* D649 | AAA53434.1 | Q00023 |
| AfA5C5.025 | *Aspergillus fumigatus* | CAF31975.1 | Q6MYM8 |
| endo-beta-1,4-glucanase B (EglB) (Cel61A) | *Aspergillus kawachii* | BAB62318.1 | Q96WQ9 |
| AN1041.2 | *Aspergillus nidulans* FGSC A4 | EAA65609.1 | C8VTW9 |
| AN3511.2 | *Aspergillus nidulans* FGSC A4 | EAA59072.1 | |
| AN9524.2 | *Aspergillus nidulans* FGSC A4 | CBF83171.1 EAA66740.1 | C8VI93 |
| AN7891.2 | *Aspergillus nidulans* FGSC A4 | EAA59545.1 | |
| AN6428.2 | *Aspergillus nidulans* FGSC A4 | EAA58450.1 | C8V0F9 |
| AN3046.2 | *Aspergillus nidulans* FGSC A4 | EAA63617.1 | C8VIS7 |
| AN3860.2 | *Aspergillus nidulans* FGSC A4 | EAA59125.1 | C8V6H2 |
| endo-beta-1,4-glucanase (AN1602.2) | *Aspergillus nidulans* FGSC A4 | ABF50850.1 EAA64722.1 | |
| AN2388.2 | *Aspergillus nidulans* FGSC A4 | EAA64499.1 | C8VNP4 |
| An14g02670 | *Aspergillus niger* CBS 513.88 | CAK46515.1 | A2R313 |
| An15g04570 | *Aspergillus niger* CBS 513.88 | CAK97324.1 | A2R5J9 |
| An15g04900 | *Aspergillus niger* CBS 513.88 | CAK42466.1 | A2R5N0 |
| An04g08550 | *Aspergillus niger* CBS 513.88 | CAK38942.1 | A2QJX0 |
| An08g05230 | *Aspergillus niger* CBS 513.88 | CAK45495.1 | A2QR94 |
| An12g02540 | *Aspergillus niger* CBS 513.88 | CAK41095.1 | A2QYU6 |
| An12g04610 | *Aspergillus niger* CBS 513.88 | CAK97151.1 | A2QZE1 |
| AO090005000531 | *Aspergillus oryzae* RIB40 | BAE55582.1 | |
| AO090001000221 | *Aspergillus oryzae* RIB40 | BAE56764.1 | |
| AO090138000004 | *Aspergillus oryzae* RIB40 | BAE64395.1 | |
| AO090023000056 | *Aspergillus oryzae* RIB40 | BAE58643.1 | |
| AO090023000159 | *Aspergillus oryzae* RIB40 | BAE58735.1 | |
| AO090023000787 | *Aspergillus oryzae* RIB40 | BAE59290.1 | |
| AO090103000087 | *Aspergillus oryzae* RIB40 | BAE65561.1 | |
| AO090012000090 | *Aspergillus oryzae* RIB40 | BAE60320.1 | |
| GH61A | *Botryosphaeria rhodina* CBS 247.96 | CAJ81215.1 | |
| GH61B | *Botryosphaeria rhodina* CBS 247.96 | CAJ81216.1 | |

-continued

| Protein Name | Organism | GenBank | Uniprot |
| --- | --- | --- | --- |
| GH61C | *Botryosphaeria rhodina* CBS 247.96 | CAJ81217.1 | |
| GH61D | *Botryosphaeria rhodina* CBS 247.96 | CAJ81218.1 | |
| Cel6 | *Cochliobolus heterostrophus* C4 | AAM76663.1 | Q8J0H7 |
| unnamed protein product | *Coprinopsis cinerea* | CAG27578.1 | |
| Cel1 | *Cryptococcus neoformans* var. *neoformans* | AAC39449.1 | O59899 |
| CNA05840 (Cel1) | *Cryptococcus neoformans* var. *neoformans* JEC21 | AAW41121.1 | |
| xylanase II (peptide fragment) | *Fusarium oxysporum* F3 | | |
| Sequence 122805 from U.S. Pat. No. 7,214,786 | *Gibberella zeae* | ABT35335.1 | |
| FG03695.1 (Cel61E) | *Gibberella zeae* PH-1 | XP_383871.1 | |
| ORF (possible fragment) | *Glomerella graminicola* M2 | CAQ16278.1 | B5WYD8 |
| ORF | *Glomerella graminicola* M2 | CAQ16206.1 | B5WY66 |
| ORF | *Glomerella graminicola* M2 | CAQ16208.1 | B5WY68 |
| ORF | *Glomerella graminicola* M2 | CAQ16217.1 | B5WY77 |
| unnamed protein product | *Humicola insolens* | CAG27577.1 | |
| cellulase-enhancing factor (Cel61B) | *Hypocrea jecorina* QM6A | AAP57753.1 ABH82048.1 ACK19226.1 ACR92640.1 | Q7Z9M7 |
| endo-beta-1,4-glucanase IV (EGIV; Egl4) (Cel61A) | *Hypocrea jecorina* RUTC-30 | CAA71999.1 | O14405.1 |
| MG05364.4 | *Magnaporthe grisea* 70-15 | EAA54572.1 XP_359989.1 | |
| MG07686.4 | *Magnaporthe grisea* 70-15 | EAA53409.1 XP_367775.1 | |
| MG07300.4 | *Magnaporthe grisea* 70-15 | EAA56945.1 XP_367375.1 | |
| MG07575.4 | *Magnaporthe grisea* 70-15 | EAA53298.1 XP_367664.1 | |
| MG08020.4 | *Magnaporthe grisea* 70-15 | EAA57051.1 XP_362437.1 | |
| MG02502.4 | *Magnaporthe grisea* 70-15 | EAA54517.1 XP_365800.1 | |
| MG08254.4 | *Magnaporthe grisea* 70-15 | EAA57285.1 XP_362794.1 | |
| MG08066.4 | *Magnaporthe grisea* 70-15 | EAA57097.1 XP_362483.1 | |
| MG04547.4 | *Magnaporthe grisea* 70-15 | EAA50788.1 XP_362102.1 | |
| MG08409.4 | *Magnaporthe grisea* 70-15 | EAA57439.1 XP_362640.1 | |
| MG09709.4 | *Magnaporthe grisea* 70-15 | EAA49718.1 XP_364864.1 | |
| MG04057.4 | *Magnaporthe grisea* 70-15 | EAA50298.1 XP_361583.1 | |
| MG06069.4 | *Magnaporthe grisea* 70-15 | EAA52941.1 XP_369395.1 | |
| MG09439.4 | *Magnaporthe grisea* 70-15 | EAA51422.1 XP_364487.1 | |
| MG06229.4 | *Magnaporthe grisea* 70-15 | EAA56258.1 XP_369714.1 | |
| MG07631.4 | *Magnaporthe grisea* 70-15 | EAA53354.1 XP_367720.1 | |
| MG06621.4 (fragment) | *Magnaporthe grisea* 70-15 | XP_370106.1 | |
| NCU07898.1 | *Neurospora crassa* OR74A | EAA33178.1 XP_328604.1 | |
| NCU05969.1 | *Neurospora crassa* OR74A | EAA29347.1 XP_325824.1 | |
| NCU02916.1 | *Neurospora crassa* OR74A | EAA36362.1 XP_330104.1 | |

-continued

| Protein Name | Organism | GenBank | Uniprot |
| --- | --- | --- | --- |
| NCU03000.1 (B24P7.180) | *Neurospora crassa* OR74A | CAB97283.2 EAA36150.1 XP_330187.1 | Q9P3R7 |
| NCU07760.1 | *Neurospora crassa* OR74A | EAA29018.1 XP_328466.1 | |
| NCU07520.1 | *Neurospora crassa* OR74A | EAA29132.1 XP_327806.1 | |
| NCU01050.1 (G15G9.090) | *Neurospora crassa* OR74A | CAD21296.1 EAA32426.1 XP_326543.1 | Q8WZQ2 |
| NCU02240.1 | *Neurospora crassa* OR74A | EAA30263.1 XP_331016.1 | |
| NCU02344.1 (B23N11.050) | *Neurospora crassa* OR74A | CAF05857.1 EAA30230.1 XP_331120.1 | |
| NCU00836.1 | *Neurospora crassa* OR74A | EAA34466.1 XP_325016.1 | |
| NCU08760.1 | *Neurospora crassa* OR74A | EAA26873.1 XP_330877.1 | |
| NCU07974.1 | *Neurospora crassa* OR74A | EAA33408.1 XP_328680.1 | |
| NCU03328.1 (B10C3.010) | *Neurospora crassa* OR74A | CAD70347.1 EAA26656.1 XP_322586.1 | Q873G1 |
| NCU01867.1 (B13N4.070) | *Neurospora crassa* OR74A | CAE81966.1 EAA36262.1 XP_329057.1 | Q7SHD9 |
| beta-1,3-1,4-glucanase (peptide fragment) | *Paecilomyces thermophila* J18 | | |
| Pc20g11100 | *Penicillium chrysogenum* Wisconsin 54-1255 | CAP86439.1 | B6HG02 |
| Pc12g13610 | *Penicillium chrysogenum* Wisconsin 54-1255 | CAP80988.1 | B6H016 |
| Pc13g07400 | *Penicillium chrysogenum* Wisconsin 54-1255 | CAP91809.1 | B6H3U0 |
| Pc13g13110 | *Penicillium chrysogenum* Wisconsin 54-1255 | CAP92380.1 | B6H3A3 |
| Cel61 (Cel61A) | *Phanerochaete chrysosporium* BKM-F-1767 | AAM22493.1 | Q8NJI9 |
| Pa_4_1020 | *Podospora anserina* S mat+ | CAP61476.1 | B2ADG1 |
| unnamed protein product | *Podospora anserina* S mat+ | CAP68173.1 | B2AUV0 |
| unnamed protein product | *Podospora anserina* S mat+ | CAP68309.1 | B2AV86 |
| unnamed protein product | *Podospora anserina* S mat+ | CAP61650.1 | B2ADY5 |
| unnamed protein product | *Podospora anserina* S mat+ | CAP68352.1 | B2AVC8 |
| Pa_7_3160 | *Podospora anserina* S mat+ | CAP68375.1 | B2AVF1 |
| unnamed protein product (fragment) | *Podospora anserina* S mat+ | CAP71532.1 | B2B346 |
| unnamed protein product | *Podospora anserina* S mat+ | CAP71839.1 | B2B403 |
| unnamed protein product | *Podospora anserina* S mat+ | CAP72740.1 | B2B4L5 |
| Pa_5_8940 | *Podospora anserina* S mat+ | CAP64619.1 | B2AKU6 |
| unnamed protein product | *Podospora anserina* S mat+ | CAP73072.1 | B2B5J7 |
| unnamed protein product | *Podospora anserina* S mat+ | CAP64732.1 | B2AL94 |
| Pa_2_6530 | *Podospora anserina* S mat+ | CAP73254.1 | B2B629 |
| unnamed protein product | *Podospora anserina* S mat+ | CAP73311.1 | B2B686 |
| unnamed protein product | *Podospora anserina* S mat+ | CAP73320.1 | B2B695 |
| unnamed protein product | *Podospora anserina* S mat+ | CAP64865.1 | B2ALM7 |

| Protein Name | Organism | GenBank | Uniprot |
|---|---|---|---|
| unnamed protein product | Podospora anserina S mat+ | CAP65111.1 | B2AMI8 |
| unnamed protein product | Podospora anserina S mat+ | CAP65855.1 | B2APD8 |
| unnamed protein product | Podospora anserina S mat+ | CAP65866.1 | B2APE9 |
| unnamed protein product | Podospora anserina S mat+ | CAP65971.1 | B2API9 |
| unnamed protein product | Podospora anserina S mat+ | CAP66744.1 | B2ARG6 |
| Pa_1_500 | Podospora anserina S mat+ | CAP59702.1 | B2A9F5 |
| unnamed protein product | Podospora anserina S mat+ | CAP61048.1 | B2AC83 |
| unnamed protein product | Podospora anserina S mat+ | CAP67176.1 | B2AS05 |
| Pa_1_22040 | Podospora anserina S mat+ | CAP67190.1 | B2AS19 |
| unnamed protein product | Podospora anserina S mat+ | CAP67201.1 | B2AS30 |
| unnamed protein product | Podospora anserina S mat+ | CAP67466.1 | B2ASU3 |
| unnamed protein product | Podospora anserina S mat+ | CAP67481.1 | B2ASV8 |
| unnamed protein product | Podospora anserina S mat+ | CAP67493.1 | B2ASX0 |
| unnamed protein product | Podospora anserina S mat+ | CAP70156.1 | B2AZV6 |
| Pa_4_350 | Podospora anserina S mat+ | CAP61395.1 | B2AD80 |
| Pa_1_16300 | Podospora anserina S mat+ | CAP67740.1 | B2ATL7 |
| unnamed protein product | Podospora anserina S mat+ | CAP70248.1 | B2AZD4 |
| SMU2916 (fragment) | Sordaria macrospora k-hell | CAQ58424.1 | |
| cellulase-enhancing factor (GH61A) | Thermoascus aurantiacus | ABW56451.1 ACS05720.1 | |
| unnamed protein product | Thielavia terrestris | CAG27576.1 | |
| cellulase-enhancing factor (GH61B) | Thielavia terrestris NRRL 8126 | ACE10231.1 | |
| Sequence 4 from U.S. Pat. No. 7,361,495 (GH61C) | Thielavia terrestris NRRL 8126 | ACE10232.1 | |
| Sequence 4 from U.S. Pat. No. 7,361,495 (GH61C) | Thielavia terrestris NRRL 8126 | ACE10232.1 | |
| Sequence 6 from U.S. Pat. No. 7,361,495 (GH61D) | Thielavia terrestris NRRL 8126 | ACE10233.1 | |
| Sequence 6 from U.S. Pat. No. 7,361,495 (GH61D) | Thielavia terrestris NRRL 8126 | ACE10233.1 | |
| cellulase-enhancing factor (131562) (GH61E) | Thielavia terrestris NRRL 8126 | ACE10234.1 | |
| Sequence 10 from U.S. Pat. No. 7,361,495 (GH61G) | Thielavia terrestris NRRL 8126 | ACE10235.1 | |
| Sequence 10 from U.S. Pat. No. 7,361,495 (GH61G) | Thielavia terrestris NRRL 8126 | ACE10235.1 | |
| endoglucanase (EnGluIV; EndoGluIV) | Trichoderma saturnisporum | ADB89217.1 | |
| Endoglucanase IV | Trichoderma sp. SSL | ACH92573.1 | B5TYI4 |
| endoglucanase IV (EgiV) | Trichoderma viride AS 3.3711 | ACD36973.1 | B4YEW3 |
| endoglucanase VII (EgvII) | Trichoderma viride AS 3.3711 | ACD36971.1 | B4YEW1 |
| Endoglucanase II (EgII) | Volvariella volvacea | AAT64005.1 | Q6E5B4 |
| unknown (ZM_BFc0036G02) | Zea mays B73 | ACF78974.1 ACR36748.1 | B4FA31 |

GH61 proteins from *Phanerochaete chrysosporium* are also preferred (see Vanden Wymelenberg et al., 2009, *Appl Environ Microbiol.* 75(12): 4058-68; Hori et al., 2011, *FEMS Microbiol Lett.* 321(1): 14-23).

Preferred GH61 proteins are from fungi, in particular from *Thielavia*, especially preferably from *Thielavia terrestris* or *Thielavia aurantiacus*. Especially preferably said GH61 protein is GH61A from *Thielavia aurantiacus* or GH61B, GH61C, GH61D, GH61E or GH61G from *Thielavia terrestris* as described above. Other preferred GH61 proteins include GH61A and B from *Hypocrea jecorina* (SEQ ID NOs: 15 and 16).

The GH61 protein can thus be or correspond to or comprise a naturally occurring GH61 protein that is found in nature or a biologically active fragment thereof. In the alternative the GH61 protein may be a non-native variant as disclosed hereinafter.

In an alternative preferred feature the oxidohydrolytic enzyme is a class CBM33 family protein. The CBM33 family comprises a carbohydrate-binding module (CBM) which is defined as a contiguous amino acid sequence within a carbohydrate binding protein with a discreet fold having carbohydrate-binding activity. For example, chitinases are known which contain one or more chitin binding modules in addition to catalytic regions. ChiA of *Serratia marcescens* contains a fibronectin type III—type CBM, ChiB of *Serratia marcescens* contains a family 5 CBM and ChiC of *Serratia marcescens* contains a family 12 and a fibronectin type III—like CBM. See Bourne & Henrissat, 2001, *Curr. Opin. Struct. Biol.* 11: 593 for domain nomenclature. Likewise, many cellulases contain CBMs that bind to cellulose. Proteins binding to chitin and containing CBMs that stimulate such binding may for example be structural or signalling molecules or they can be enzymes and the overall function of the protein may be determined by domains that are present in addition to the carbohydrate binding module. The CBMs for use in methods of the invention must, however, have oxidohydrolytic activity as defined above. So far such oxidohydrolytic activity has been detected in only one CBM family, namely CBM family 33. This is exemplified by the function of the chitin-binding protein (CBP) CBP21.

Members of family 33 of Carbohydrate Binding Modules (CBM33) may be identified according to the CAZY classification system (cazy.org/CAZY/fam/acc_CBM.html), which is based on sequence similarities (Davies & Henrissat, 2002, *Biochem Soc T* 30: 291-297 and Bourne & Henrissat, 2001, supra). Proteins in this family are known to bind to chitin, but binding to other polysaccharides, including cellulose, has also been observed (Moser et al., 2008, *Biotechnol. Bioeng.* 100(6):1066-77). For some of these proteins it has been shown that they act synergistically with chitinases and cellulases in the degradation of chitin and cellulose, respectively (Vaaje-Kolstad et al., 2005, *J. Biol. Chem.* 280(31): 28492-7; Vaaje-Kolstad et al., 2009, *FEBS J.* 276(8):2402-15; Moser et al., 2008, supra), as described in the Examples.

Studies of the action of the chitin-binding protein CBP21 (and other CBM33 proteins) have now led to the identification of CBM33 proteins as oxidohydrolases.

As described herein, all members of CBM family 33 contain a family 33 carbohydrate binding module. In several cases, the CBM33 module makes up the whole protein, i.e., the protein consists of or consists essentially of a single family 33 CBM, which is in nature synthesized and secreted as such. However some family 33 CBMs may be fused to one or more additional non-catalytic carbohydrate binding modules (e.g., CBM family 2, CBM family 3 and CBM family 5 modules). These proteins are bi- or multi-domain proteins. There is also one known example of a family 33 carbohydrate binding module that is present as an individual module within a much larger catalytic protein. This is the beta-1,4-mannanase protein of *Caldibacillus cellulovorans* (Sunna et al., 2000, *Appl. Environ. Micro.* 66(2): 664-670).

The family 33 CBMs are usually approximately 150-250 amino acids, e.g., 160-240, 170-230, 180-220, 190-210 amino acids in size and have a molecular weight of approximately 20 kDa, preferably 19-21 kDa, 18-21 kDa, 19-22 kDa or 18-20 kDa in size, though CBM33 domains as large as 300-400 amino acids with a molecular weight of approximately 30-40 kDa may also be used. The size of a protein can readily be determined by standard methods that are known in the art.

Preferably, the oxidohydrolytic enzyme consists of a single family 33 CBM, or consists essentially of a family 33 CBM.

If said oxidohydrolytic enzyme "consists essentially of" a family 33 CBM, it is meant that additional amino acids may be present in the protein, in addition to those that make up the family 33 CBM. Preferably there are 1-3, 1-5, 1-10, 10-20, 20-30, 30-40, 40-50, 50-60, 60-70, 70-80, 80-90 or 90-100 or more additional amino acids present. These additional amino acids are in general present C terminal to the family 33 CBM.

Alternatively, the oxidohydrolytic enzyme can comprise a family 33 CBM. Additional modules or domains may thus be present in the protein. Examples of such modules are CBM family 2, CBM family 3 and CBM family 5 modules. If additional domains or modules are present, they are in general found C-terminal to the family 33 CBM.

Thus in a preferred aspect, the oxidohydrolytic enzyme can contain, consist or consist essentially of a naturally occurring family 33 CBM (or CBM33 family protein) such as CBP21 (or to a homologue thereof from another species) or a biologically active fragment thereof. It can alternatively contain, consist or consist essentially of a variant of a naturally occurring family 33 CBM (or CBM33 family protein) or a biologically active fragment thereof.

Oxidohydrolytic enzymes which comprise or consist of a family 33 CBM module or the full family 33 CBM protein (which comprises the family 33 CBM module) or its fragments or variants are referred to herein, collectively, as CBM33 proteins or CBM33 family members or proteins.

Naturally occurring CBM33 proteins that can be used in the invention include microbial (e.g., bacterial), eukaryotic (e.g., *Dictyostelium*) or viral CBM33 proteins. Bacterial CBM33 proteins are, however, preferred.

Examples of known CBM33 proteins which may be used in methods of the invention and relevant database accession numbers (which are hereby incorporated by reference) are set out in Table 1:

| PROTEIN | ORGANISM | GENBANK/GENPEPT | |
| --- | --- | --- | --- |
| BACTERIA | | | |
| Cbp1 | *Alteromonas* sp. O-7 | AB063629 | BAB79619.1 |
| chitin binding protein ChbA | *Bacillus amyloliquefaciens* ALKO 2718 | AF181997 | AAG09957.1 |
| BA_3348 | *Bacillus anthracis* str. A2012 | NC_003995 | NP_656708.1 |
| BA2827 | *Bacillus anthracis* str. Ames | AE017033 | AAP26659.1 |
| | | NC_003997 | NP_845173.1 |
| BA2793 | *Bacillus anthracis* str. Ames | AE017032 | AAP26628.1 |
| | | NC_003997 | NP_845142.1 |
| GBAA2827 | *Bacillus anthracis* str. Ames 0581 | AE017334 | AAT31944.1 |
| GBAA2793 | *Bacillus anthracis* str. Ames 0581 | AE017334 | AAT31910.1 |

-continued

| PROTEIN | ORGANISM | GENBANK/GENPEPT | |
|---|---|---|---|
| BAS2636 | *Bacillus anthracis* str. Sterne | AE017225 | AAT54946.1 |
| BAS2604 | *Bacillus anthracis* str. Sterne | AE017225 | AAT54914.1 |
| BCE2855 | *Bacillus cereus* ATCC 10987 | AE017273 | AAS41767.1 |
| | | NC_003909 | NP_979159.1 |
| BCE2824 | *Bacillus cereus* ATCC 10987 | AE017273 | AAS41736.1 |
| | | NC_003909 | NP_979128.1 |
| BC2827 | *Bacillus cereus* ATCC 14579 | AE017007 | AAP09778.1 |
| | | NC_004722 | NP_832577.1 |
| BC2798 | *Bacillus cereus* ATCC 14579 | AE017007 | AAP09751.1 |
| | | NC_004722 | NP_832550.1 |
| pE33L466_0276 (ChbA) | *Bacillus cereus* E33L | CP000040 | AAY60428.1 |
| BTZK2523 (ChB) | *Bacillus cereus* ZK | CP000001 | AAU17736.1 |
| BTZK2552 (ChB) | *Bacillus cereus* ZK | CP000001 | AAU17707.1 |
| ABC1161 | *Bacillus clausii* KSM-K16 | AP006627 | BAD63699.1 |
| BH1303 | *Bacillus halodurans* C-125 | AP001511 | BAB05022.1 |
| | | NC_002570 | NP_242169.1 |
| BLi00521 or BL00145 | *Bacillus licheniformis* DSM 13 ATCC 14580 | CP000002 | AAU22121.1 |
| | | AE017333 | AAU39477.1 |
| BT9727_2586 (ChB) | *Bacillus thuringiensis* serovar konkukian str. 97-27 | AE017355 | AAT61310.1 |
| BT9727_2556 (ChB) | *Bacillus thuringiensis* serovar konkukian str. 97-27 | AE017355 | AAT61323.1 |
| BMAA1785 | *Burkholderia mallei* ATCC 23344 | CP000011 | AAU45854.1 |
| BMA2896 | *Burkholderia mallei* ATCC 23344 | CP000010 | AAU48386.1 |
| BURPS1710b_0114 | *Burkholderia pseudomallei* 1710b | CP000124 | ABA49030.1 |
| BURPS1710b_A2047 | *Burkholderia pseudomallei* 1710b | CP000125 | ABA53645.1 |
| BPSL3340 | *Burkholderia pseudomallei* K96243 | BX571965 | CAH37353.1 |
| BPSS0493 | *Burkholderia pseudomallei* K96243 | BX571966 | CAH37950.1 |
| Bcep18194_C6726 | *Burkholderia* sp. 383 | CP000150 | ABB05775.1 |
| BTH_II1925 | *Burkholderia thailandensis* E264; ATCC 700388 | CP000085 | ABC34637.1 |
| BTH_I3219 | *Burkholderia thailandensis* E264; ATCC 700388 | CP000086 | ABC38514.1 |
| Beta-1,4-mannanase (ManA) | *Caldibacillus cellulovorans* | AF163837 | AAF22274.1 |
| CV0554 | *Chromobacterium violaceum* ATCC 12472 | AE016911 | AAQ58230.1 |
| | | NC_005085 | NP_900224.1 |
| CV0553 | *Chromobacterium violaceum* ATCC 12472 | AE016911 | AAQ58229.1 |
| | | NC_005085 | NP_900223.1 |
| CV2592 (CpbD) | *Chromobacterium violaceum* ATCC 12472 | AE016919 | AAQ60262.1 |
| | | NC_005085 | NP_902262.1 |
| CV3489 | *Chromobacterium violaceum* ATCC 12472 | AE016922 | AAQ61150.1 |
| | | NC_005085 | NP_903159.1 |
| CV3323 (CbpD1) | *Chromobacterium violaceum* ATCC 12472 | AE016921 | AAQ60987.1 |
| | | NC_005085 | NP_902993.1 |
| EF0362 | *Enterococcus faecalis* V583 | AE016948 | AAO80225.1 |
| | | NC_004668 | NP_814154.1 |
| Sequence 4287 from U.S. Pat. No. 6,583,275 | *Enterococcus faecium* | — | AAQ43729.1 |
| FTL_1408 | *Francisella tularensis* subsp. *holarctica* LVS | AM233362 | CAJ79847.1 |
| FTT0816c | *Francisella tularensis* subsp. *tularensis* Schu 4 | AJ749949 | CAG45449.1 |
| HCH_00807 | *Hahella chejuensis* KCTC 2396 | CP000155 | ABC27701.1 |
| HCH_03973 | *Hahella chejuensis* KCTC 2396 | CP000155 | ABC30692.1 |
| lp_1697 | *Lactobacillus plantarum* WCFS1 | AL935256 | CAD64126.1 |
| | | NC_004567 | NP_785278.1 |
| LSA1008 | *Lactobacillus sakei* subsp. *sakei* 23K | CR936503 | CAI55310.1 |
| YucG | *Lactococcus lactis* subsp. *lactis* IL1403 | AE006425 | AAK06049.1 |
| | | NC_002662 | NP_268108.1 |
| lpp0257 | *Legionella pneumophila* Paris | CR628336 | CAH11404.1 |
| Lin2611 | *Listeria innocua* | AL596173 | CAC97838.1 |
| | | NC_003212 | NP_471941.1 |
| Lmo2467 | *Listeria monocytogenes* EGD-e | AL591983 | CAD00545.1 |
| | | NC_003210 | NP_465990.1 |
| LMOf2365_2440 | *Listeria monocytogenes* str. 4b F2365 | AE017330 | AAT05205.1 |
| OB0810 | *Oceanobacillus iheyensis* HTE831 | AP004595 | BAC12766.1 |
| | | NC_004193 | NP_691731.1 |

-continued

| PROTEIN | ORGANISM | GENBANK/GENPEPT | |
|---|---|---|---|
| PBPRB0312 | *Photobacterium profundum* SS9 | CR378676 | CAG22185.1 |
| plu2352 | *Photorhabdus luminescens* subsp. *laumondii* TTO1 | BX571866 | CAE14645.1 |
| | | NC_005126 | NP_929598.1 |
| Sequence 6555 from U.S. Pat. No. 6,605,709 | *Proteus mirabilis* | — | AAR43285.1 |
| chitin-binding protein ChiB | *Pseudoalteromonas* sp. S9 | AF007895 | AAC79666.1 |
| chitin-binding protein (CbpD; PA0852) | *Pseudomonas aeruginosa* PAO1 | AE004520 | AAG04241.1 |
| | | NC_002516 | NP_249543.1 |
| chitin-binding protein (CbpD) | *Pseudomonas aeruginosa* PAO25 | AF196565 | AAF12807.1 |
| PFL_2090 | *Pseudomonas fluorescens* Pf-5 | CP000076 | AAY91365.1 |
| Pfl_3569 | *Pseudomonas fluorescens* PfO-1 | CP000094 | ABA75307.1 |
| Psyr_2856 | *Pseudomonas syringae* pv. *syringae* B728a | CP000075 | AAY37892.1 |
| PSPTO2978 | *Pseudomonas syringae* pv. *tomato* str. DC3000 | AE016866 | AAO56470.1 |
| | | NC_004578 | NP_792775.1 |
| RF_0708 | *Rickettsia felis* URRWXCal2 | CP000053 | AAY61559.1 |
| chitin-binding protein (CbpA) | *Saccharophagus degradans* 2-40 | BK001045 | DAA01337.1 |
| ORF | *Salinivibrio costicola* 5SM-1 | AY207003 | AAP42509.1 |
| chitin-binding protein (Cbp21) | *Serratia marcescens* 2170 | AB015998 | BAA31569.1 |
| chitin-binding protein (Cbp21) | *Serratia marcescens* BJL200 | AY665558 | AAU88202.1 |
| ORF2 | *Serratia marcescens* KCTC2172 | L38484 | AAC37123.1 |
| SO1072 | *Shewanella oneidensis* MR-1 | AE015551 | AAN54144.1 |
| | | NC_004347 | NP_716699.1 |
| SG1515 (possible fragment) | *Sodalis glossinidius* str. 'morsitans' | AP008232 | BAE74790.1 |
| SAV6560 | *Streptomyces avermitilis* MA-4680 | AP005047 | BAC74271.1 |
| | | NC_003155 | NP_827736.1 |
| SAV2168 | *Streptomyces avermitilis* MA-4680 | AP005029 | BAC69879.1 |
| | | NC_003155 | NP_823344.1 |
| SAV5223 (Chb) | *Streptomyces avermitilis* MA-4680 | AP005042 | BAC72935.1 |
| | | NC_003155 | NP_826400.1 |
| SAV2254 (CelS2) | *Streptomyces avermitilis* MA-4680 | AP005030 | BAC69965.1 |
| | | NC_003155 | NP_823430.1 |
| SCO7225 or SC2H12.24 | *Streptomyces coelicolor* A3(2) | AL359215 | CAB94648.1 |
| | | NC_003888 | NP_631281.1 |
| SCO6345 or SC3A7.13 | *Streptomyces coelicolor* A3(2) | AL031155 | CAA20076.1 |
| | | NC_003888 | NP_630437.1 |
| SCO2833 (Chb) | *Streptomyces coelicolor* A3(2) | AL136058 | CAB65563.1 |
| | | NC_003888 | NP_627062.1 |
| SCO0643 or SCF91.03c | *Streptomyces coelicolor* A3(2) | AL132973 | CAB61160.1 |
| | | NC_003888 | NP_624952.1 |
| SCO0481 or SCF80.02 | *Streptomyces coelicolor* A3(2) | AB017013 | BAA75647.1 |
| | | AL121719 | CAB57190.1 |
| | | NC_003888 | NP_624799.1 |
| SCO1734 or SCI11.23 | *Streptomyces coelicolor* A3(2) | AL096849 | CAB50949.1 |
| | | NC_003888 | NP_626007.1 |
| CelS2 (SCO1188 or SCG11A.19) | *Streptomyces coelicolor* A3(2) | AL133210 | CAB61600.1 |
| | | NC_003888 | NP_625478.1 |
| chitin binding protein | *Streptomyces griseus* | AB023785 | BAA86267.1 |
| cellulose binding protein (ORF2) | *Streptomyces halstedii* | U51222 | AAC45430.1 |
| chitin-binding protein | *Streptomyces olivaceoviridis* ATCC 11238 | X78535 | CAA55284.1 |
| chitin binding protein (Chb2) | *Streptomyces reticuli* | Y14315 | CAA74695.1 |
| chitin-binding protein (Cbp1) | *Streptomyces thermoviolaceus* OPC-520 | AB110078 | BAD01591.1 |
| chitin-binding protein celS2 | *Streptomyces viridosporus* | AF126376 | AAD27623.1 |
| Tfu_1665 (E8) | *Thermobifida fusca* YX | CP000088 | AAZ55700.1 |
| Tfu_1268 (E7) | *Thermobifida fusca* YX | CP000088 | AAZ55306.1 |
| VCA0140 | *Vibrio cholerae* N16961 | AE004355 | AAF96053.1 |
| | | NC_002506 | NP_232540.1 |
| VCA0811 | *Vibrio cholerae* N16961 | AE004409 | AAF96709.1 |
| | | NC_002506 | NP_233197.1 |

| PROTEIN | ORGANISM | GENBANK/GENPEPT | |
|---|---|---|---|
| VFA0143 | *Vibrio fischeri* ES114 | CP000021 | AAW87213.1 |
| VFA0013 | *Vibrio fischeri* ES114 | CP000021 | AAW87083.1 |
| VPA0092 | *Vibrio parahaemolyticus* RIMD 2210633 | AP005084 | BAC61435.1 |
| | | NC_004605 | NP_799602.1 |
| VPA1598 | *Vibrio parahaemolyticus* RIMD 2210633 | AP005089 | BAC62941.1 |
| | | NC_004605 | NP_801108.1 |
| VV21258 | *Vibrio vulnificus* CMCP6 | AE016812 | AAO08152.1 |
| | | NC_004460 | NP_763162.1 |
| VV20044 | *Vibrio vulnificus* CMCP6 | AE016808 | AAO07021.1 |
| | | NC_004460 | NP_762031.1 |
| VVA0086 | *Vibrio vulnificus* YJ016 | AP005344 | BAC96112.1 |
| | | NC_005140 | NP_936142.1 |
| VVA0551 | *Vibrio vulnificus* YJ016 | AP005346 | BAC96577.1 |
| | | NC_005140 | NP_936607.1 |
| ChiY | *Yersinia enterocolitica* (type 0:8) WA-314 | AJ344214 | CAC83040.2 |
| YP0706 | *Yersinia pestis* biovar Medievalis str. 91001 | AE017129 | AAS60972.1 |
| | | NC_005810 | NP_992095.1 |
| YPO3227 | *Yersinia pestis* CO92 | AJ414156 | CAC92462.1 |
| | | NC_003143 | NP_406699.1 |
| Y0962 | *Yersinia pestis* KIM | AE013699 | AAM84543.1 |
| | | NC_004088 | NP_668292.1 |
| YPTB3366 | *Yersinia pseudotuberculosis* 32953 | IPBX936398 | CAH22604.1 |
| YPTB0899 | *Yersinia pseudotuberculosis* 32953 | IPBX936398 | CAH20139.1 |
| EUKARYOTA | | | |
| ORF-26 | *Agrotis segetum* nucleopolyhedrovirus | DQ123841 | AAZ38192.1 |
| spheroidin-like protein (Gp 37) | *Autographa californica* nucleopolyhedrovirus | L22858 | AAA66694.1 |
| | | D00583 | BAA00461.1 |
| | | NC_001623 | NP_054094.1 |
| Fusolin | *Bombyx mori* nuclear polyhedrosis virus | U55071 | AAB47606.1 |
| | | L33180 | AAC63737.1 |
| | | NC_001962 | NP_047468.1 |
| Spheroidin | *Choristoneura biennis* entomopoxvirus | M34140 | AAA42887.1 |

| VIRUSES | | | |
|---|---|---|---|
| PROTEIN | ORGANISM | GENBANK/GENPEPT | |
| ORF-26 | *Agrotis segetum* nucleopolyhedrovirus | DQ123841 | AAZ38192.1 |
| Spheroidin-like protein (Gp 37) | *Autographa californica* nucleopolyhedrovirus | D00583 | BAA00461.1 |
| | | L22858 | AAA66694.1 |
| | | NC_001623 | NP 054094.1 |
| Fusolin | *Bombyx mori* nuclear polyhedrosis virus | U55071 | AAB47606.1 |
| | | NC_001962 | NP_047468.1 |
| | | L33180 | AAC63737.1 |
| Spheroidin | *Choristoneur biennis* entomopoxvirus | M341140 | AAA42887.1 |
| ORF60 | *Choristoneura fumiferana* defective nucleopolyhedrovirus | AY327402 | AAQ91667.1 |
| | | NC_005137 | NP_932669.1 |
| spindle-like protein | *Choristoneura fumiferana* nuclear polyhedrosis virus | U26734 | AAC55636.1 |
| | | NC_004778 | NP_848371.1 |
| GP37 (ORF-67 GP37) | *Chrysodeixis chalcites* nucleopolyhedrovirus | AY864330 | AAY83998.1 |
| ORF57 | *Epiphyas postvittana* nucleopolyhedrovirus | AY043265 | AAK85621.1 |
| | | NC_003083 | NP_203226.1 |
| GP37 | *Helicoverpa armigera* single nucleocapsid polyhedrovirus | AF266696 | AAK57880.1 |
| | | AF303045 | AAK96305.1 |
| | | NC_003094 | NP_203613.1 |

VIRUSES

| PROTEIN | ORGANISM | GENBANK/GENPEPT | |
|---|---|---|---|
| ORF59 | *Helicoverpa zea* nucleopolyhedrovirus | AF334030 | AAL56204.1 |
| | | NC_003349 | NP_542682.1 |
| gp37 | *Heliocoverpa armigera* nucleopolyhedrovirus G4 | AF271059 | AAG53801.1 |
| | | NC_002654 | NP_075127.1 |
| Fusolin | *Heliothis armigera* entomopoxvirus | L08077 | AAA92858.1 |
| HynVgp086 (slp) | *Hyphantria cunea* nucleopolyhedrovirus | AP009046 | BAE72375.1 |
| Gp37 protein | *Leucania separata* nuclear polyhedrosis virus | AB009614 | BAA24259.1 |
| fusolin-like protein | *Lymantria dispar* nucleopolyhedrovirus | U38895 | AAB07702.1 |
| | | AF081810 | AAC70254.1 |
| | | NC_001973 | NP_047705.1 |
| gp37 protein | *Mamestra brassicae* nucleopolyhedrovirus | AF108960 | AAD45231.1 |
| ORF 37 (Gp37) | *Mamestra configurata* nucleopolyhedrovirus A | U59461 | AAM09145.1 |
| | | AF539999 | AAQ11056.1 |
| Gp37 | *Mamestra configurata* nucleopolyhedrovirus B | AY126275 | AAM95019.1 |
| | | NC_004117 | NP_689207.1 |
| spheroidin-like protein (Gp 37) | *Orgyia pseudotsugata* nuclear polyhedrosis virus | U75930 | AAC59068.1 |
| | | D13306 | BAA02566.1 |
| | | NC_001875 | NP_046225.1 |
| enhancing factor | *Pseudaletia separata* entomopoxvirus | D50590 | BAA09138.1 |
| ORF25 | *Spodoptera exigua* nucleopolyhedrovirus | AF 169823 | AAF33555.1 |
| | | NC_002169 | NP_037785.1 |
| gp37 (fragment) | *Spodoptera frugiperda* MNPV | AY250076 | AAP79107.1 |
| ubiquitin GP37 fusion protein | *Spodoptera litura* nucleopolyhedrovirus G2 | AF325155 | AAL01718.1 |
| | | NC_003102 | NP_258300.1 |
| gp37 | *Trichoplusia ni* single nucleopolyhedrovirus | DQ017380 | AAZ67435.1 |
| Fusolin | unidentified entomopoxvirus | X77616 | CAA54706.1 |
| ORF107 | *Xestia c-nigrum* granulovirus | AF162221 | AAF05221.1 |
| | | NC_002331 | NP_059255.1 |

Other preferred bacterial CBM33 proteins include:

| PROTEIN | ORGANISM | GENBANK/GENPEPT | |
|---|---|---|---|
| Cfla_0175 | *Cellulomonas flavigena* DSM 20109 | ADG73094.1 | D5UGB1 |
| Cfla_0172 | *Cellulomonas flavigena* DSM 20109 | ADG73091.1 | D5UGA8 |
| Cfla_0316 | *Cellulomonas flavigena* DSM 20109 | ADG73234.1 | D5UH31 |
| Cfla_0490 | *Cellulomonas flavigena* DSM 20109 | ADG73405.1 | D5UHY1 |
| CJA_2191 (Cbp33A) | *Cellvibrio japonicus* Ueda107 | ACE83992.1 | B3PJ79 |
| CJA_3139 (cbp33/10B) | *Cellvibrio japonicus* Ueda107 | ACE84760.1 | B3PDT6 |

Bacterial CBM33 proteins can be from any appropriate source but are preferably from a genus selected from the group consisting of *Bacillus, Chromobacterium, Enterococcus, Francisella, Hahella, Lactobacillus, Lactococcus, Legionella, Listeria, Oceanobacillus, Photobacterium, Photothabdus, Proteus, Pseudoalteromonas, Pseudomonas, Rickettsia, Saccharophagus, Salinvibrio, Serratia, Shewanella, Sodalis, Streptomyces, Thermobifida, Vibrio* and *Yersini* and optionally *Cellulomonas* and *Cellvibrio*.

Preferably said CBM33 protein is a CBP21 as described in U.S. Patent Application No. 2007/0218046 which is incorporated herein by reference. For example the CBP21 of *Serratia marescens* (SEQ ID NO: 4) is preferred. Alternatively, the EfCBM33 of *Enterococcus faecalis* (SEQ ID NO: 5), E7 of *Thermobifida fusca* (SEQ ID NO: 6), CelS2 of *Streptomyces coelicolor* A3(2) (SEQ ID NO: 7), Cfla_0175 of *Cellulomonas flavigena* DSM 20109) (SEQ ID NO: 8), Cfla_0172 of *Cellulomonas flavigena* DSM 20109) (SEQ ID NO: 9), Cfla_0316 of *Cellulomonas flavigena* DSM 20109) (SEQ ID NO: 10), Cfla_0490 of *Cellulomonas flavigena* DSM 20109) (SEQ ID NO: 11), CJA_2191 (Cbp33A) of *Cellvibrio japonicus* Ueda107 (SEQ ID NO: 12), CJA_3139 (Cbp33/10B) of *Cellvibrio japonicus* Ueda107 (SEQ ID NO: 13) and SCO1734 of *Streptomyces coelicolar* A3(2)) (SEQ ID NO: 14), may be used. ChbA of *B. amyloliquefaciens* (Chu et al., 2001, *Microbiology* 147 (Pt 7):1793-803) CHB1, 2 & 3 of *Streptomyces* (Svergun et al., 2000, *Biochemistry* 39(35):10677-83, Zeltins et al., 1997, *Eur. J. Biochem.* 246(2):557-64, Zeltins et al., 1995, *Anal. Biochem.* 231(2):287-94, Schnellmann et al., 1994, *Mol. Microbiol.* 13(5):807-19; Kolbe et al., 1998, *Microbiology* 144 (Pt 5):1291-7; Saito et al., 2001, *Appl. Environ. Microbiol.* 67(3):1268-73) and CBP1 of *Alteramonas* (Tsujibo et al., 2002, *Appl. Environ. Microbiol.* 68:263-270) are also preferred CBM33 proteins for use in the invention. All of these references are incorporated herein by reference.

The oxidohydrolytic enzyme can thus be or correspond to or comprise a naturally occurring CBM33 family protein (such as CBP21, EfCBM33, ChbA, CHB1, 2 & 3 and CBP1 or E7, CelS2, Cfla_0175, Cfla_0172, Cfla_0316, Cfla_0490, CJA_2191 (Cbp33A), CJA_3139 (Cbp33/10B) and SCO1734) or GH61 family protein in that it is found in nature or a biologically active fragment thereof. In the alternative the oxidohydrolytic enzyme may be a non-native variant as disclosed hereinafter.

As mentioned above, the oxidohydrolytic enzymes may be native proteins or biologically active fragments thereof or molecules containing those enzymes. Furthermore, non-native proteins may be derived from a naturally occurring protein, e.g., from a GH61 or CBM33 family protein.

Such fragments are preferably at least 200, 300 or 400 amino acids in length and preferably comprise simple, short deletions from the N or C terminal, e.g., a C terminal deletion of 1, 2, 3, 4 or 5 amino acids.

All such variants or fragments must retain the functional property of the protein from which they are derived such that they are "biologically active". Thus they must retain oxidohydrolytic activity, e.g., under the conditions described in the Examples (e.g., exhibit enhanced activity when used in the presence of a reducing agent and one or more saccharolytic enzymes when compared to performing the method without the reducing agent, see, e.g., FIG. 4). Furthermore, said biologically active fragments and variants must be able to enhance degradation as described herein, i.e., enhance degradation of the polysaccharide substrate (e.g., when said degradation is performed in the presence of one or more saccharolytic enzymes) when used in the presence of a reducing agent and a divalent metal ion, relative to degradation omitting the reducing agent and divalent metal ion. Some loss of activity is contemplated, e.g., the biologically active fragment or variant may have at least 50, 60, 70, 80, 90 or 95% of the oxidohydrolytic activity of the native full length sequence wherein said activity may be assessed in terms of the extent or level of degradation, e.g., hydrolysis, achieved over a set time period, e.g., as assessed by the production of reaction products such as oligo and/or di-saccharides.

Variants include or comprise naturally occurring variants of the oxidohydrolytic enzymes described above such as comparable proteins or homologues found in other species or more particularly variants found within other microorganisms, which have the functional properties of the enzymes as described above.

Variants of the naturally occurring oxidohydrolytic enzymes as defined herein can also be generated synthetically, e.g., by using standard molecular biology techniques that are known in the art, for example standard mutagenesis techniques such as site directed or random mutagenesis. Such variants further include or comprise proteins having at least 70, 80, 85, 90, 91, 92, 93, 94, 95, 96, 97, 98 or 99% sequence similarity or identity with a naturally occurring oxidohydrolytic enzyme at the amino acid level.

Thus in a preferred aspect the oxidohydrolytic enzyme for use in the methods described herein is a polypeptide which comprises an amino acid sequence as set forth in any one of SEQ ID NOs: 1 to 14 (e.g., SEQ ID NOs: 1-4 or 1-5) and/or 15 to 16 (optionally with or without the leader peptide, where present) or a sequence with at least 30, 40, 50, 60, 70, 80, 90, 95, 97, 98 or 99% sequence identity thereto or a biologically active fragment thereof comprising at least 100 amino acids (preferably at least 200 or 300 amino acids) of said sequence.

In the sequences below, the leader peptides, where present, are underlined.

GH61E from *T. terrestris* (Acc. No. ACE10234)
SEQ ID NO: 1
MLANGAIVFLAAALGVSGHYTWPRVNDGADWQQVRKADNWQDNGYVGDVT

SPQIRCFQATPSPAPSVLNTTAGSTVTYWANPDVYHPGPVQFYMARVPDG

EDINSWNGDGAVWFKVYEDHPTFGAQLTWPSTGKSSFAVPIPPCIKSGYY

LLRAEQIGLHVAQSVGGAQFYISCAQLSVTGGGSTEPPNKVAFPGAYSAT

DPGILINIYYPVPTSYQNPGPAVFSCMLANGAIVFLAAALGVSGHYTWPR

VNDGADWQQVRKADNWQDNGYVGDVTSPQIRCFQATPSPAPSVLNTTAGS

TVTYWANPDVYHPGPVQFYMARVPDGEDINSWNGDGAVWFKVYEDHPT

FGAQLTWPSTGKSSFAVPIPPCIKSGYYLLRAEQIGLHVAQSVGGAQFYI

SCAQLSVTGGGSTEPPNKVAFPGAYSATDPGILINIYYPVPTSYQNPGPA

VFSC

GH61A from *T. aurantiacus* (Acc. No. ABW56451)
SEQ ID NO: 2
MSFSKIIATAGVLASASLVAGHGFVQNIVIDGKKYYGGYLVNQYPYMSNP

PEVIAWSTTATDLGFVDGTGYQTPDIICHRGAKPGALTAPVSPGGTVELQ

WTPWPDSHHGPVINYLAPCNGDCSTVDKTQLEFFKIAESGLINDDNPPG

IWASDNLIAANNWTVTIPTTIAPGNYVLRHEIIALHSAQNQDGAQNYP

QCINLQVTGGGSDNPAGTLGTALYHDTDPGILINIYQKLSSYIIPGPPLY

TG

GH61B from *T. terrestris* (Acc. No. ACE10231)
SEQ ID NO: 3
MKSFTIAALAALWAQEAAAHATFQDLWIDGVDYGSQCVRLPASNSPVTNV

ASDDIRCNVGTSRPTVKCPVKAGSTVTIEMHQQPGDRSCANEAIGGDHYG

PVMVYMSKVDDAVTADGSSGWFKVFQDSWAKNPSGSTGDDDYWGTKDLN

SCCGKMNVKIPEDIEPGDYLLRAEVIALHVAASSGGAQFYMSCYQLTVTG

SGSATPSTVNFPGAYSASDPGILINIHAPMSTYVVPGPTVYAGGSTKSAG

SSCSGCEATCTVGSGPSATLTQPTSTATATSAPGGGGSGCTAAKYQQCGG

TGYTGCTTCASGSTCSAVSPPYYSQCL

CBP21 of *Serratia marescens*
SEQ ID NO: 4
MNKTSRTLLSLGLLSAAMFGVSQQANAHGYVESPASRAYQCKLQLNTQCG

SVQYEPQSVEGLKGFPQAGPADGHIASADKSTFFELDQQTPTRWNKLNLK

TGPNSFTWKLTARHSTTSWRYFITKPNWDASQPLTRASFDLTPFCQFNDG

GAIPAAQVTHQCNIPADRSGSHVILAVWDIADTANAFYQAIDVNLSK

In the above sequence (SEQ ID NO: 4), amino acid residues 1 to 27 correspond to the leader peptide that is necessary for secretion of the protein in a natural system and amino acids 28-196 correspond to the mature protein. Using Pfam for domain/module discovery ("The Pfam protein families database" by Finn et al., 2010, *Nucleic Acids Research* Database Issue 38: D211-222), for SEQ ID NO: 4 residues 28-194, i.e., essentially the complete mature protein, are classified as CBM33. Similarly, in relation to the sequence presented in SEQ ID NO: 5, below, the mature protein starts at position 29 (H).

EfCBM33 from *Enterococcus faecalis* (Acc. No. Q838S1)
SEQ ID NO: 5
MKKSLLTIVLAFSFVLGGAALAPTVSEAHGYVASPGSRAFFGSSAGGNLN

TNVGRAQWEPQSIEAPKNTFITGKLASAGVSGFEPLDEQTATRWHKTNIT

TGPLDITWNLTAQHRTASWDYYITKNGWNPNQPLDIKNFDKIASIDGKQE

VPNKVVKQTINIPTDRKGYHVIYAVWGIGDTVNAFYQAIDVNIQ

E7 from *Thermobifida fusca* (Acc. No. Q47QG3)
SEQ ID NO: 6
MHRYSRTGKHRVVTVRALAVLFTALLGLTQVVTAPASAHGSVINPATRNY

GCWLRWGHDHLNPNMQYEDPMCWQAWQDNPNAMWNWNGLYRDWVGGNHR

AALPDGQLCSGGLTEGGRYRSMDAVGPWKTTDVNNTFTIHLYDQASHGAD

YFLVYVTKQGFDPTTQPLTWDSLELVHQTGSYPPAQNIQFTVHAPNRSGR

HVVFTIWKASHMDQTYYLCSDVNFV

CelS2 from *Streptomyces coeficolor* A3(2) (Acc. No. Q9RJY2)
SEQ ID NO: 7
MVRRTRLLTLAAVLATLLGSLGVTLLLGQGRAEAHGVAMMPGSRTYLCQLDAKTGTGALDPTNPACQAALDQSGATALYNWFAV

LDSNAGGRGAGYVPDGTLCSAGDRSPYDFSAYNAARSDWPRTHLTSGATI

PVEYSNWAAHPGDFRVYLTKPGWSPTSELGWDDLELIQTVTNPPQQGSPG

TDGGHYYWDLALPSGRSGDALIFMQWVRSDSQENFFSCSDVVFDGGNG

EVTGIRGSGSTPDPDPTPTPTDPTTPPTHTGSCMAVYSVENSWSGGFQGS

VEVMNHGTEPLNGWAVQWQPGGGTTLGGVWNGSLTSGSDGTVTVRNVDH

NRVVPPDGSVTFGFTATSTGNDFPVDSIGCVAP

The signal peptide for the proteins in SEQ ID NOs: 1, 2, 3, 4, 5, 6 and 7 is underlined. The two conserved histidines in the metal binding motif of these proteins are shown in bold formatting. The signal peptides and histidines are similarly shown for SEQ ID Nos: 8-14, below.

Cfla_0175 from *Cellulomonas flavigena* DSM 20109
SEQ ID NO: 8
MPRHRSTRRALAGLAATAVVTTALVTVPTVAQAHGGLTNPPTRTYACYQ

DGLAGGAAAGEAGNIRPRNAACVNAFDNEGNYSFYNWYGNLLGTIAGRH

ETIADGKVCGPDARFASYNTPSSAWPTTKVTPGQTMTFQYAAVARHPGW

FTTWITKDGWNQNEPIGWDDLEPAPFDRVLDPPLREGGPAGPEYWWNVK

LPSNKSGKHVLFNIWERTDSPESFYNCVDVDFGGGGTVTPSPTPSVTPT

RTPTPSPTPSVTPSPTPSVTPTPTPTPTPSPTPTLTVTPTPTPTSVP

GDSVCELEVDTSSAWPGGFQGTVTVFNATMEPVNGWQVSWKFTNGETIA

QSWSGVTSQSGSTVTVKNADWNSTIAHHNAVNFGFIGSGTPKAVTDATL

NGKPCIVR

Cfla_0172 from *Cellulomonas flavigena* DSM 20109
SEQ ID NO: 9
MFIPTRSRFGRLARLALAVPLALAATGIVATSASAHGSVTDPPSRNYGC

WEREGGTHMDPAMAQRDPMCWQAFQANPNTMWNWNGNFREGVGGRHEQV

IPDDQLCSAGKTQNGLYASLDTPGPWIMKTVPHNFTLTLTDGAMHGADY

MRIYVSKAGYDPTTDPLGWDDIELIKETGRYGTTGLYQADVSIPSNRTG

RAVLFTIWQASHLDQPYYICSDININGTAPTQQPTQQPTQQPTQQPTQQ

PTQQPTQQPTQQPTQQPTQQPTQNPGTGACTATVKAASTWGNGWQGEVT

VTAGSSAINGWKVTVGGASITQAWSGSYSGGTFSNAEWNGKLAAGASTT

AGFIASGTPGTLTATCTAA

Cfla_0316 from *Cellulomonas flavigena* DSM 20109
SEQ ID NO: 10
MSRISPLRRVAAACGALAIGAATVVGSIALAAPASAHGAVSDPPSRIYG

CWERWASNFTDPAMATSDPQCWDAWQSEPQAMWNWNGMFKEGAAGQHEQ

SIPDGKLCSADNPLYAAADDPGPWRTTPVDHDFRLTLHDPSNHGADYLK

IYVTKQGYDARSEALTWADLELVKTTGRYATSSPYVTDVSVPRDRTGHH

VVFTIWQASHLDQPYYQCSDVTFGGGGTPTTSPTTPAPTPTTPAPTTPA

PTPTTPAPTTPAPTTPAPTTPAPTTPAPTQPADGACTAAIEVVSAWQGG

YQATVTVTAGSGGLDGWTVTVPGATITQAWNGTATGSTITAAGWNGTVA

AGGTAGVGFLGSGSPDGLTATCAAA

Cfla_0490 from *Cellulomonas flavigena* DSM 20109
SEQ ID NO: 11
MRSHALPRSARPTPGRLLLSVLAVIALAFAVLTVAPAPSAQAHGWISDP

PSRQDLCYTGAVSNCGPVMYEPWSVEAKKGSMQCSGGGRFTELDNESRS

WPRQNLKTNQVFTWDIVANHSTSTWEYFVDGRLHTTIDDKGALPPNRFT

HTINNLPEGNHKIFVRWNIADTVNAFYQCIDAYITPGGTPGPTQQPTQQ

PTQQPTQQPTQQPTQQPTQQPTQQPGNGACTATFKTNNAWGNGYQEIT

VTAGSSAIRGWKVTVNGATITQAWSSQLSGSTLSNASWNGSLNAGASTT

LGFIANGTPSGVTATCAAA

CJA_2191 (Cbp33A) from *Cellvibrio japonicus* Ueda107
SEQ ID NO: 12
MFNTRHLLAGVSQLVKPASMMILAMASTLAIHEASAHGYVSSPKSRVIQ

CKENGIENPTHPACIAAKAAGNGGLYTPQEVAVGGVRDNHDYYIPDGRL

CSANRANLFGMDLARNDWPATSVTPGAREFVWTNTAAHKTKYFRYYITP

QGYDHSQPLRWSDLQLIHDSGPADQEWVSTHNVILPYRTGRHIIYSIWQ

RDWDRDAAEGFYQCIDVDFGNGTGTGSSSSVASSVVSSVTSSSVASSVA

SSLSNDTCATLPSWDASTVYTNPQQVKHNSKRYQANYWTQNQNPSTNSG

QYGPWLDLGNCVTSGGSSSVASSSVASSVASSVTSSVASSVVSGNCISP

VYVDGSSYANNALVQNNGSEYRCLVGGWCTVGGPYAPGTGWAWANAWEL

VRSCQ

CJA_3139 (Cbp33/10B) from *Cellvibrio japonicus* Ueda107
SEQ ID NO: 13
MNNKFVKMGGMGALLLAFSALSFGHGFVDSPGARNYFCGAVTKPDHVMN

GVARYPECAGAFANDFNGGYSMSVLTHHQGRKVLGPVARNVCGFDSET

WNGGKTPWDNAINWPVNNINSGTLTFSWDISNGPHFDDTSDFRYWITKP

GFVYQVGRELTWADFEDQPFCDLAYNDDNPGAYPNVRADKPNTHFHTTC

TVPARTGRHVIYAEWGREPPTYERFHGCIDVQIGGGSNSSVPVSSSSSS

RSSSSSSLAPSSSSRSSSSSSSVSSSRSSSSSVVSSSSSSRPASSSSSS

TGGSTEYCNWYGWQVAICKNTTSGWSNENQQTCIGRDTCNAPR

-continued

SCO1734 from *Streptomyces coelicolor* A3(2)
SEQ ID NO: 14

MPAPSASRRAAAVAVAGLAPLALTTLAAAPASAHGSMGDPVSRVSQCHA

EGPENPKSAACRAAVAAGGTQALYDWNGIRIGNAAGKHQELIPDGRLCS

ANDPAFKGLDLARADWPATGVSSGSYTFKYRVTAPHKGTFKVYLTKPGY

DPSKPLGWGDLDLSAPVATSTDPVASGGFYTFSGTLPERSGKHLLYAVW

QRSDSPEAFYSCSDVTFGGDGDGDGDGGSGSGAATGDDTASGDAEAGAA

PAPEASAPSEEQLAAAAEKSTIEHHGHGDQDAATTTDPTDPAAAPEEAP

GTAAEPHQVKAAGGGTENLAETGGDSTTPYIAVGGAAALALGAAVLFAS

VRRRATTGGRHGH

SEQ ID NOs: 15 and 16 are shown without a leader peptide. The two conserved histidines in the metal binding motif of these proteins are shown in bold formatting.

HjGH61A from *Hypocrea jecorina*
SEQ ID NO: 15

HGHINDIVINGVWYQAYDPTTFPYESNPPIVVGWTAADLDNGFVSPDA

YQNPDIICHKNATNAKGHASVKAGDTILFQWVPVPWPHPGPIVDYLANC

NGDCETVDKTTLEFFKIDGVGLLSGGDPGTWASDVLISNNNTWVVKIPD

NLAPGNYVLRHEIIALHSAGQANGAQNYPQCFNIAVSGSGSLQPSGVLG

TDLYHATDPGVLINIYTSPLNYIIPGPTVVSGLPTSVAQGSSAATATAS

ATVPGGGSGPTSRTTTTARTTQASSRPSSTPPATTSAPAGGPTQTLYGQ

CGGSGYSGPTRCAPPATCSTLNPYYAQCLN

HjGH61 from *Hypocrea jecorina*
SEQ ID NO: 16

HGQVQNFTINGQYNQGFILDYYYQKQNTGHFPNVAGWYAEDLDLGFISP

DQYTTPDIVCHKNAAPGAISATAAAGSNIVFQWGPGVWPHPYGPIVTYV

VECSGSCTTVNKNNLRWVKIQEAGINYNTQVWAQQDLINQGNKWTVKIP

SSLRPGNYVFRHELLAAHGASSANGMQNYPQCVNIAVTGSGTKALPAGT

PATQLYKPTDPGILFNPYTTITSYTIPGPALW

When variants are generated, it should be noted that appropriate residues to modify depend on the properties that are being sought in such a variant. In the case that a variant having the same oxidohydrolytic activity as the native parent molecule is being sought, the residues are in general those residues that are not involved in the catalytic reaction or interaction of the enzyme with the chitin substrate. However, those residues may be targeted, in the alternative, to develop variants with improved reactivity. This could be achieved by standard protein engineering techniques or by techniques based on random mutagenesis followed by screening, all techniques that are well known in the art. Attempts to improve the function of oxidohydrolytic enzymes may include improving the binding and catalytic ability of the enzyme, e.g., to act on other substrates, e.g., carbohydrate containing copolymers, e.g., protein-carbohydrate copolymers.

A person skilled in the art will recognize the potential of using the native proteins' framework to create variants that are optimised for other insoluble polymeric polysaccharide substrates (e.g., other forms of chitin or cellulose), or insoluble carbohydrate-containing copolymers.

In the case of GH61 proteins as set forth in SEQ ID NOs: 1, 2 and 3 (and 15-16), preferably the residues at positions 19, 86, 169, 171 and 210 of SEQ ID NO: 1 are conserved (see Harris et al., 2010, *Biochemistry* 49:3305-3316, in which His-1 of the mature protein appears at position 19) or the corresponding residues in other GH61 proteins. Such corresponding residues can easily be found by sequence alignment.

In the case of CBP21, several residues have been shown to be important in the binding of CBP21 to chitin and more specifically to the ability of CBP21 to enhance the degradation of chitin (Vaaje-Kolstad et al., 2005, *J. Biol. Chem.* 280: 11313-11319 and 28492-28497). Several mutations have been shown not to affect binding, but to affect the ability of CBP21 to enhance the degradation of chitin. These results may be predicted for other CBM33 proteins such as EfCBM33, E7, CelS2, Cfla_0175, Cfla_0172, Cfla_0316, Cfla_0490, CJA_2191 (Cbp33A), CJA_3139 (Cbp33/10B) and SCO1734. These residues are preferably not modified relative to the wild type CBP21 sequence as set out in SEQ ID NO: 4 (or any one of SEQ ID NOs: 5 to 14, e.g., SEQ ID NO: 5), if the aim is to modify, e.g., the stability of the CBP (for example under process conditions), but these residues may be targeted if one's aim is to improve or change the CBP21's functional properties.

Preferred variants of CBP21 retain one or more and preferably all of: a tyrosine residue at position 54, a glutamic acid residue at position 55, a glutamic acid residue at position 60, a histidine residue at position 114, an aspartic acid residue at position 182 and an asparagine at position 185 (sequence numbering according to SEQ ID NO: 4).

In connection with amino acid sequences, "sequence similarity", preferably "sequence identity", refers to sequences which have the stated value when assessed using, e.g., using the SWISS-PROT protein sequence databank using FASTA pep-cmp with a variable pamfactor and gap creation penalty set at 12.0 and gap extension penalty set at 4.0 and a window of 2 amino acids). Sequence identity at a particular residue is intended to include identical residues which have simply been derivatized. Sequence identity assessments are made with reference to the full length sequence of the recited sequence used for comparison.

Preferred "variants" include those in which instead of the naturally occurring amino acid the amino acid which appears in the sequence is a structural, e.g., non-native analogue thereof. Amino acids used in the sequences may also be derivatized or modified, e.g., labelled, glycosylated or methylated, providing the function of the oxidohydrolytic enzyme is not significantly adversely affected.

Further preferred variants are those in which relative to the above described amino acid sequences, the amino acid sequence has been modified by single or multiple amino acid (e.g., at 1 to 10, e.g., 1 to 5, preferably 1 or 2 residues) substitution, addition and/or deletion or chemical modification, including deglycosylation or glycosylation, but which nonetheless retain functional activity, insofar as they bind to the polysaccharide substrate and enhance its degradation, particularly when used in conjunction with one or more saccharolytic enzymes.

Within the meaning of "addition" variants are included amino and/or carboxyl terminal fusion proteins or polypeptides, comprising an additional protein or polypeptide or other molecule fused to the enzyme sequence. Carboxyl terminal fusions are preferred. It must be ensured that any such fusion to the enzyme does not adversely affect the functional properties required for use in the methods of the invention as set out elsewhere herein.

"Substitution" variants preferably involve the replacement of one or more amino acids with the same number of amino acids and making conservative substitutions.

Such functionally-equivalent variants mentioned above include in particular naturally occurring biological variations (e.g., found in other microbial species) and derivatives prepared using known techniques. In particular functionally equivalent variants of the oxidohydrolytic enzymes described herein extend to enzymes which are functional in (or present in), or derived from different genera or species than the specific molecules mentioned herein.

Variants such as those described above can be generated in any appropriate manner using techniques which are known and described in the art, for example using standard recombinant DNA technology.

Preferably the variants or fragments described herein are derived from the native sequences set forth above, particularly those of any one of SEQ ID NOs: 1 to 14 (e.g., SEQ ID NOs: 1-4 or 1-5) and/or 15 to 16.

As referred to herein a "reducing agent" is an element or compound in a redox (reduction-oxidation) reaction that reduces another species and in so doing becomes oxidized and is therefore the electron donor in the redox reaction. Preferably the reducing agent is non-enzymatic. In this particular invention, the reduced compound is oxygen which by the reduction becomes activated, enhancing the oxidohydrolytic function of, e.g., GH61 or CBM33 proteins. The reducing agent may function as an electron donor in the enzymatic process and it is possible that electron donation takes place via the generation of reactive oxygen species such as $O_2^-$. The reducing agent promotes electron donation and/or the generation of reactive oxygen. Preferably said reducing agent is ascorbic acid, reduced glutathione or $Fe(II)SO_4$. Further preferred reducing agents are $LiAlH_4$ and $NaBH_4$. Other preferred reducing agents include organic acids (such as succinic acid, gallic acid, coumaric acid, humic acid and ferulic acid) and reducing sugars (such as glucose, glucosamine and N-acetylglucosamine), Alternatively, lignin, which contains reducing groups, or fragments thereof, may be used as the reducing agent. As noted above, $Fe(II)SO_4$ may be used as a reducing agent and in so doing will also contribute the required divalent metal ion. Whilst a single compound may provide both the reducing agent and metal ion, it is preferred that these features are provided by different compounds, i.e., that the reducing agent and metal ion are separate compounds.

More than one of such agents may be used in line with methods of the invention and may be selected according to the substrate and conditions used (e.g., pH and temperature). It will be appreciated that the efficacy and stability of reducing agents varies between these agents and depends on pH. Thus the pH and reducing agent should be optimized for the oxidohydrolytic enzyme to be used.

Preferably said divalent metal ion is Ca, Co, Mg, Mn, Ni or Zn. In an alternative embodiment the divalent metal ion is Cu. Thus, for example salts such as $MgCl_2$, $ZnCl_2$ or $CoCl_2$ (or alternatively $CuCl_2$) may be used.

The following description sets out conditions that can be used for performance of the method of the invention, but it should be noted that any appropriate conditions can be used.

Prior to contacting the polysaccharide-containing material with the oxidohydrolytic enzyme, the polysaccharide-containing material may be pre-treated.

The polysaccharide-containing material may be pre-treated, e.g., to disrupt plant cell wall components, using conventional methods known in the art. Prior to pre-treatment, where appropriate, the polysaccharide-containing material may be subjected to pre-soaking, wetting, or conditioning using methods known in the art. Physical pre-treatment techniques include, for example, various types of milling, irradiation, steaming/steam explosion and hydrothermolysis; chemical pre-treatment techniques can include dilute acid, alkaline (e.g., lime pre-treatment), organic solvent (such as organosolv pre-treatments), ammonia treatments (e.g., ammonia percolation (APR) and ammonia fibre/freeze explosion (AFEX)), sulfur dioxide, carbon dioxide, wet oxidation and pH-controlled hydrothermolysis; and biological pre-treatment techniques can involve applying lignin-solubilizing microorganisms (see, for example, Hsu, 1996, Pre-treatment of biomass, in "Handbook on Bioethanol: Production and Utilization", Wyman, ed., Taylor & Francis, Washington, D.C., 179-212; Ghosh & Singh, 1993, *Adv. Appl. Microbiol.* 39: 295-333; McMillan, 1994, Pre-treating lignocellulosic biomass: a review, in "Enzymatic Conversion of Biomass for Fuels Production", Himmel et al. eds., ACS Symposium Series 566, American Chemical Society, Washington, D.C., Chapter 15; Gong et al., 1999, Advances in Biochemical Engineering/Biotechnology, Scheper, ed., Springer-Verlag Berlin Heidelberg, Germany, 65: 207-241; Olsson & Hahn-Hagerdal, 1996, *Enz. Microb. Tech.* 18: 312-331; and Vallander & Eriksson, 1990, *Adv. Biochem. Eng./Biotechnol.* 42: 63-95). Additional pre-treatments include ultrasound, electroporation, microwave, supercritical $CO_2$, supercritical $H_2O$ and ammonia percolation.

Pre-treated corn stover is a cellulose-containing material derived from corn stover, e.g., by treatment with heat and dilute acid.

Following optional pre-treatment, the polysaccharide-containing material (the substrate) may be exposed to the oxidohydrolytic enzyme in vitro in any appropriate vessel, e.g., by mixing together the substrate and the enzyme in an appropriate medium (e.g., a solution, such as an aqueous solution) or by applying the enzyme to the substrate (e.g., by applying the enzyme in a solution to a substrate).

In a preferred embodiment the oxidohydrolytic enzyme is present in a buffer such as a phosphate buffer, e.g., a sodium phosphate buffer, or Tris buffer. Suitable concentration ranges for such a buffer are 1-100 mM. The oxidohydrolytic enzyme may be provided as a purified preparation (as described hereinafter) or may be present in a composition, wherein it may be a major component, preferably comprising at least 20, 30, 40, 50, 60 or 70% w/w dry weight in the composition, or it may be a minor component (e.g., in a mixture with one or more saccharolytic enzymes), preferably comprising at least 1, 2, 5 or 10%, e.g., 1-5%, w/w dry weight in the composition.

The enzyme can be present in the solution at any suitable concentration, such as a concentration of 0.001-1.0 mg/ml, e.g., 0.01-0.1 mg/ml or 0.05-0.5 mg/ml.

The polysaccharide substrate is present in the reaction mix at any suitable concentration which will depend to some extent on the purity of the polysaccharide in the material containing it. Conveniently, however, the polysaccharide itself is present at a concentration of from 0.1 to 200 mg/ml, preferably 0.2 to 20 mg/ml or 0.5 to 50 mg/ml, or more preferably 25 to 150 mg/ml, especially preferably at least 25 mg/ml. Preferably the polysaccharide is present in the material containing the polysaccharide to a level of >50%, e.g., >60, 70, 80 or 90%, w/w dry weight in the material.

Preferably the polysaccharide substrate is exposed to the enzyme, e.g., by incubation together, for a period of 4, 6, 12 or 24 hours or more, such as 4-24 or 6-24 hours, e.g., 36 or 48 hours or more, or 3, 4, 5, 6, 7, 8, 9, 10, 11, 12, 13, 14 days or more. In a preferred aspect the incubation is 6-24 hours. This incubation is in general carried out at or about 50° C., although appropriate temperatures for optimizing the enhancement of polysaccharide degradation can readily be determined by the skilled person in the art. For example, the temperature can be in the range of 20-65° C., e.g., 30-60° C., preferably 50-55° C.

It will be appreciated that the necessary incubation times, pH, temperature, substrate and enzyme concentrations are not independent of each other. Thus, a large range of conditions can be envisaged, which can easily be evaluated. The oxidohydrolytic enzymes serve to enhance degradation by the saccharolytic enzymes and thus may allow the use of lower concentrations of the latter or shorter reaction times.

Preferably a pH in the range of 4 to 9 is used. Preferably the pH is in the range of 5 to 8. The preferred pH is about pH 5-6.

Where a reducing agent is used, the reducing agent is preferably added for the duration of the degradation reaction, though it may be added after that reaction has commenced and may be present only while the oxidohydrolytic enzyme is present or active. Reducing agents are preferably added to a final concentration range of 0.1 to 100 mM, preferably 0.5 to 20 mM, especially preferably 1-5 mM. Reducing agents may be present in the polysaccharide substrate, e.g., lignin present in a lignocellulosic biomass, but preferably said reducing agents are added to the reaction mix.

As with the reducing agent, the metal ion may be added at the start or during the degradation reaction. However, it may not always be necessary to add metal ions to the reaction mixture as some substrate-containing material may contain sufficient metal ions for the reaction to proceed successfully. However, in a preferred aspect, metal ions are added to the reaction mix. In one embodiment, the metal ion may be added to the oxidohydrolytic enzyme during its production or isolation or to the enzyme prior to its addition to the reaction mix such that the enzyme is "pre-loaded" with the relevant metal ion. Metal ions are preferably added to a final concentration range of 0.001 to 50 mM, e.g., 0.01 to 50 mM, preferably 0.1 to 5 mM. The concentration to be used may be readily determined for the particular metal ion to be used in the reaction mix. For example, lower concentrations of $Cu^{2+}$ (e.g., 0.001 to 0.1 mM) may be appropriate relative to the concentration required for other metal ions. It will be appreciated that the optimal metal ion concentrations to some extent depend on the enzyme and substrate concentrations used in the enzymatic conversion reactions that are set up.

As noted herein, the oxidohydrolytic enzymes are believed to catalyze hydrolysis by oxidation by molecular oxygen. It is therefore imperative (as noted in the Examples) that molecular oxygen is available for use in the reaction. As such any conditions that result in an oxygen-free (anaerobic) environment must be avoided.

Thus, in a preferred aspect the method comprises contacting said polysaccharide with an oxidohydrolytic enzyme and adding at least one reducing agent and preferably at least one divalent metal ion to the reaction mixture.

Preferably the incubation is carried out with agitation, particularly when a cellulose-containing material is used.

In a preferred aspect, the oxidohydrolytic enzyme is used at a concentration of 0.01 to 0.5 mg/ml and the polysaccharide substrate at 25 to 150 mg/ml (when calculated according to the target substrate content and not taking into account the additional material that may be present with the substrate) and the reaction is conducted at pH 5-8 for 6 to 24 hours at 50 to 55° C.

In methods in which the degradation or hydrolysis is carried out with the oxidohydrolytic enzyme only, the result of said reaction is incomplete degradation of the polysaccharide to yield largely insoluble long oligosaccharides and minor fractions of soluble oligosaccharides, perhaps including very minor fractions of disaccharides. Preferably said degradation or hydrolysis is enhanced further or completed by the use of appropriate additional degradative glycoside hydrolases.

Thus in a further preferred aspect the present invention provides a method of degrading or hydrolyzing a polysaccharide comprising:

a) contacting said polysaccharide with one or more oxidohydrolytic enzymes, wherein said degradation or hydrolysis is carried out in the presence of at least one reducing agent and at least one divalent metal ion, and b) contacting said polysaccharide (or the degradation or hydrolysis product thereof) with one or more saccharolytic enzymes selected from a cellulose hydrolase or chitin hydrolase.

Clearly in performing the method the oxidohydrolytic enzyme and the saccharolytic enzyme must be selected in accordance with the polysaccharide substrate, e.g., GH61 and a cellulose hydrolase for cellulose and CBP21 or another CBM33 family protein and a chitin hydrolase for chitin. Cross-reaction between different substrates may also be possible, e.g., CBM33 family proteins may be effective as oxidohydrolytic enzymes on cellulose, e.g., SEQ ID NO: 5 (EfCBM33) and other CBM33 proteins described herein may be used in methods of the invention performed on cellulose. Similarly, GH61 family members may be used on substrates other than cellulose, e.g., chitin or hemicellulose.

Until now enzyme activity of members of the CBM33 family has only been reported for chitin as a substrate (e.g., CBP21 from *Serratia marcescens*). However, the present invention demonstrates that members of the CBM33 family, e.g., E7 and CelS2, work on cellulose. The enzymatic function entails hydrolysis (cleavage) and oxidation of cellulose chains in insoluble cellulose crystals, which enables a more rapid deconstruction of the cellulose by cellulases. CBM33 enzymes acting on cellulose work optimally in the presence of an external electron donor (e.g., a reducing agent) and divalent metal ions. These enzymatic traits are highly similar to those observed previously for CBM33 enzymes that act on chitin. In the experiments described herein a single domain CBM33 from *Thermobifida fusca* (Uniprot ID: Q47QG3; E7) and a multidomain CBM33 (Uniprot ID: Q9RJY2; a CBM33 with a CBM2 attached on the C-terminal side of the protein; CelS2) from *Streptomyces coelicolor* A3(2) were expressed and purified and their ability to potentate cellulose degrading enzyme activity was observed.

CBM33 proteins for reaction with cellulose are preferably obtained from cellulolytic bacteria, e.g., bacteria of the genera *Cellulomonas, Cellvibrio, Thermobifida* or *Streptomyces*, e.g., bacteria of the species *Cellulomonas flavigena, Cellvibrio japonicus, Thermobifida fusca* or *Streptomyces* spp. (preferably E7 and CelS2 as disclosed herein and Cfla_0175, Cfla_0172, Cfla_0316, Cfla_0490, CJA_2191 (Cbp33A), CJA_3139 (Cbp33/10B) and SCO1734) and/or have one or more cellulose binding modules (e.g., belonging to CBM family 2) attached to the C-terminal end.

Natural or engineered variants of these oxidohydrolytic enzymes with altered substrate specificity (e.g., from chitin to cellulose) may be combined with other substrates and saccharolytic enzymes.

It will be obvious to the expert in the field that polysaccharides such as chitin and, especially, cellulose may occur in complex co-polymeric matrices including for example hemicelluloses in the case of plant cell wall material. Since cellulose and hemicelluloses interact strongly, it is possible that loosening of the cellulose structure by an oxidohydrolase may make not only the cellulose but also the hemicellulose more accessible for attack by appropriate saccharolytic enzymes. Thus, oxidohydrolases such as GH61 and CBM33 family proteins may also be used concomitantly with, e.g., hemicellulases or other enzymes targeting the non-chitin and non-cellulose polymers in complex chitin- or cellulose-containing co-polymeric materials, in order to increase the saccharolytic efficiency of these enzymes.

As referred to herein a "saccharolytic enzyme" is an enzyme which is capable of cleaving glycosidic bonds between saccharide monomers or dimers in a polysaccharide, using a standard hydrolytic mechanism as employed by most enzymes classified in the glycoside hydrolase (GH) families in the CAZy database. These enzymes include cellulose hydrolases, chitin hydrolases and beta-glucosidases.

As referred to herein a "cellulose hydrolase" is an enzyme which hydrolyses cellulose or intermediate breakdown products. Preferably the hydrolase is a cellulase. Cellulases are classified as glycosyl hydrolases (GH) in families based on their degree of identity and fall within the GH families 1, 3, 5-9, 12, 44, 45, 48 and 74. Based on mechanism they can be grouped into exo-1,4-beta-D-glucanases or cellobiohydrolases (CBHs, EC 3.2.1.91), endo-1,4-beta-D-glucanases (EGs, EC 3.2.1.4) and beta-glucosidases (BGs, EC 3.2.1.21). EGs cleave glycosidic bonds within cellulose microfibrils, acting preferentially at amorphous cellulose regions. EGs fragment cellulose chains to generate reactive ends for CBHs, which act "processively" to degrade cellulose, including crystalline cellulose, from either the reducing (CBH1) or non-reducing (CBHII) ends, to generate mainly cellobiose. Cellobiose is a water-soluble beta-1,4-linked dimer of glucose. Beta-glucosidases hydrolyze cellobiose to glucose. GH61 enzymes were previously classified as weak endoglucanases on the basis of activity of one member of the family though this is now not considered correct. As mentioned above, GH61 enzymes have been found to be oxidohydrolytic by the present inventors.

The ability of cellulose hydrolases to hydrolyse cellulose may be assessed by using methods known in the art, including methods in which non-modified cellulose is used as substrate. Activity is then measured by measuring released products, using either HPLC-based methods or methods that determine the number of newly formed reducing ends (e.g., Zhang et al., 2009, *Methods Mol. Biol.* 581:213-31; Zhang et al., 2006, *Biotechnol. Adv.* 24(5): 452-81). In the alternative, the efficacy of the cellulose hydrolase may be assessed by using an appropriate substrate and determining whether the viscosity of the incubation mixture decreases during the reaction. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of the substrate.

Cellulases may be obtained from commercial sources, i.e., companies such as Novozymes, Danisco and Biocatalysts. Examples of commercial cellulases include, for example, CELLIC™ CTec (Novozymes A/S), CELLIC™ CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.).

Alternatively cellulases may be produced using standard recombinant techniques for protein expression. The scientific literature contains numerous examples of the cloning, overexpression, purification and subsequent application of all types of cellulases, e.g., endoglucanases, cellobiohydrolases, and beta-glucosidases.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention include, but are not limited to, a *Trichoderma reesei* endoglucanase I (Penttila et al., 1986, *Gene* 45: 253-263; *Trichoderma reesei* Cel7B endoglucanase I; GENBANK™ accession no. M15665); *Trichoderma reesei* endoglucanase II (Saloheimo, et al., 1988, *Gene* 63:11-22; *Trichoderma reesei* Cel5A endoglucanase II; GENBANK™ accession no. M19373); *Trichoderma reesei* endoglucanase III (Okada et al., 1988, *Appl. Environ. Microbiol.* 64: 555-563; GENBANK™ accession no. AB003694); *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase; *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the present invention include, but are not limited to, *Trichoderma reesei* cellobiohydrolase I; *Trichoderma reesei* cellobiohydrolase II; *Humicola insolens* cellobiohydrolase I; *Myceliophthora thermophila* cellobiohydrolase II; *Thielavia terrestris* cellobiohydrolase II (CEL6A); *Chaetomium thermophilum* cellobiohydrolase I; and *Chaetomium thermophilum* cellobiohydrolase II.

Examples of beta-glucosidases useful in the present invention include, but are not limited to, *Aspergillus oryzae* beta-glucosidase; *Aspergillus fumigatus* beta-glucosidase;

*Penicillium brasilianum* IBT 20888 beta-glucosidase; *Aspergillus niger* beta-glucosidase; and *Aspergillus aculeatus* beta-glucosidase.

Cellulase mixtures may be used, e.g., a cellulase mixture which comprises at least one endoglucanase, e.g., belonging to GH family 5, 7 or 12, a cellobiohydrolase moving towards the reducing end, e.g., belonging to GH family 6, a cellobiohydrolase moving towards the non-reducing end, e.g., belonging to GH family 7, and a beta-glucosidase. More preferably, more complex mixtures are used, in particular mixtures containing several endoglucanases with different substrate specificities (e.g., acting at different faces of the cellulose crystals). Appropriate cellulases may be readily identified taking into account the substrate to be degraded.

As referred to herein a "chitin hydrolase" is an enzyme which hydrolyses chitin or intermediate breakdown products. Preferably said chitin hydrolase is a chitinase, chitosanase or lysozyme. The degradation may be complete or partial. For example, the activity of some chitin hydrolase, e.g., chitinases on chitin substrates is not strong enough to result in complete degradation of the substrate. This is particularly the case for chitinases such as ChiG from *Streptomyces coelicolor* that do not have their own CBM, or chitinases such as ChiB from *S. marcescens*. In this case, the use of a oxidohydrolytic enzyme that acts on chitin in accordance with the present invention can result in enhanced chitin degradation and preferentially result in complete degradation that was not previously possible. Other chitinases, such as ChiC from *S. marcescens*, are capable of completely degrading chitin, but the speed of this process increases upon addition of an oxidohydrolytic enzyme such as CBP21.

Chitinase enzymes are found in plants, microorganisms and animals. Chitinases have been cloned from various species of microorganisms and have been categorised into two distinct families, designated family GH18 and family GH19 of the glycoside hydrolases, based on sequence similarities (Henrissat and Bairoch, 1993, *Biochem, J.* 293:781-788). These enzymes are referred to collectively herein as chitin hydrolases.

There are several ways to measure chitinase activity that are well known in the field, including methods in which non-modified chitin is used as substrate. Activity on non-modified chitin is measured by measuring released products, using either HPLC-based methods or methods that determine the number of newly formed reducing ends.

Chitinases may be obtained from commercial sources, i.e., companies such as Sigma. Alternatively chitinases may be produced using standard recombinant techniques for protein expression. The scientific literature contains numerous examples of the cloning, overexpression, purification and subsequent application of all types of chitinases (e.g., Horn et al., 2006, *FEBS J.* 273(3):491-503 and references therein).

Other suitable hydrolytic enzymes for hydrolyzing additional non-cellulose (or non-chitin) polysaccharides include hemicellulases such as acetylxylan esterases, arabinofurosidases, feruloyl esterases, glucuronidases, mannanases, xylanases, and xylosidases.

The cellulase mixtures may also be used in conjunction with hemicellulases. Hemicellulases may also be obtained from commercial sources. Examples of commercial hemicellulases include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limited, Wales, UK), DEPOL™ 740L (Biocatalysts Limited, Wales, UK), and DEPOL™ 762P (Biocatalysts Limited, Wales, UK).

Examples of xylanases useful in the methods of the present invention include, but are not limited to, *Aspergillus aculeatus* xylanase (GeneSeqP: AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number QOUHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8X211), *Aspergillus niger* alpha-glucuronidase (Uniprot accession number Q96WX9), *Aspergillus terreus* alpha-glucuronidase (SwissProt accession number QOCJP9), and *Aspergillus fumigatus* alpha-glucuronidase (SwissProt accession number Q4WW45).

Whilst the use of native saccharolytic enzymes is preferred, variants defined in accordance with the properties described herein for the oxidohydrolytic enzyme's variants may also be used.

Preferably, when said polysaccharide is cellulose, said saccharolytic enzyme is an endo-1,4-beta-D-glucanase optionally used in combination with other 1,4-beta-D-glucanases such as cellobiohydrolases and/or beta-glucosidases.

Thus, the enzymes to be used in methods of the invention may be selected based on the polysaccharide substrate to be hydrolyzed. For example, CBP21 binds only to beta-chitin and would therefore be an appropriate oxidohydrolytic enzyme to use if the methods of the invention were to be applied to beta-chitin. Similarly ChbB from *B amyloliquifaciens* as described in Chu et al. (supra) may be applied to beta-chitin.

CHB1, CHB2 and CHB3 have all been isolated from *S olivaceovirides* (Svergun et al., Zeltins et al., Schnellman et al., Kolbe et al., Saito et al., supra). The binding preferences of these three proteins have been determined and CHB1 and CHB2 bind preferably to alpha-chitin, whereas CHB3 binds to both alpha- and beta-chitin. CBP1 from *Alteromonas* s described by Tsujibo et al. binds to both alpha- and beta-chitin, with a preference for the alpha form.

Alternatively, GH61 family members, such as described herein, may be used to assist with chitin degradation in methods of the invention.

Similarly when the substrate is chitin, the saccharolytic enzyme can be selected accordingly. The properties of chitinases have been documented (e.g., Hollis et al., 1997, *Arch. Biochem. Biophys*. 344: 335-342 and Suzuki et al., 1998, *Biosci. Biotech. Bioch*. 62: 128-135; Horn et al., 2006).

Preferred combinations for beta-chitin hydrolysis are CBP21 (or variants or fragments thereof) with one or more of ChiA, ChiB, ChiC and ChiG. Preferred combinations for alpha-chitin hydrolysis are CHB1 or CHB2 (or variants or fragments thereof) with one or more of ChiA, ChiB, ChiC and ChiG. Alternatively GH61 family members as described herein may be used with appropriate chitinases.

When the substrate is cellulose, the oxidohydrolytic enzyme is preferably a GH61 family protein (as described herein), though in view of their ability to act on cellulose, CBM33 family proteins may also be used. Appropriate saccharolytic enzymes may be selected from known enzymes, e.g., cellulases as described herein.

In a preferred aspect two or more oxidohydrolytic enzymes are employed in the methods of the invention. In view of their preferred substrate specificities, enhanced degradative effects may be expected when used together. Thus, for example, one may use two or more CBM33 family proteins and/or GH61 family proteins (as described herein), e.g., two or more CBM33 family proteins, two or more GH61 family proteins or a combination of one or more of each of the CBM33 family proteins and GH61 family proteins in the methods (e.g., at least one CBM33 family protein and at least one GH61 family protein). Thus, for example chitin (or cellulose) may be contacted with one CBM33 family protein and one GH61 family protein, e.g., preferably selected from the proteins described herein (e.g., polypeptides which comprise an amino acid sequence as set forth in any one of SEQ ID NOs: 4 and/or 5 and/or 6 to 14 or related sequences or fragments described herein (CBM33 family proteins) and polypeptides which comprise an amino acid sequence as set forth in any one of SEQ ID NOs: 1 to 3 and/or 15 to 16 or related sequences or fragments described herein (GH61 family proteins)).

Appropriate enzymes for use in accordance with the invention can be determined by use of screening techniques to assess in vitro hydrolysis, e.g., as described in the Examples.

To identify oxidohydrolytic enzymes which may be used in combination, the enzymes may be assessed to determine whether their activity will achieve enhanced effects on the substrate. For example, when degrading biomass one may combine members of the CBM33/GH61 families that are known from experiments, such as those described herein, to have different specificities for the various forms of chitin (e.g., alpha-chitin or beta-chitin) or cellulose (e.g., various types of cellulose fibers, cellulose pulps, filter paper, microcrystalline cellulose, AVICEL®, Carboxymethylcellulose) that occur in nature, biomass, and/or pretreated biomass, or can be obtained by chemical modification, many of these forms being easily accessible for experimentation. In biomass, chitin and cellulose often occur as heteropolymers, containing other polysaccharides often referred to as hemicelluloses or even proteins. The different members of the CBM33/GH61 families can be expected to have different activity on these different substrates. Biomass is often heterogeneous, either by nature, or because biomasses are mixed during process development in the factory. By mixing members of the CBM33/GH61 families with known differences in biomass preferences, more efficient processes may be obtained. Further synergies may be obtained using members of the CBM33/GH61 families that preferentially act on different polysaccharides in biomass, such as xylan.

Figures 6A, 6B:
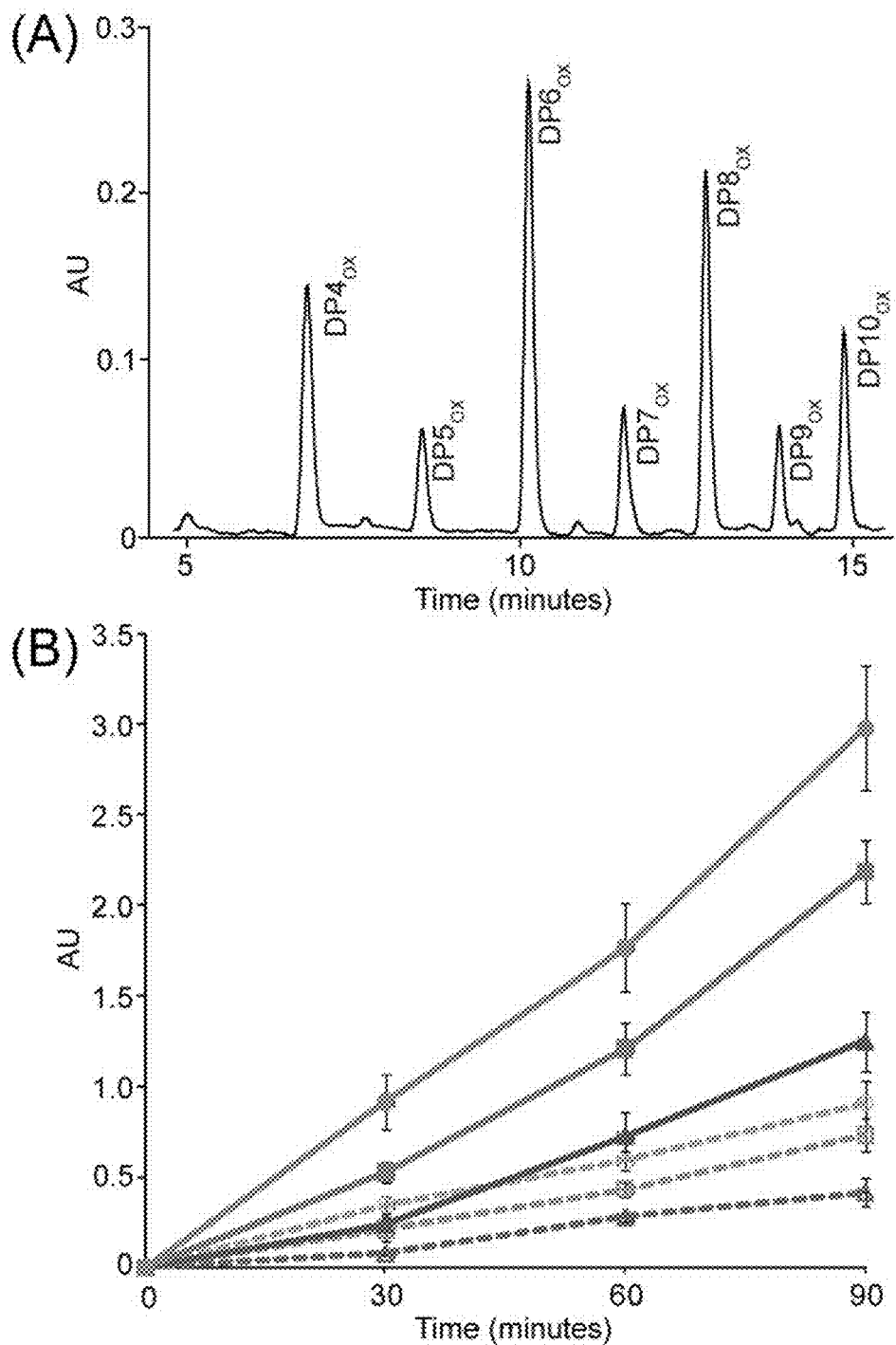
FIGS. 6A and 6B show UHPLC separation of oxidized oligosaccharides with acidic (GlcNAcA) ends. A semi-quantitative analysis of soluble products generated by CBP21 was performed by separating the oxidized oligosaccharides by UHPLC.
Figure 15A:
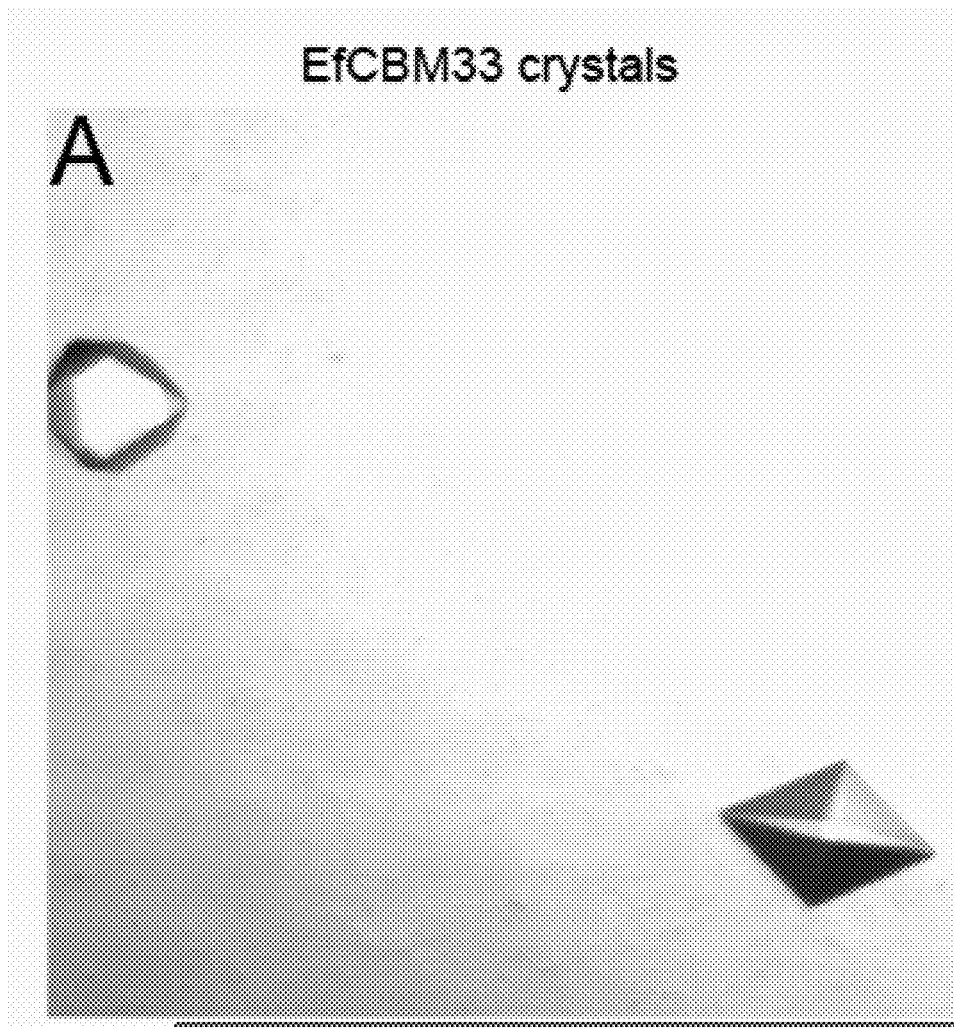
FIG. 15A shows crystals of EfCBM33 (Uniprot ID: Q838S1; EF0362; uniprot.org/uniprot/Q838S1), obtained by hanging drop vapor diffusion experiments that have been used to collect 0.95 Å data.
Figure 15B:
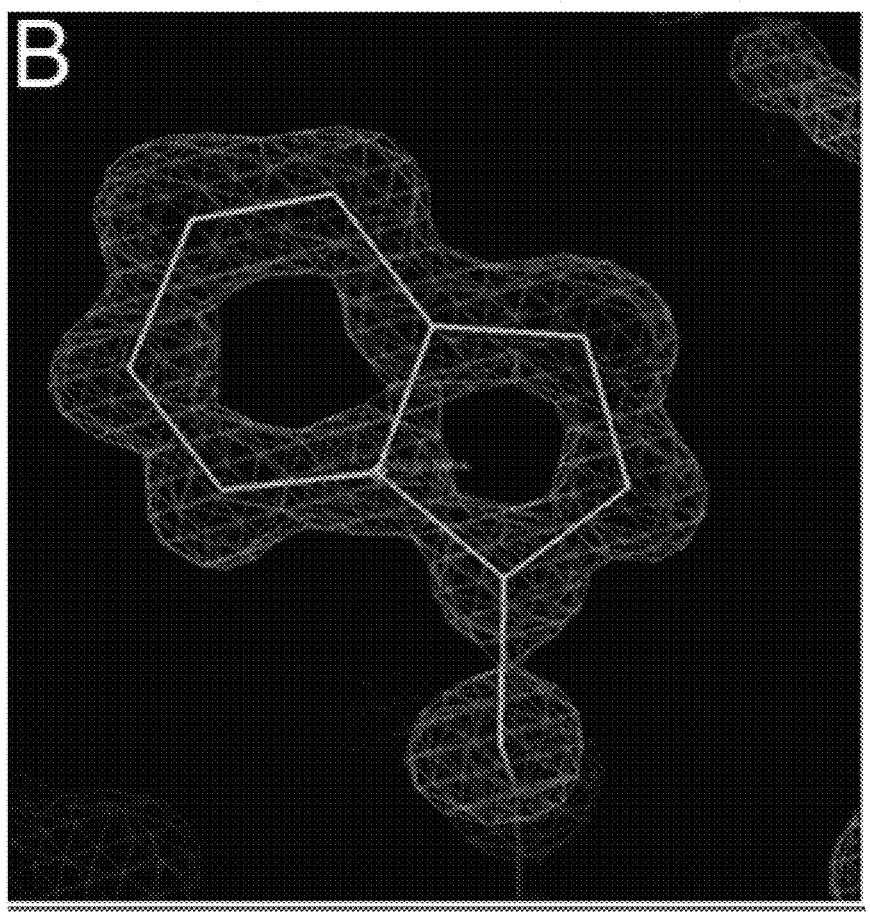
FIG. 15B shows the side chain of the solvent exposed Trp modeled in the 2Fo-Fc map.
Figure 15C:
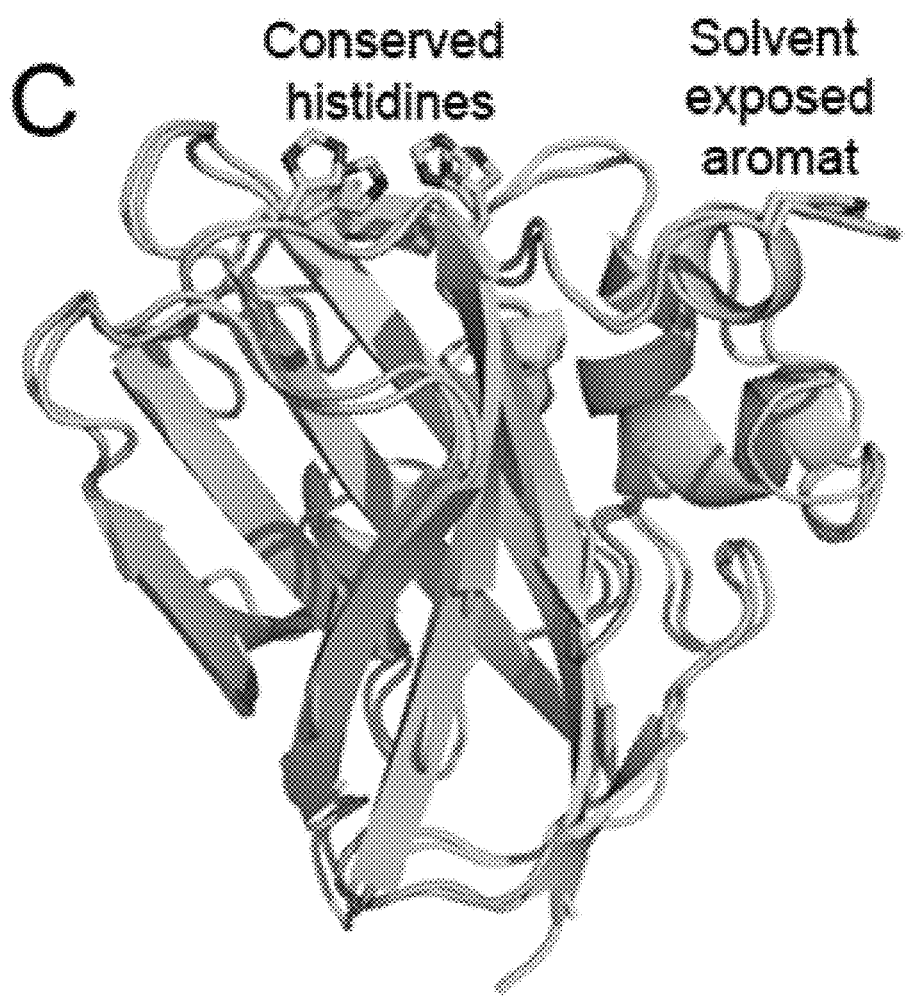
FIG. 15C shows superposition of the main chains of CBP21 and EfCBM33; the side chains of the conserved histidines and a surface exposed aromatic amino acid (Tyr in CBP21, Trp in EfCBM33) are shown.
Figure 15D:
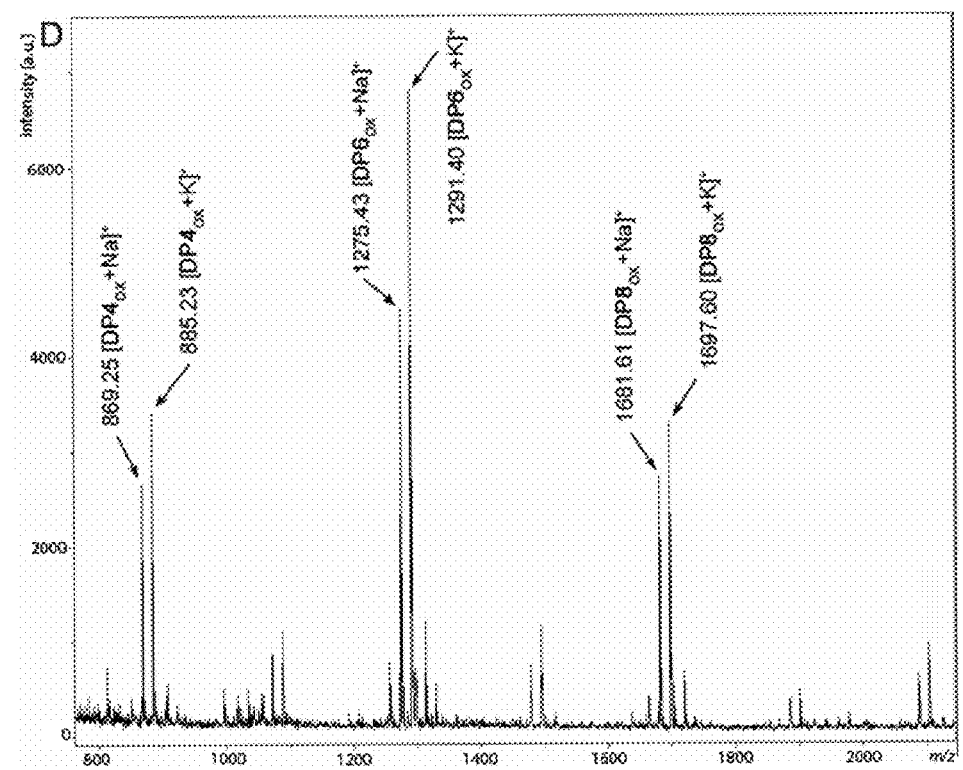
FIG. 15D shows a MALDI-TOF MS spectrum of soluble products obtained after treating 2.0 mg/ml beta-chitin with "washed" EfCBM33 crystals dissolved in 20 mM Tris pH 8.0; as for CBP21, the product spectrum is dominated by even-numbered oxidized chitooligosaccharides, clearly demonstrating oxidohydrolytic activity.

Oxidohydrolytic enzymes with different activities may also be identified by examining the periodicity of the reaction products (see the Examples herein). Thus, a combination may be made between oxidohydrolytic enzymes (e.g., members of the CBM33/GH61 families) with different periodicities. The periodicity for CBP21 is shown in FIGS. 2D, 6A and 7B; periodicity for EfCBM33 is shown in FIG. 15D; periodicity for CelS2 is shown in FIGS. 17, 19, 23A, 27 and 31; and periodicity for E7 is shown in FIG. 29. One possible explanation for variation in periodicity is that crystalline cellulose has several forms and that crystals have different faces (i.e., types of surface; see, e.g., Carrard et al., 2000, *Proc Natl Acad Sci USA* 97(19):10342-7) and that different members of the CBM33 and GH61 families attack different faces. In view of the different activity of the enzymes, combinations of enzymes (which may achieve synergistic effects) may be made. Thus, for example, one could combine a GH61 with CelS2.

In the methods described above using both an oxidohydrolytic enzyme and a saccharolytic enzyme, the step with the oxidohydrolytic enzyme is carried out under conditions which allow the enzyme to interact or bind to the polysaccharide as described herein. The same conditions and considerations are applied to the additional step using additional saccharolytic enzymes (hydrolases), which step may be carried out simultaneously or subsequent to the first step. In total the incubation may be conducted for 3, 4, 5, 6, 7, 8, 9, 10, 11, 12, 13, 14 days or more, but is typically performed for preferably about 8 to about 96 hours, more preferably about 8 to about 72 hours and most preferably about 8 to about 48 hours or 4 to 24 hours.

Preferably aqueous solutions of the enzymes are used and preferably the enzymatic hydrolysis is carried out in a suitable aqueous environment under conditions that can be readily determined by one skilled in the art.

Each enzyme used in the methods may be provided as a purified preparation (as described hereinafter) or may be present in a composition, (e.g., including the other enzymes for use in the methods) preferably at at least 1, 2, 5 or 10%, preferably 1-5% w/w dry weight in the composition.

For the methods described herein, the hydrolysis can be carried out as a fed batch or continuous process where the polysaccharide-containing material (substrate), which may be pre-treated, is fed gradually to, for example, an enzyme containing hydrolysis solution.

The saccharification is generally performed in stirred-tank reactors or fermentors under controlled pH, temperature and mixing conditions as discussed herein. Suitable process time, temperature and pH conditions can readily be determined by one skilled in the art and are discussed herein and can depend on the substrate and enzymes used and their concentrations and whether the substrate has been pretreated and whether a fermenting organism is included, see hereinbelow.

The dry solids content is in the range of preferably about 5 to about 50 wt. %, more preferably about 10 to about 40 wt. % and most preferably about 15 to about 30 wt. %.

Each enzyme used in the reaction can be present in the solution at any suitable concentration, such as a concentration of 0.001-1.0 mg/ml, e.g., 0.01-0.1 mg/ml or 0.05-0.5 mg/ml. Alternatively expressed, the enzymes may be used at a concentration of 0.1-100 mg enzyme/g of polysaccharide substrate, e.g., 1-50 mg/g substrate. Suitable concentrations can be determined depending on the substrate and the material containing the substrate and the conditions of the reaction, e.g., temperature, pH and duration.

The steps in which the oxidohydrolytic enzyme and the saccharolytic enzyme(s) are contacted with the polysaccharide substrate may be performed separately or together or a combination thereof, e.g., the oxidohydrolytic enzyme may be added and after an initial incubation period the saccharolytic enzyme(s) may be added. In the alternative, the oxidohydrolytic enzyme may be removed before the saccharolytic enzyme is added. Any steps in which the oxidohydrolytic enzyme is not present (e.g., a step in which only a saccharolytic enzyme is used) need not be conducted in the presence of a reducing agent and/or metal ion.

Other enzymes may also be added in addition to or as an alternative to the chitin or cellulose hydrolytic enzymes discussed above, depending on the nature of the substrate that is to be degraded. For example, if the polysaccharide to be degraded is a copolymer which contains protein, proteases may also be added. Suitable examples include Alcalase, Neutrase, Papain and other broad-specificity proteolytic enzymes. In each experimental set-up the suitability of proteases will need to be checked, especially if other enzymes (e.g., chitinases or cellulases), which may be destroyed by some of the available proteases, are present simultaneously. If the polysaccharide is a copolymer with hemicelluloses, hemicellulolytic enzymes may be added.

Furthermore, the product resulting from using the above described oxidohydrolytic enzyme and saccharolytic enzymes may include soluble short oligosaccharides (particularly disaccharides). Since dimeric products inhibit glycoside hydrolases and since monomers are the most desirable product resulting from the degradation/hydrolysis process for further processing (see hereinbelow), additional enzymes, namely beta-glucosidases are preferably also used in the methods of the invention.

Thus in a preferred aspect, said method of degrading or hydrolyzing a polysaccharide further comprising contacting said polysaccharide (or the degradation or hydrolysis product thereof) with one or more beta-glucosidases. Such enzymes may be identified and used as specified herein (e.g., in relation to their concentration) for other saccharolytic enzymes. For cellulose a beta-glucosidase(s) may be used and for chitin a beta-N-acetylglucosaminidase(s) may be used.

The steps in which the oxidohydrolytic enzyme, saccharolytic enzyme(s) and beta-glucosidase(s) are contacted with the polysaccharide substrate may be performed separately or together or a combination thereof, e.g., the oxidohydrolytic enzyme may be added and after an initial incubation period the saccharolytic enzyme(s) and beta-glucosidase(s) may be added, or the latter two enzymes may be added sequentially. In the alternative, the oxidohydrolytic enzyme may be removed before the other enzymes are added. Any steps in which the oxidohydrolytic enzyme is not present (e.g., a step in which only a saccharolytic enzyme(s) and/or beta-glucosidase(s) is used) need not be conducted in the presence of a reducing agent and/or metal ion.

The oxidohydrolytic enzymes and saccharolytic enzymes for use in the methods of the invention may be isolated, extracted or purified from various different sources or synthesised by various different means. As mentioned above the enzymes may be provided in purified preparations or in the presence of other components.

Chemical syntheses may be performed by methods well known in the art involving, in the case of peptides, cyclic sets of reactions of selection deprotection of the functional groups of a terminal amino acid and coupling of selectively protected amino acid residues, followed finally by complete deprotection of all functional groups. Synthesis may be performed in solution or on a solid support using suitable solid phases known in the art, such as the well known Merrifield solid phase synthesis procedure.

Preferably the enzymes for use in the invention are substantially purified, e.g., pyrogen-free, e.g., more than 70%, especially preferably more than 90% pure (as assessed for example, in the case of peptides or proteins, by an appropriate technique such as peptide mapping, sequencing or chromatography or gel electrophoresis). Purification may be performed for example by chromatography (e.g., HPLC, size-exclusion, ion-exchange, affinity, hydrophobic interaction, reverse-phase) or capillary electrophoresis.

Recombinant expression of proteins is also well known in the art and an appropriate nucleic acid sequence can be used to express the enzymes used herein for subsequent expression and optional purification using techniques that are well known in the art. For example, an appropriate nucleic acid sequence can be operably linked to a promoter for expression of the enzyme to be used in bacterial cells, e.g., E. coli which may then be isolated or if the enzyme is secreted, the culture medium or the host expressing the enzyme may be used as the source of the enzyme.

The methods described above have applications in a number of different fields in which hydrolysis of polysaccharides forms one of the method steps or in which the products of that hydrolysis are useful.

Thus in a further aspect the present invention provides a method of producing soluble saccharides, wherein said method comprises degrading or hydrolyzing a polysaccharide by contacting said polysaccharide with one or more oxidohydrolytic enzymes, wherein said degradation or hydrolysis is carried out in the presence of at least one reducing agent and at least one divalent metal ion and said degradation or hydrolysis releases said soluble saccharides.

In an alternative preferred aspect the invention provides a method of producing soluble saccharides, wherein said method comprises degrading or hydrolyzing a polysaccharide by:

a) contacting said polysaccharide with one or more oxidohydrolytic enzymes, wherein said degradation or hydrolysis is carried out in the presence of at least one reducing agent and at least one divalent metal ion, b) contacting said polysaccharide (or the degradation or hydrolysis product thereof) with one or more saccharolytic enzymes selected from a cellulose hydrolase or chitin hydrolase, and optionally c) contacting said polysaccharide (or the degradation or hydrolysis product thereof) with one or more beta-glucosidases;

wherein said degradation or hydrolysis releases said soluble saccharides.

The result of complete hydrolysis is soluble sugars. Usually, a mixture of monomeric sugars and higher order oligosaccharides (e.g., disaccharides) are generated. As discussed above, preferably beta-glucosidases are used to produce monomeric sugars. The partially or completed degraded polysaccharide-containing material is preferably recovered for further processing, e.g., fermentation. Soluble products of degradation of the polysaccharide-containing material can be separated from the insoluble material using technology well known in the art such as centrifugation, filtration and gravity settling.

Preferably said soluble saccharides are isolated or recovered after said degradation or hydrolysis process. Preferably the soluble saccharides which are isolated or recovered are chitobiose and/or N-acetylglucosamine (from chitin) or cellobiose and/or glucose (from cellulose) and/or oligosaccharides thereof.

N-acetylglucosamine and oligosaccharides of N-acetylglucosamine have a number of commercial uses including use as a food supplement. Chitin fragments have found utility in various applications including use as immune stimulants (Aam et al., 2010, *Drugs* 8(5): 1482-517).

The soluble saccharides resulting from hydrolysis of cellulose have various applications, particularly for use as a source of energy in fermentation reactions.

Preferably the saccharide mixture released after hydrolysis containing monomeric sugars is fermented to generate an organic substance such as an alcohol, e.g., ethanol.

Thus the present invention further provides a method of producing an organic substance, preferably an alcohol, comprising the steps of:

i) degrading or hydrolyzing a polysaccharide by a method comprising:
   a) contacting said polysaccharide with one or more oxidohydrolytic enzymes, wherein said degradation or hydrolysis is carried out in the presence of at least one reducing agent and at least one divalent metal ion, and
   b) contacting said polysaccharide (or the degradation or hydrolysis product thereof) with one or more saccharolytic enzymes selected from a cellulase or chitinase, and optionally
   c) contacting said polysaccharide (or the degradation or hydrolysis product thereof) with one or more beta-glucosidases;
   to produce a solution comprising soluble saccharides;

ii) fermenting said soluble saccharides, preferably with one or more fermenting microorganisms to produce said organic substance as the fermentation product; and optionally iii) recovering said organic substance.

Optionally, said soluble saccharides produced in step (i) may be isolated or purified from said solution.

The organic substance thus produced forms a further aspect of the invention.

As referred to herein "soluble saccharides" include monosaccharides, disaccharides and oligonucleotides which are water soluble, preferably mono- and/or disaccharides. Preferably said soluble saccharides are fermentable, e.g., glucose, xylose, xylulose, arabinose, maltose, mannose, galactose and/or soluble oligosaccharides.

"Fermentation" refers to any fermentation process or any process comprising a fermentation step.

The above method may additionally comprise the use of one or more additional enzymes such as esterases (e.g., lipases, phospholipases and/or cutinases), proteases, laccases and peroxidases.

The steps of hydrolysis (saccharification) and fermentation may be performed separately and/or simultaneously and include, but are not limited to, separate hydrolysis and fermentation (SHF), simultaneous saccharification and fermentation (SSF), simultaneous saccharification and cofermentation (SSCF), hybrid hydrolysis and fermentation (HHF), separate hydrolysis and cofermentation (SHCF), hybrid hydrolysis and cofermentation (HHCF) and direct microbial conversion (DMC). Conveniently, any method known in the art comprising pre-treatment, enzymatic hydrolysis (saccharification), fermentation, or a combination thereof, can be used in the practicing the above methods.

Conveniently, a conventional apparatus can include a fed-batch stirred reactor, a batch stirred reactor, a continuous flow stirred reactor with ultrafiltration and/or a continuous plug-flow column reactor (de Castilhos Corazza et al., 2003, *Acta Scientiarum. Technology* 25: 33-38; Gusakov & Sinitsyn, 1985, *Enz. Microb. Technol.* 7: 346-352), an attrition reactor (Ryu & Lee, 1983, *Biotechnol. Bioeng.* 25: 53-65), or a reactor with intensive stirring induced by an electromagnetic field (Gusakov et al., 1996, *Appl. Biochem. Biotechnol.* 56: 141-153). Additional reactor types include, for example, fluidized bed, upflow blanket, immobilized and extruder type reactors for hydrolysis and/or fermentation.

Pre-treatments that may be used were discussed herein and apply to all methods of the invention. The polysaccharide-containing material can be pre-treated before hydrolysis and/or fermentation. Pre-treatment is preferably performed prior to the hydrolysis step. Alternatively, the pretreatment can be carried out simultaneously with hydrolysis, such as simultaneously with treatment of the polysaccharide-containing material with the enzymes used in the methods (i.e., oxidohydrolytic and saccharolytic enzymes) to release fermentable sugars, such as glucose and/or cellobiose. In most cases the pre-treatment step itself results in some conversion of biomass to fermentable sugars (even in the absence of enzymes).

The fermentable sugars obtained by the method of the invention can be fermented by one or more fermenting microorganisms capable of fermenting the sugars directly or indirectly into a desired fermentation product.

The fermentation conditions depend on the desired fermentation product and fermenting organism and can easily be determined by one skilled in the art.

In the fermentation step, sugars, released from the substrate are fermented to a product, e.g., ethanol, by a fermenting organism, such as yeast. The polysaccharide substrate to be used in the method may be selected based on the desired fermentation product.

The "fermenting microorganism" refers to any microorganism, including bacterial and fungal organisms, suitable for use in the fermentation process to produce a fermentation product.

The fermenting organism can be C6 and/or C5 fermenting organisms, or a combination thereof. Both C6 and C5 fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment C6 sugars include bacterial and fungal organisms, such as yeast. Preferred yeast includes strains of *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis* or *Candida utilis*.

Other fermenting organisms include strains of *Zymomonas*, such as *Zymomonas mobilis*; *Hansenula*, such as *Hansenula anomala*; *Klyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*, *Saccharomyces distaticus*, *Saccharomyces uvarum*. In another preferred aspect, the yeast is a *Kluyveromyces*, e.g., *Kluyveromyces marxianus* or *Kluyveromyces fragilis*.

Other yeast that may be used include *Clavispora*, e.g., *Clavispora lusitaniae* or *Clavispora opuntiae*; *Pachysolen*, e.g., *Pachysolen tannophilus*; and *Bretannomyces*, e.g., *Bretannomyces clausenii*.

Bacteria that can efficiently ferment hexose and pentose to ethanol include, for example, *Zymomonas*, such as *Zymomonas mobilis* and *Clostridium*, such as *Clostridium thermocellum*.

Commercially available yeast suitable for ethanol production include, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden) and FERMIOL™ (available from DSM Specialties).

The fermenting microorganism(s) is typically added to the degraded polysaccharide-material and the fermentation is performed for about 8 to about 96 hours, such as about 24 to about 60 hours. The temperature is typically between about 26° C. to about 60° C., in particular about 32° C. to 50° C. and at about pH 3 to about pH 8, such as around pH 4-5, 6, or 7. The above conditions will of course depend on various factors including the fermenting microorganism that is used.

The fermenting microorganism(s) is preferably applied in amounts of approximately $10^5$ to $10^{12}$, preferably from approximately $10^7$ to $10^{10}$, especially approximately $2 \times 10^8$ viable cell count per ml of fermentation broth.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin and Vitamins A, B, C, D and E.

The organic substance which is the fermentation product can be any substance derived from the fermentation. The fermentation product can be, without limitation, an alcohol (e.g., arabinitol, butanol, ethanol, glycerol, methanol, 1,3-propanediol, sorbitol or xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid or xylonic acid); a ketone (e.g., acetone); an aldehyde (e.g., formaldehyde); an amino acid (e.g., aspartic acid, glutamic acid, glycine, lysine, serine or threonine); or a gas (e.g., methane, hydrogen ($H_2$), carbon dioxide ($CO_2$) or carbon monoxide (CO)). The fermentation product may also be an alkane, a cycloalkane, an alkene, isoprene, or polyketide. The fermentation product can also be protein.

In a preferred aspect, the fermentation product is an alcohol. It will be understood that the term "alcohol" encompasses a substance that contains one or more hydroxyl moieties. Preferably the alcohol is arabinitol, butanol, ethanol, glycerol, methanol, 1,3-propanediol, sorbitol or xylitol. Ethanol is the preferred product.

The fermentation product(s) may be recovered from the fermentation medium using any method known in the art including, but not limited to, chromatography (e.g., ion exchange, affinity, hydrophobic, chromatofocusing and size exclusion), electrophoretic procedures (e.g., preparative isoelectric focusing), differential solubility (e.g., ammonium sulfate precipitation), distillation or extraction. For example, ethanol is separated from the fermented cellulose-containing material and purified by conventional methods of distillation. Ethanol with a purity of up to about 96 vol. % can be obtained.

The present invention is further described by the following examples that should not be construed as limiting the scope of the invention.

EXAMPLES

Example 1: Effects of Oxidohydrolytic Enzymes CBP21, EfCBM33, CelS2 and E7 on Chitin or Cellulose Substrates Materials and Methods
Reagents Pure beta-chitin powder (80# mesh) from squid pen was purchased from France Chitin (Marseille, France). $H_2^{18}O$ (containing 97% $^{18}O$) and $^{18}O_2$ (containing 99% $^{18}O$) was purchased from Cambridge Isotope Laboratories Inc. (Andover, Mass.). 2,5-dihydroxy-benzoic acid (DHB) was purchased from Bruker Daltonics (Bremen, Germany). Dithionite, ascorbic acid, reduced glutathione, Fe(II)SO$_4$, Cu(I) acetate, MgCl$_2$, ZnCl$_2$, CoCl$_2$, LiCl, acetonitrile, Trisma-Base, HCl, EDTA and H$_2$O$_2$(30% v/v) were all purchased from Sigma-Aldrich Inc. The Schlenk line was hand-made at the University of Oslo and used with an in-house N$_2$ supply (99.999% pure). The N$_2$ gas was purchased from YARA PRAXAIR (Oslo, Norway). Oligosaccharides of N-Acetyl-D-glucosamine ranging from dimer to hexamer were purchased from Seikagaku (Tokyo, Japan). Chitin beads for protein purification were purchased from New England Biolabs.

Nano-whiskers of beta-chitin were prepared according as described in (Fan et al., 2008, *Biomacromolecules* 9: 1919) by sonication of 3.0 mg/mL beta-chitin particles suspended in 0.2 M acetic acid using a Vibracell Ultrasonic Processor equipped with a 3 mm sonication probe (Sonics, Newtown, Conn.) in four, one minute intervals with 30 s pauses between each interval. Before use, the buffer in the chitin-whisker suspension was changed to 20 mM Tris pH 8.0 by dialysis. These whiskers were used for the experiment displayed in FIG. 2A, where an increased surface area was needed to enable detection of CBP21 activity in the absence of reductants and additional enzymes. All other experiments were performed with non-treated beta-chitin.

Cloning, Expression and Purification of Recombinant Proteins

Chitin Binding Protein 21 (CBP21) from Serratia marcescens

CBP21 was cloned, produced and purified as previously described (Vaaje-Kolstad et al., 2005, J. Biol. Chem. 280: 11313). Briefly, the E. coli BL21 DE3 strain harbouring the pRSET-B vector containing the cbp21 gene was grown overnight and harvested. The periplasmic content of the cells containing CBP21 was extracted by cold osmotic shock, filtered through a 0.2 micron syringe filter and kept at 4° C. Further, CBP21 was purified from the periplasmic extract by chitin affinity chromatography, using chitin beads (NEB) as chromatographic medium. CBP21 was bound to the column using 20 mM Tris pH 8.0 and 1.0 M $(NH_4)_2SO_4$ as binding buffer. After non-bound protein had passed through the column, the binding buffer was run for one column volume before eluting CBP21 with 20 mM acetic acid. The fraction containing CBP21 was concentrated using an Amicon Ultra centrifugal filter unit with 10 kDa molecular weight cut off, dialysed into 20 mM Tris-HCl pH 8.0 and stored at 4° C. until use. Protein purity was assessed by SDS-PAGE (always >99% pure) and protein concentration was determined by the Bio-Rad protein assay (Bio-Rad Laboratories, Inc., USA) according to the instructions supplied by the manufacturer. Single site mutants of CBP21 were made as previously described (Vaaje-Kolstad et al., 2005, J. Biol. Chem. 280: 11313) using the QuickChange site-directed mutagenesis kit (Stratagene).

Chitinase C (ChiC) from Serratia marcescens

ChiC was cloned and produced as previously described (Synstad et al., 2008, Biosci. Biotechnol. Biochem. 72: 715). Briefly, E. coli BL21 DE3 cells harbouring a pREST-B vector containing the chic gene under control of the T7 promoter were grown to OD 0.6 and induced by 0.4 mM IPTG. The enzyme was extracted from the cells by periplasmic extraction by cold osmotic shock. Further, ChiC was purified from the periplasmic extract by chitin affinity chromatography using chitin beads (NEB) as column material. Using 20 M Tris-HCl, pH 8.0 as running buffer, the periplasmic extract containing ChiC was passed through the column at 2.5 ml/min enabling binding of the chitinase to the chitin beads. After the non-bound proteins in the extract had passed through the column, one column volume of running buffer was run through the column before eluting the bound chitinase with 20 mM acetic acid. Following elution, the purified protein was concentrated using an Amicon ultrafiltration device (Millipore) and finally dialysed into 20 mM Tris-HCl, pH 8.0 and stored at 4° C. before use. Protein purity was routinely assayed by SDS-PAGE and protein concentration was determined by the Bio-Rad method.

Chitin Deacetylase (AnCDA) from Aspergillus nidulans

Aspergillus nidulans FGSC A4 (obtained from FGSC) was grown at 37° C. in solid YAG medium (5 g/L yeast extract, 20 g/L glucose, 20 g/L agar, 1 ml/L Cove's Trace Elements, 1.2 g/L $MgSO_4 7H_2O$) for 24-48 h to provide an inoculum, and in liquid YG medium, typically for 16-24 hours with vigorous shaking (250-300 rpm). Genomic DNA was isolated with the SP Fungi DNA Mini Kit (Omega Bio-tek, USA). The gene (GeneBank accession number EAA66447.1) was amplified from Aspergillus nidulans FGSC A4 genomic DNA using overlap extension polymerase chain reactions, excluding introns as well as the gene part coding for the signal peptide. Primers for the reactions were P1f (BglII): cga agatct acg cct ctg cct ttg gtt c (SEQ ID NO: 17), P2r: gag acg tgg tcg tat gta tgt gcg ccg act tga tg (SEQ ID NO: 18); P3f: caa gtc ggc gca cat aca tac gac cac gtc tcc ctc c (SEQ ID NO: 19); P4r: cca aca gtc gta gct atc aac cct cga gca tta ac (SEQ ID NO: 20); and P5r (HindIII): cag aagctt tca atg ata cca cgc aat ctc tcc atc acc gag aca atc acc aac agt cgt agc tat caa c (SEQ ID NO: 21). A BglII and a HindIII site were incorporated at the start and the end of the AnCDA gene to produce an in-frame N-terminal His tag-fused construct in the pBAD/HisB(s) vector. This vector is a variant of the commercial vector pBAD/HisB (Invitrogen, USA) where the region between the N-terminal polyhistidine tail and the multiple cloning site has been shortened (Kallio et al., 2006, J. Mol. Biol. 357: 210). The resulting plasmids were transformed into Escherichia coli TOP10 cells (Invitrogen) and the inserted gene was sequenced at the sequencing facility of the Department of Chemistry, Biotechnology and Food Science at the Norwegian University of Life Sciences.

For protein expression, the transformed E. coli strain was grown at 37° C. in 2×TY medium (16 g/L Tryptone, 10 g/L yeast extract, 5 g/L NaCl) containing 100 mg of ampicillin per liter until $OD_{600}$=0.6 and subsequently induced with 0.02% (w/v; final concentration) arabinose before further incubation at 28° C. overnight. Cells were harvested by centrifugation and the protein was purified to homogeneity by $Ni^{2+}$ affinity chromatography. Protein concentrations were determined using the Bio-Rad protein assay, with bovine serum albumin as a standard.

E7 from Thermobifida fusca xy (Q47QG3)

The gene sequence encoding the mature variant of Q47QG3 from T. fusca xy (E7; residues 37-222) was cloned by amplifying the corresponding gene region from genomic DNA from T. fusca xy (purchased from ATCC) using primers designed according to the In-Fusion cloning protocol (Clontech). The resulting PCR product was inserted into a modified pRSETB vector (Invitrogen) using the In-Fusion™ technology (Clonetech) in-frame with the signal peptide for direction of the protein product to the periplasm upon expression in E. coli. The modified pRSETB vector has the His-tag containing region replaced by the signal sequence encoding region of the cbp gene from from Serratia marcescens (Vaaje-Kolstad et al., 2005, J. Biol. Chem. 280: 11313). By inserting genes of interest in frame with the signal sequence, the gene product will be transported to the periplasm upon expression in E. coli and the exported protein will have a native N-terminus, meaning that the protein sequence starts with a histidine. Successful constructs were sequenced for verification and transformed into E. coli BL21 DE(3) for protein expression. Cultures were grown overnight at 37° C. Cells were harvested by centrifugation and subjected to periplasmic extraction by cold osmotic shock. The mature E7 protein was purified by chitin affinity chromatography using the chitin-beads to capture the protein. The capture buffer contained 20 mM Tris-HCl pH 8.0 and 1.0 M ammonium sulphate. The protein was eluted from the column using 20 mM acetic acid. Peaks containing pure protein were pooled and concentrated using Sartorius Vivaspin devices with a 10 kDa cutoff. Using the same protein concentration device, the buffer was changed to 20 mM Tris pH 8.0.

CelS2 from *Streptomyces coelicolor* A3(2) (Q9RJY2)

A gene encoding the mature form of Q9RJY2 from *S. coelicolor* A3(2) (CelS2; residues 35-364) was cloned by amplifying the corresponding gene region from genomic DNA from *S. coelicolor* A3(2) (purchased from ATCC) using primers designed according to the LIC cloning protocol (Novagen) that places a hexa-histidine tag art the N-terminus of the protein that can be removed using the Factor Xa protease, leaving no non-native amino acids on the N-terminus of the protein. The PCR product was inserted into the pET-32 LIC vector according to the instructions supplied by the manufacturer (Novagen). Successful constructs were sequenced for verification and transformed into *E. coli* Rosetta DE(3) for protein expression. Expression of soluble target protein was obtained by growing a 5 ml pre-culture of the transformed Rosetta DE(3) cells overnight at 37° C., which was used the next day to innoculate a 300 ml volume of LB-medium and growth was continued with shaking at 250 rpm at 37° C. Gene expression was induced by adding IPTG to a final concentration of 0.1 mM when cell density reached an O.D. of 0.6, followed by immediate transfer of the culture to a shaking incubator having 20° C. and for continuing the culturing overnight. The following day cells were harvested by centrifugation. Cell pellets were resuspended in sonication buffer (20 mM Tris-HCl pH 8.0, 100 M PMSF, lysozyme and DNAse) followed by sonication using a Vibra Cell Ultrasonic processor equipped with a 3 mm sonication probe (Sonics) in order to release cytoplasmic proteins. Cell debris was removed by centrifugation and His-tagged Q9RJY2 was purified by standard IMAC (immobilized metal affinity chromatography) purification protocols using the Nickel-NTA IMAC resin (Qiagen). Purified protein was concentrated using Sartorius Vivaspin protein concentration devices with a 10 kDa cutoff, which also were used concomitantly to change to buffer into a buffer suitable for Factor Xa removal of the His-tag (100 mM NaCl, 5.0 mM $CaCl_2$, 50 mM Tris pH 8.0). His-tags were cleaved off by adding Factor Xa and incubating overnight at room temperature, followed by His-tag removal using standard IMAC chromatography. The flow through protein fraction containing the processed Q9RJY2 protein and Factor Xa was collected and concentrated using Sartorius Vivaspin® protein concentration devices with a 10 kDa cutoff. Finally, Factor Xa was removed using Xarrest agarose beads according to the manufacturer's instructions (Novagen). The buffer of the pure protein was changed to 20 mM Tris pH 8.0 using Sartorius Vivaspin® protein concentration devices with a 10 kDa cutoff. Correct processing of the His-tag was verified by SDS-PAGE analysis.

Protein concentration was quantified using the Bio-Rad Bradford micro assay (Bio-Rad) and protein purity was validated by SDS-PAGE.

Site-directed mutagenesis of the gene encoding the CelS2 protein was done using the Quickchange® Mutagenesis Kit (Stratagene) and according to instructions provided by the manufacturer. The mutated protein was expressed and purified using methods identical to those used for the wild-type protein.

Purification of Cel7A from *Trichoderma reesei/Hypocrea jecorina* The endo-acting family GH7 cellulase Cel7A from *Hypocrea jecorina* was purified from the commercially available *H. jecorina* extract CELLUCLAST™ (Novozymes) using purification protocols described by Jager et al., 2010, *Biotechnology for Biofuels* 3(18). In short, the *H. jecorina* extract was adjusted to 10 mM AmAc pH 5.0 and the enzyme was purified using a DEAE-sepharose column attached to an Äcta Purifier running 10 mM AmAc pH 5.0 as a mobile phase. Relevant fractions were pooled and concentrated using Sartorius Vivaspin protein concentration devices with a 10 kDa cutoff. Purity was assessed using SDS-PAGE analysis.

Product Analysis by Mass Spectrometry (MS)

Matrix-Assisted Laser Desorption/Ionization—Time of Flight (MALDI-TOF)

Two microliter of a 9 mg/mL mixture of 2,5-dihydroxybenzoic acid (DHB) in 30% acetonitrile was applied to a MTP 384 target plate ground steel TF (Bruker Daltonics). One microliter sample was then mixed into the DHB droplet and dried under a stream of air. The samples were analyzed with an Ultraflex MALDI-TOF/TOF instrument (Bruker Daltonics GmbH, Bremen, Germany) with a Nitrogen 337 nm laser beam. The instrument was operated in positive acquisition mode and controlled by the FlexControl 3.3 software package. All spectra were obtained using the reflectron mode with an acceleration voltage of 25 kV, a reflector voltage of 26, and pulsed ion extraction of 40 ns in the positive ion mode. The acquisition range used was from m/z 0 to 7000. The data were collected from averaging 400 laser shots, with the lowest laser energy necessary to obtain sufficient signal to noise ratios. Peak lists were generated from the MS spectra using Bruker FlexAnalysis software (Version 3.3). Post-source decay (PSD) spectra using the Bruker Daltonics LIFT system were recorded at 8 kV precursor ion acceleration voltage and fragment acceleration (LIFT voltage 19 kV). The reflector voltage 1 and 2 were set to 29 and 14.5 kV, respectively.

Product Analysis by HPLC and UHPLC

High Performance Liquid Chromatography (HPLC)

Isocratic HPLC was run on a Dionex Ultimate 3000 HPLC system set up with a 4.6×250 mm Amide-80 column (Tosoh Bioscience, Montgomeryville, Pa., USA) with an Amide-80 guard column. The mobile phase consisted of 70% acetonitrile:30% MilliQ $H_2O$ and the flow rate was 0.7 ml/min. Eluted oligosaccharides were monitored by recording absorption at 190 nm. Chromatograms were recorded, integrated and analysed using the Chromeleon 6.8 chromatography software (Dionex). The major product of chitin degradation by ChiC is $(GlcNAc)_2$ (>95% of the total amount of degradation products on a molar basis), thus only $(GlcNAc)_2$ peaks were subject for data analysis and used for quantification of the extent of chitin degradation. A standard solution containing 0.10 mM $(GlcNAc)_2$ was analyzed at regular intervals during the sample series, and the resulting average values (displaying standard deviations of less than 3%) were used for calibration.

For the sake of experimental simplicity and throughput, the degradation of chitin in reactions with ChiC and CBP21 was quantitatively assessed by measuring concentration of the dominant product, $(GlcNAc)_2$, only. As a result of this simplification, product levels for maximally degraded chitin tend to be up to 25% lower than expected on the basis of the starting concentration of chitin. This "loss" is due to the lack of detection of the following products: (1) longer oligomers and monomers which may amount to an estimated 5 wt. % of the total product mixture, (2) partially deacetylated products; the chitin that we use contains a small fraction of deacetylated sugars (about 8%), (3) oxidized sugars. We have used conditions that boost CBP21 activity to a maximum. The amounts of undetected oxidized sugars may amount to as much as 10-15% of the starting material (FIG. 16).

Ultra High Performance Liquid Chromatography (UHPLC)

UHPLC was run on an Agilent 1290 Infinity UHPLC system equipped with diode array detector, set up with a Waters Acquity UPLC BEH amide column (2.1×150 mm with a 2.1×30 mm pre column both having a column material particle size of 1.7 μm) using 5 μL sample injections. Separation of oxidized oligosaccharides was obtained at column temperature 30° C. and a flow of 0.4 mL/min starting at 72% ACN (A):28% 15 mM Tris-HCl pH 8.0 (B) for 4 minutes, followed by an 11 minute gradient to 62% A: 38% B which was held for three minutes. Column reconditioning was obtained by a two minute gradient to initial conditions and subsequent running at initial conditions for 5 minutes. Eluted oligosaccharides were monitored by recording absorption at 205 nm. Chromatograms were recorded, integrated and analysed using the ChemStation rev. B.04.02 chromatography software (Agilent Technologies). The identity of the eluted oligosaccharides was verified by MALDI-TOF MS analysis according to the protocol described above.

Degradation Reactions and Sampling

General Reaction Conditions

Typical reactions were initiated by mixing beta-chitin (0.5 to 2 mg/mL) with CBP21 (0.1 to 1 μM), ChiC (0.5 μM) or AnCDA (1 μM) or combinations of these enzymes at a total volume of 0.5 ml in 1.5 ml plastic reaction tubes (Axygen Scientific Inc, CA) or in 1.8 ml borosilicate glass vials with screw cap tops and TEFLON® lined rubber septa. All reactions were carried out in 20 mM Tris-HCl, pH 8.0 and incubated at 37° C. with shaking at 1000 rpm in an Eppendorf Thermo mixer unless stated otherwise. All reactions used for quantification were run in triplicates. All reactions used for qualitative purposes were repeated at least three times.

Reactions with CBP21

Chitin solubilization by CBP21 was investigated by adding 1.0 μM CBP21 to a reaction solution containing 2.0 mg/mL beta-chitin and 5.0, 1.0 or 0.2 mM ascorbic acid in 20 mM Tris-HCl pH 8.0. Reactions were incubated at 37° C. and samples were taken at regular time intervals for analysis by MALDI-TOF MS and UHPLC. In order to investigate the effects of reducing agents on the function of CBP21, ascorbic acid was exchanged with either 1 mM reduced glutathione or 1 mM Fe(II)SO$_4$ in some reactions.

The effect of CBP21 on chitinase activity was studied by adding 0.5 μM ChiC and 1.0 μM CBP21 to a reaction solution containing 2.0 mg/mL beta-chitin and 1.0 mM ascorbic acid in 20 mM Tris-HCl pH 8.0. The reaction was incubated at 37° C. and sampled at regular time intervals. Chitin degradation was measured by determining the concentration of (GlcNAc)$_2$ by HPLC. Control experiments where CBP21 and/or ascorbic acid were excluded from the reaction solution were performed in the same manner.

To investigate whether CBP21 was capable of cleaving and/or oxidizing soluble substrates, a 500 μL reaction solution containing 1.0 μM CBP21, 100 μM (GlcNAc)$_6$ (0.12 mg/mL) and 1.0 mM ascorbic acid all dissolved in 20 mM Tris pH 8.0 was incubated for 16 hours at 37° C. before product analysis by MALDI-TOF MS. The same was performed for control reactions where either CBP21 or ascorbic acid or both were excluded from the reaction solution.

An experiment designed to visualize the range of polymeric products generated by CBP21 was performed by combining 1.0 μM CBP21 and 1.0 μM AnCDA in a reaction solution containing 2.0 mg/mL beta-chitin, 1.0 mM ascorbic acid and 10 μl CoCl$_2$ (necessary for full AnCDA activity) in 20 mM Tris-HCl pH 8.0. Control reactions were performed where CBP21 was excluded from the reaction solution and/or replaced by 0.5 μM ChiC. The reactions were incubated for 16 hours at 37° C., followed by product analysis with MALDI-TOF MS.

Molecular Oxygen Free Reaction and Related Control Reactions

In order to obtain a di-oxygen free reaction solution, all reaction components except the enzyme or enzymes were mixed in a glass vial closed with a screw cap containing a rubber septum and degassed using a Schlenk line. The enzyme was added to a separate vial which was treated identically to the vial containing the reaction mixture. Before starting the degassing procedure, a freshly made 1.0 M dithionite solution was added the reaction solution to yield a final concentration of 10 mM to ensure total removal of molecular oxygen in the solution. The degassing procedure was performed by penetrating the rubber septum of the sealed vial with a needle connected to the Schlenk line, followed by five cycles of 5 minute degassing (vacuum) and 1 minute of N$_2$ saturation. The final cycle left the vials slightly pressurized by N$_2$. After degassing both the reaction solution and the enzyme solution, a syringe was used to withdraw an appropriate amount of the enzyme solution which then was promptly injected into the vial containing the reaction solution in order to initiate the reaction, while injecting bubbles of air was avoided. The effect of a molecular oxygen free environment was assessed by analyzing the activity of 1.0 μM CBP21 on 2.0 mg/mL beta-chitin in the presence of 1.0 mM ascorbic acid in 20 mM Tris-HCl pH 8.0 by MALDI-TOF MS. Additionally, the degradation of 0.1 mg/ml beta-chitin by 0.5 μM ChiC in the presence of 1.0 μM CBP21 and 1.0 mM ascorbic acid in 20 mM Tris-HCl pH 8.0 was analyzed in the same di-oxygen free environment. Samples were analysed by HPLC after 16 hours incubation at 37° C.

This latter experiment was also conducted in the absence of sodium dithionite and at a higher chitin concentration (0.45 mg/mL), but with otherwise identical reaction conditions. It should be noted that even though every precaution was taken to avoid oxygen entering the reaction solution, the dioxygen removal is not 100% efficient. This can be seen by studying the result from the $^{18}O_2$ experiment (see FIG. 7C), where products resulting from oxidation by $^{16}O_2$ are detected.

Additional control experiments were performed by running experiments where 0.45 mg/mL beta-chitin, 1.0 μM CBP21, 0.5 μM ChiC and 1.0 mM reduced glutathione in 20 mM Tris-HCl pH 8.0, were run in the presence of either 2.0 mM sodium azide or 2.0 mM potassium cyanide. The reactions were incubated at 37° C., sampled at 30, 60 and 90 minutes, and products were analyzed by UHPLC.

Reactions Under Metal Chelating Conditions

Divalent cations were removed by chelation through dialysis of a 10 mg/mL CBP21 solution in a buffer containing 20 mM Tris-HCl and 5 mM EDTA. The protein solution was present in a Slide-A-Lyzer cassette (Pierce) with 10 kDa MW cut-off dialysis membrane. Dialysis was performed for 16 hours at 4° C. with a protein to buffer volume ratio of 1:1000 with moderate magnetic stirring. Reactions with metal-free CBP21 were performed as described above, except that EDTA was added to the reaction buffer to a final concentration of 5 mM. Re-activation of metal-free CBP21 was achieved by adding either ZnCl$_2$ or MgCl$_2$ to the reaction mixture to a final concentration of 25 mM. Reactions were run for 180 minutes and sampled at 30 minute intervals. For the re-activation experiment, the divalent cations were added to the appropriate reaction solutions immediately after the third sampling (90 minutes). Chitin degradation was measured by determining the concentration of (GlcNAc)$_2$ by HPLC.

Reactions in Buffered $H_2^{18}O$

Beta-chitin and ascorbic acid were each suspended/dissolved in $H_2^{18}O$ to yield concentrations of 2 mg/mL and 1.0 M, respectively. In order to achieve the correct pH in the $H_2^{18}O$ reaction solution 10 µL 1.0 M Tris-HCl pH 8.0 was transferred to a glass vial, which was heated with dry air at 60° C. until all liquid had evaporated. 498 µL of the beta-chitin suspension was transferred to the same glass vial achieving the intended pH for the reaction. Concomitantly 0.5 µL ascorbic acid (dissolved in $H_2^{18}O$) and 0.75 µL of a 660 µM solution of CBP21 (dissolved in $H_2^{16}O$) were added to the solution to start the reaction, yielding final concentrations of 1 mM for ascorbic acid and 1 µM for CBP21. The glass vial was sealed with a screw cap with a TEFLON® coated rubber liner to ensure as little as possible contamination of $H_2^{16}O$ from the air phase into the reaction solution. After incubation for 16 hours at 37° C. reaction products were analyzed by MALDI-TOF MS.

Reactions in an $^{18}O_2$ Gas Saturation Solution

In a glass vial containing a reaction mixture of 2.0 mg/mL beta-chitin and 1.0 mM ascorbic acid in 20 mM Tris pH 8.0, CBP21 was added to yield a final concentration of 1.0 µM. Immediately after reaction initiation a screw cap containing a TEFLON® lined rubber septum was used to close the vial and the Schlenk line was used to remove dissolved molecular oxygen and fill the head space with $N_2$ (according to the procedure described under the heading "molecular oxygen free reaction"). After the five cycles of degassing and $N_2$ filling were completed, a gas cylinder containing compressed $^{18}O_2$ gas was connected to the vial by pushing a needle through the septum of the vial. The vial was then placed under vacuum, removing atmospheric gas residing in the tubing and the head space of the vial. After isolating the vial and the $^{18}O_2$ gas cylinder from the rest of the Schlenk line by closing appropriate in-line valves, the head space of the vial was filled with $^{18}O_2$ gas by slowly opening the gas cylinder regulator. The vial was then removed from the needle connections and after incubation at 37° C. for 16 hours reaction products were analyzed by MALDI-TOF MS.

Reaction of Beta-Chitin with Fenton Chemistry

In order to determine whether Fenton chemistry ($Fe^{2+}$ and $H_2O_2$ combined in an oxygen saturated solution to yield reactive hydroxyl radicals; Sawyer et al., 1996, *Acc. Chem. Res.* 29: 409) would yield soluble products from chitin, 2 mg/mL beta-chitin suspended in 20 mM Tris-HCl pH 8.0 was incubated for 16 hours with 10 mM Fe(II)SO$_4$ and 0.3, 0.03 or 0.003% (v/v) $H_2O_2$ in plastic sample tubes having perforated lids (for release of gas generated during the reaction). Samples were analyzed by MALDI-TOF MS.

Control Experiment with Another CBM33 Protein Identified by Genome Mining—CBM33 (EF0362) from *Enterococcus feacalis*

The gene encoding the mature family 33 CBM from *Enterococcus faecalis*, EfCBM33 (Uniprot ID: Q838S1; EF0362; uniprot.org/uniprot/Q838S1), without its native leader peptide, was cloned into the pRSET-B-CBP21 vector in frame with the CBP21 leader peptide, replacing the gene encoding CBP21. The protein was expressed in *E. coli* BL21 DE3 cells, harvested from the periplasmic fraction by cold osmotic shock and purified to homogeneity by chitin affinity chromatography. Thus, this protein was expressed and purified in exactly the same way as CBP21, using CBP21's leader peptide to drive secretion. The fractions containing pure protein (assessed by SDS-PAGE) were pooled and concentrated using an Amicon centrifugal concentrator with 10 kDa cutoff to yield a 20 mg/ml solution. The protein was crystallized by hanging drop vapor diffusion experiments using a crystallization liquor containing 1.0 MK/Na Tartrate, 0.1 M imidazol pH 8.0 and 0.2 M NaCl. Crystals pyramidal in shape and measuring approximately 0.2 mm in width (see FIG. 15A) were obtained after 48 hours incubation at room temperature. A 0.95 Å dataset has been collected from a single crystal and the structure has been solved by molecular replacement using CBP21 (PDB ID 2BEM) as template. Refinement is complete, but not published. The quality of the data is illustrated by FIG. 15B. FIG. 15C shows a structural superposition of CBP21 and EfCBM33.

For use in chitin degradation experiments, eight crystals were harvested from a 2 µL drop using a nylon loop and transferred to a 4 µL drop containing the crystallization liquor from the buffer reservoir. The crystals were mixed around in order to "rinse off" potential contaminants. After the first rinse, the crystals were transferred to a new 4 µL drop containing the crystallization liquor for a second rinsing cycle. Finally, all crystals were transferred to and dissolved in a 4 µL drop containing 20 mM Tris-HCl, pH 8.0. The resulting solution was diluted by adding it to a test tube containing 46 µL 20 mM Tris-HCl, pH 8.0. For reactions with beta-chitin, 5 µL of the EfCBM33 solution was mixed with a 95 µL solution containing 2 mg/ml beta-chitin and 2 mM ascorbic acid in 20 mM Tris-HCl pH 8.0; the reaction mixture was then incubated for 90 minutes at 37° C. in a test tube incubator rotating at 1400 rpm. Soluble products in the supernatant of the reaction were analyzed by MALDI-TOF, using the same methods as those used for testing the activity of CBP21. Further, the ability of EfCBM33 to boost degradation of alpha-chitin was probed by conducting an experiment where 2.0 mg/ml alpha-chitin (shrimp shells) was incubated with 0.3 µM of the chitinase from *Enterococcus feacalis* (protein name (EF0361)) in the presence or absence of 0.3 µM EfCBM33 and 1.0 mM reductant (R: reduced glutathione) incubated at 37° C. with agitation at 900 rpm. A boost of the chitinase activity is clearly observed in the presence of EfCBM33 and reductant.

Determination of CBP21 Reaction Speed and Degree of Substrate Oxidation

Using the UHPLC method for separating oxidized chitooligosaccharides, pure GlcNAc3GlcNAcA and GlcNAc4GlcNAcA samples were obtained by fractionation of beta-chitin samples treated by CBP21 in the presence of ascorbic acid. Fractions were dried under vacuum (Speedy-Vac), and resuspended in 50 µL MilliQ water. Purity was verified by MALDI-TOF MS. Isolated GlcNAc3GlcNAcA or GlcNAc4GlcNAcA were each incubated for 2 hours at 37° C. with 7.0 µM of a pure recombinant family 19 chitinase (ChiG from *Streptomyces coelicolor* (Hoell et al., 2006, *FEBS J.* 273: 4889)) resulting in production of equimolar amounts of GlcNAc2 and GlcNAcGlcNAcA or GlcNAc2GlcNAcA, respectively. The amount of GlcNAc2 resulting from the hydrolysis was estimated using a predetermined standard curve. Response factors for the GlcNAcA containing oligosaccharides were obtained by determining GlcNAcGlcNAcA/GlcNAc2 and GlcNAc2GlcNAcA/GlcNAc2 peak area ratios and found to be 0.71 and 0.81, respectively. A response factor for GlcNAc3GlcNAcA was approximated to be 0.88 by extrapolation of the two experimentally determined response factors. Using the response factors determined, GlcNAcGlcNAcA and GlcNAc2GlcNAcA peaks could be quantified using GlcNAc2 for calibration. In experiments for the simultaneous detection and quantification of GlcNAc2 and oxidized oligomers 1.0 mM of reduced gluthathione was used as reductant instead of ascorbic acid because the latter interferes with the chromatographic analysis. Additionally, the reactions contained 0.45 mg/mL beta-chitin, 1.0 µM CBP21 and 0.5 ChiC µM in 20 mM Tris-HCl pH 8.0.

The reactions were incubated at 37° C. in an Eppendorf Thermo mixer with shaking at 1000 rpm, and sampled at 30, 60, 120 and 300 minutes. All samples were mixed 1:1 with 100% acetonitrile in order to stop the reaction and soluble products were analyzed by UHPLC. Separation of the oxidized oligosaccharides and GlcNAc2 was achieved using a column temperature of 30° C. and a flow of 0.4 mL/min, with a gradient starting at 80% ACN (A):20% 15 mM Tris-HCl pH 8.0 (B) for 4.5 minutes, followed by an 11 minute gradient to 63% A: 37% B which was held for 3.5 minutes. Column reconditioning was achieved by a two minute gradient to initial conditions and subsequent running at initial conditions for 5 minutes. Eluted oligosaccharides were monitored by recording absorption at 205 nm. Chromatograms were recorded, integrated and analysed using the ChemStation rev. B.04.02 chromatography software (Agilent Technologies).

In order to approximate the rate of the CBP21 oxidohydrolytic activity, reactions containing 0.45 mg/mL beta-chitin, 1.0 µM CBP21 and 1.0 mM reduced glutathione in 20 mM Tris-HCl pH 8.0 were incubated at 37° C. and sampled at 10, 15, 30, 45, 60 and 300 minutes. Instead of stopping the reaction with acetonitrile, a cocktail of purified recombinant chitinases containing 28 µM ChiC (see above), 71 µM ChiG (Hoell et al., 2006, supra), 63 µM ChiB (Brurberg et al., 1995, *Microbiology* 141: 123, Brurberg et al., 1996, *Microbiology* 142: 1581) and 15 µM ChiA (Brurberg et al., 1996, supra, Brurberg et al., 1994, *FEMS Microbiol. Lett.* 124: 399) was added to the sample (0.1 volume) in order to obtain rapid complete degradation of the chitin. Under these conditions, insoluble chitin completely disappeared within 30 minutes. The quantities of the oxidized products (exclusively GlcnAcGlcNAcA and GlcNAc2GlcNAcA) were determined using the UHPLC method outlined above.

Analysis and Quantization of Glucose and Cellobiose by HPLC (E7 and CelS2)

Samples containing glucose and cellobiose were analysed by isocratic HPLC run on a Dionex Ultimate 3000 HPLC system set up with a 7.8×100 mm Rezex RFQ-Fast Fruit H+ column (Phenomonex) heated to 80° C. The mobile phase consisted of 5 mM sulfuric acid and the flow rate used was 1.0 ml/min. Eluted glucose and cellobiose were monitored by recording refractive index. Quantification was obtained by running glucose and cellobiose standards. Chromatograms were recorded, integrated and analysed using the Chromeleon 6.8 chromatography software (Dionex).

Analysis of Native and Oxidized Cellooligosaccharides Using HPAEC (E7 and CelS2)

Separation of native and oxidized cellooligosaccharides was achieved using a Dionex Bio-LC equipped with a CarboPack PA1, a column temperature of 30° C. and a flow of 0.25 ml/min, with starting conditions, i.e., 0.1 M NaOH. A stepwise linear gradient with increasing amounts of sodium acetate was applied, going from 0.1 M NaOH and 0.1 M sodium acetate in 10 minutes, then to 0.1 M NaOH and 0.3 M sodium acetate for 25 minutes then increasing to 0.1 M NaOH and 1.0 M sodium acetate at 30 minutes which was kept for 10 minutes. Column reconditioning was achieved by a one minute gradient to initial conditions and subsequent running at initial conditions for 14 minutes. Eluted oligosaccharides were monitored by PAD detection. Chromatograms were recorded and analysed using Chromeleon 7.0 Peak identification was achieved by a procedure including the following steps: oxidized cellooligosaccharides were separated using a Dionex Ultimate 3000 UHPLC system carrying a Hypercarb 150×2.1 mm column (Thermo Scientific) running a gradient of water/0.1% TFA and acetonitrile/0.1% TFA (from 20 to 80% acetonitrile) according to the method developed by Westphal et al., 2010, *Journal of Chromatography A* 1217: 689-695. Eluted peaks were manually fractioned, freeze-dried, re-dissolved in MilliQ water and identified using MALDI-TOF MS. Pure oxidized cellooligosaccharides with known identity were then analyzed using the HPEAC method described above in order to establish the identity of the oxidized cellooligosaccharides generated by CelS2 and E7.

Cellulose Degradation Experiments (E7 and CelS2)

Assays performed to evaluate the function of E7 and CelS2 were set up using a variety of cellulosic substrates (AVICEL®, filter paper and steam exploded wood chips from poplar), at either pH 5.5 (20 mM sodium acetate buffer), 6.5 (20 mM Bis-Tris buffer) or 8.0 (20 mM Tris buffer) in reaction mixtures containing 1.0 mM $MgCl_2$. The effect of the presence of an external electro donor was probed by adding 1.0 mM or 0.5 mM reduced glutathione or ascorbic acid to the reaction mixture (see figure legends for details).

Results

We show here that CBP21, a single-domain protein comprising one CBM33 domain, in fact is an enzyme that catalyzes an oxidohydrolytic cleavage of glycosidic bonds in crystalline chitin, thus opening up the inaccessible polysaccharide material for hydrolysis by normal glycoside hydrolases. This enzymatic activity was first discovered when we detected traces of non-native chito-oligosaccharides upon incubation of beta-chitin nano-whiskers with CBP21 (FIG. 2A). The products were identified as chitin oligosaccharides with a 2-(acetylamino)-2-deoxy-D-gluconic acid (GlcNAcA) at the reducing end (FIGS. 2B, 3A, 3B, 3C, and 3D). We then found that addition of reductants dramatically increased the efficiency of the reaction (FIGS. 4, 6A, and 6B), enabling the destructuring of large crystalline beta-chitin particles by CBP21 alone (FIG. 2C), releasing a range of oxidized products (FIGS. 5A and 5B and below) and boosting chitinase efficiency to much higher levels than previously observed (compare FIG. 1C with FIG. 4).

Figures 5A, 5B:
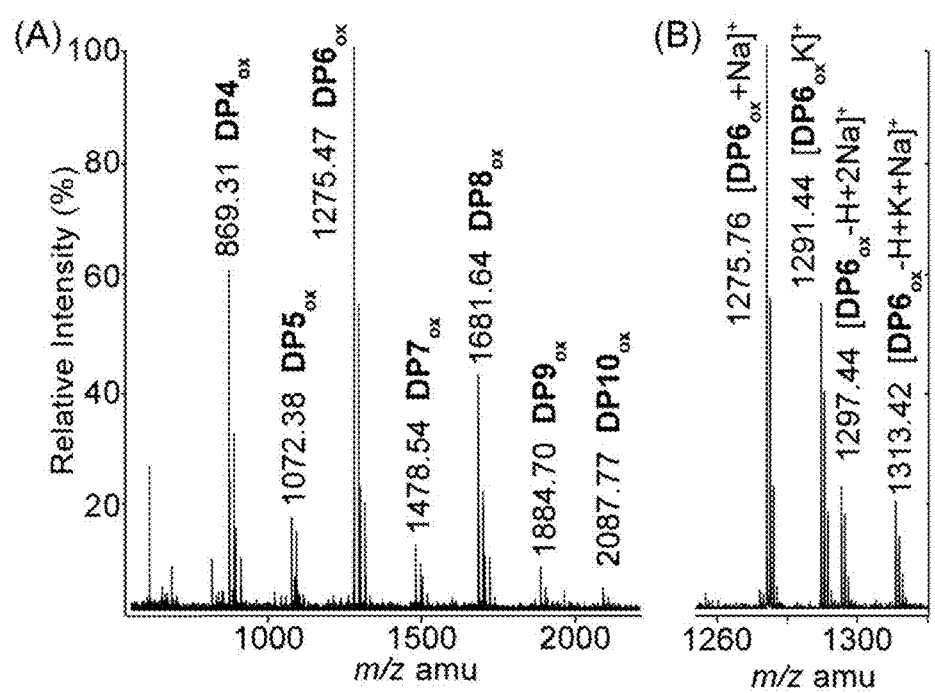
FIGS. 5A and 5B show the analysis of soluble reaction products from CBP21 catalysis.

If CBP21 acted randomly on crystalline surfaces, one would expect generation of longer oligosaccharides, which are difficult to detect due to their low solubility. The majority of soluble products generated by CBP21 in the presence of a reductant had a DP below 10 (FIG. 2A; FIGS. 5A and 5B). To visualize longer products, we exploited a newly cloned chitin deacetylase from *Aspergillus nidulans* (AnCDA) to increase the solubility of longer chitin fragments by deacetylation. This approach indeed revealed the formation of chitin fragments with high DP, either with CBP21 (FIG. 2D) or with an endochitinase (ChiC; FIG. 2E). Both CBP21 and ChiC generated long products, indicative of an "endo-" type of activity.

Two important features stand out. Firstly, when using CBP21 all detected products are oxidized (i.e., they contain a GlcNAcA moiety), confirming the observation that CBP21 catalyzes oxidative hydrolysis of glycosidic bonds. Secondly, whereas the products released by ChiC represent a continuum of lengths, the products released by CBP21 are dominated by even-numbered oligosaccharides (FIGS. 2D, 6A, and 6B). This shows that ChiC tends to cleave any glycosidic bond, whereas CBP21 shows a strong preference for cleaving every second glycosidic bond. Keeping in mind the disaccharide periodicity in the substrate (FIG. 1A), this crucial observation implies that ChiC approaches single polymer chains from "any side", whereas CBP21 must approach the substrate from one fixed side. The latter situation would be obtained if the polysaccharide chain cleaved by CBP21 is part of an intact crystalline structure. Clearly, the endochitinase ChiC and CBP21 have different roles in chitin hydrolysis.

The CBP21 mediated cleavage mechanism was probed in more detail by isotope-labelling. Experiments in $H_2^{18}O$ showed that one of the oxygen atoms introduced at the oxidized new chain end comes from water (FIG. 7A). The only plausible source for the second oxygen was molecular oxygen and this was confirmed by experiments performed in $^{18}O_2$ saturating conditions (FIGS. 7B and 7C). Removal of dissolved molecular oxygen or in the reaction solution inhibited CBP21 activity (FIGS. 8A, 8B, and 8C), confirming the requirement for molecular oxygen for catalysis. The strong inhibition by cyanide, a common mimic of molecular oxygen, supports the crucial role of the oxidative step (FIGS. 8C and 8D). Thus, the reaction catalyzed by CBP21 comprises a hydrolytic step and an oxidation step, as summarized in FIG. 7D. Enzymatic oxidohydrolysis of polysaccharides has so far not been described. CBP21 is referred to herein as a "chitin oxidohydrolase". Likewise, GH61 proteins are referred to as "cellulose oxidohydrolases".

Figure 9:
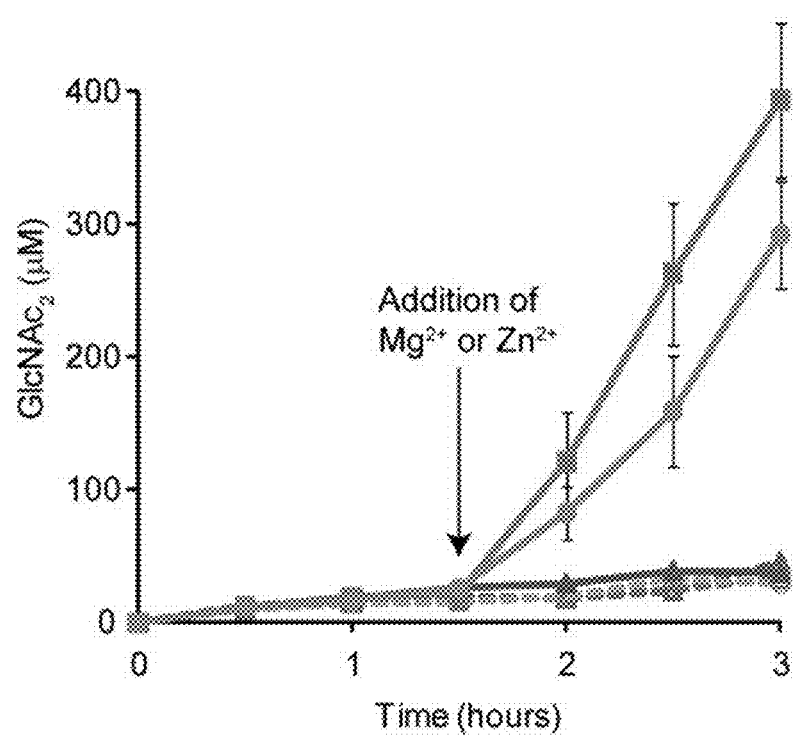
FIG. 9 shows the effect of divalent cations on CBP21 activity. The figure shows ChiC activity, monitored by measuring the concentration of produced $(GlcNAc)_2$ by HPLC. Reaction mixtures contained 2.0 mg/mL beta-chitin in 1.0 mM ascorbic acid, 5 mM EDTA, 0.5 µM ChiC in 20 mM Tris pH 8.0, in the presence or absence of 1.0 µM metal-free CBP21. Solid lines indicate reactions with metal-free CBP21; dashed lines indicate reactions without CBP21. Half way through the reaction (indicated by the arrow) $MgCl_2$ (final concentration 25 mM), $ZnCl_2$ (25 mM) or buffer was added to one of two (parallel) reaction mixtures. Squares, $MgCl_2$ added; circles, $ZnCl_2$ added; triangles, buffer added. The results clearly demonstrate that divalent cations are essential for the function of CBP21; the controls show that the cations do not affect ChiC activity.

CBP21 catalysis was found to be dependent on the presence of a divalent cation (FIG. 9), which may bind to the conserved histidine motif (FIG. 1F). Interestingly, the activity of GH61 proteins also depends on divalent cations (Harris et al., 2010, *Biochemistry* 49: 3305). Structural studies of both CBP21 (Vaaje-Kolstad et al., 2005, *J. Biol. Chem.* 280: 11313) and GH61 proteins (Harris et al., 2010, *Biochemistry* 49: 3305; Karkehabadi et al., 2008, *J. Mol. Biol.* 383: 144) show considerable structural plasticity in the metal-binding site, explaining why the metal binding site is promiscuous and why the need for divalent cations is rather unspecific (as shown in FIG. 9 and in Harris et al., 2010, *Biochemistry* 49: 3305). Mutation of the second histidine (His114 in CBP21 and His89 in GH61E from *Thielavia terrestris*) in the metal binding motif knocked out activity of both proteins (FIGS. 10A and 10B and Harris et al., 2010, *Biochemistry* 49, 3305, respectively). It is conceivable that the metal ion binding aids directly in the binding/stabilization/activation of the reactive oxygen species and/or the hydrolytic water during catalysis. Alternatively, the metal ion may be essential for stabilizing the structure of the active site region of the protein without interacting directly with the oxygen or the water.

Reductants boosted the oxidohydrolytic activity of CBP21 to extreme levels (FIGS. 2C, 4, 6A, 6B, 11A, and 11B), which very well may be beyond what is ever achieved in nature. The reductants are likely to function as electron donor in the oxidative enzymatic process, but the exact flow of electrons from the reductant to molecular oxygen is not yet clear. One option is that electron donation takes place via the generation of reactive oxygen species such as $O_2^-$. Another option is that electrons are somehow channeled to a complex involving CBP21, the substrate and $O_2$, implying that reactive oxygen species such as $O_2^-$ only emerge on the substrate and will not or hardly be present in solution. Most interestingly, and of biotechnological importance, our data show that activity of these new enzymes can be boosted considerably by simply adjusting the reaction conditions.

Figure 4:
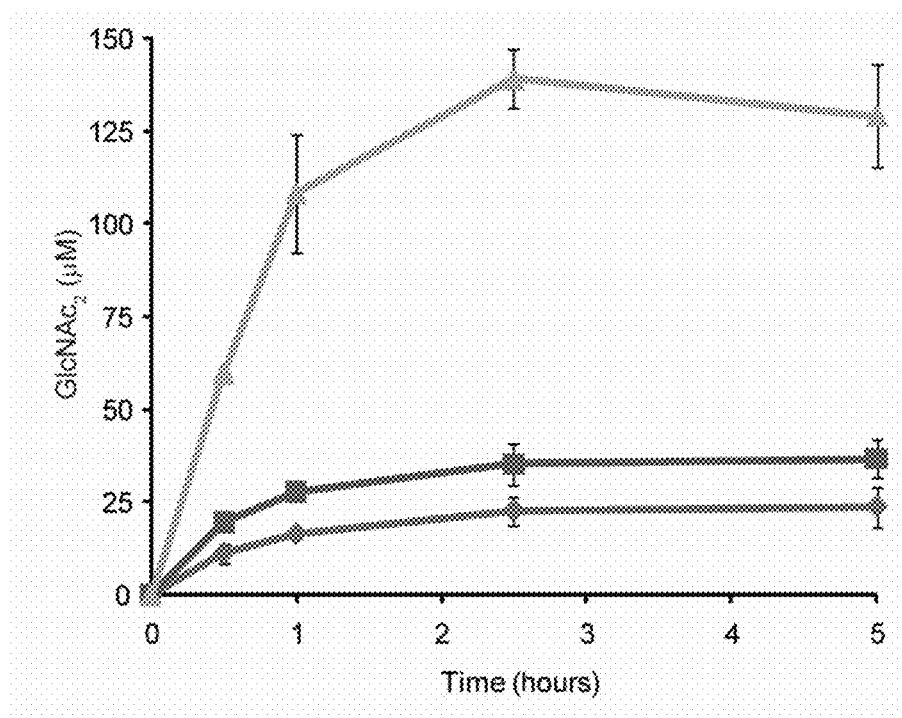
FIG. 4 shows the effect of ascorbic acid (a reductant) on the potentiating effect of CBP21 on chitinase efficiency. The efficiency of beta-chitin (0.1 mg/mL) degradation by 0.5 μM ChiC was analyzed in the presence (top grey line on filled triangles) or absence (bottom grey line on filled diamonds) of 1.0 μM CBP21 and 1.0 mM ascorbic acid at pH 8.0. A parallel reaction containing beta-chitin, ChiC and CBP21 (same concentrations as above) but no ascorbic acid was run as a control (central dark grey line on filled squares). The results show that CBP21 promotes chitin degradation by ChiC considerably better in the presence of ascorbic acid (all chitin is degraded after 2.5 hours), compared to conditions where ascorbic acid is absent. A parallel reaction containing beta-chitin and ChiC (same concentrations as above), in the absence of ascorbic acid, would yield a result similar to that represented by the grey line on filled diamonds (results not shown), but the experiment is included and shown in FIG. 10B), meaning that ascorbic acid alone had no effect on ChiC efficiency.
Figures 10A, 10B:
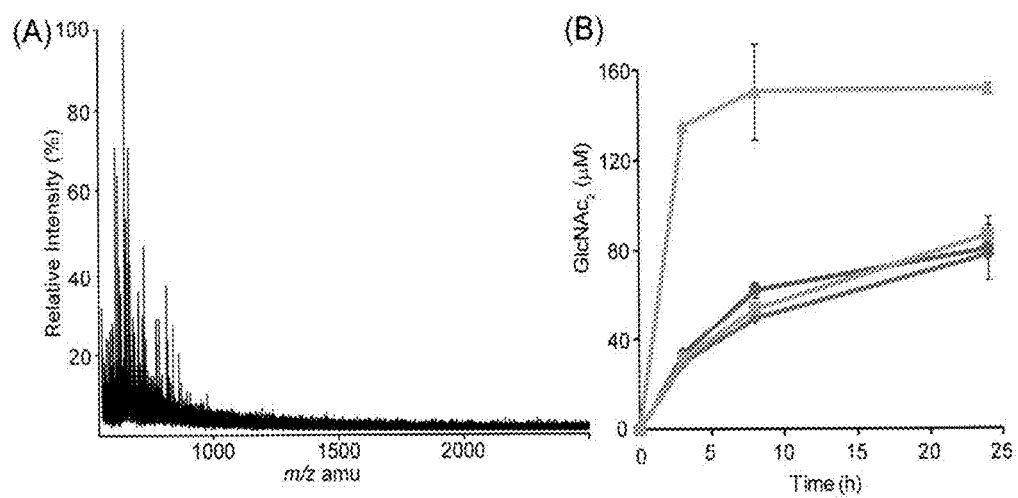
FIGS. 10A and 10B show the importance of the conserved His114. CBP21-like and GH61 proteins contain two highly conserved histidines (H28 and H114 in CBP21), one of which is the N-terminal histidine of the secreted mature protein. In order to probe the importance of His114 the H114A mutant variant of CBP21 was analyzed.
Figure 12:
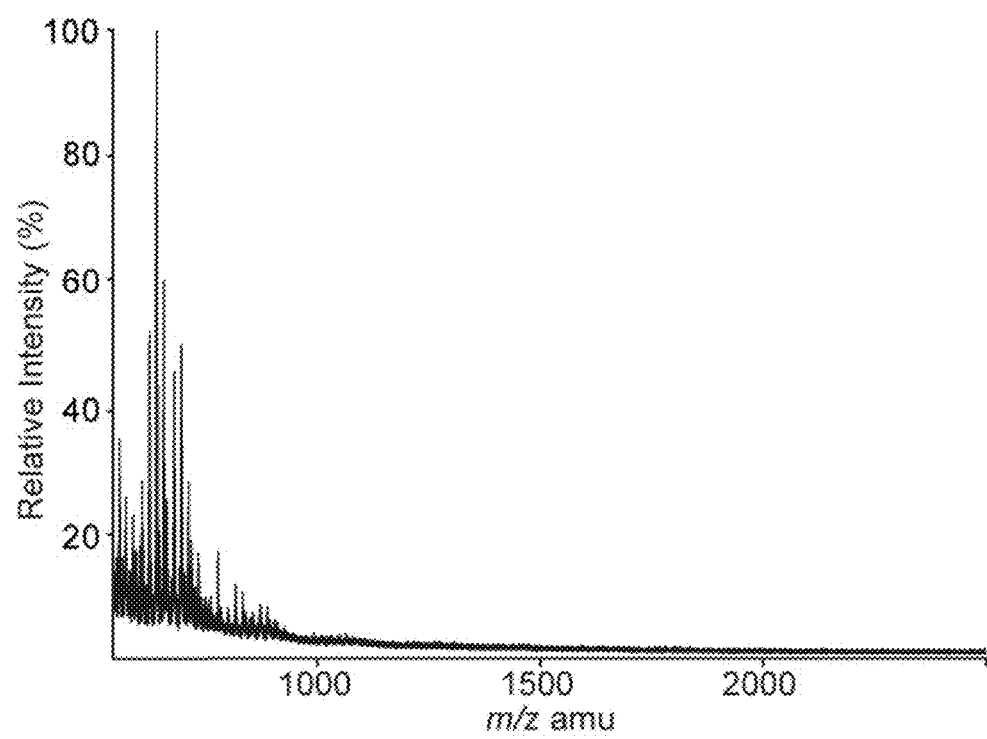
FIG. 12 shows the effect of ascorbic acid on beta-chitin. It is well established that reductants undergo autooxidation in oxygenated solutions, thus generating reactive oxygen species that may putatively oxidize biomolecules present in the surrounding medium. The figure shows MALDI-TOF MS analysis of a reaction mixture obtained after incubating a sample containing 2.0 mg/mL beta-chitin and 1 mM ascorbic acid in 20 mM Tris pH 8.0 for four days at 37° C. The spectrum does not show any sign of soluble oxidized oligosaccharides. 100% relative intensity represents $4.4 \times 10^4$ a.u.
Figure 13:
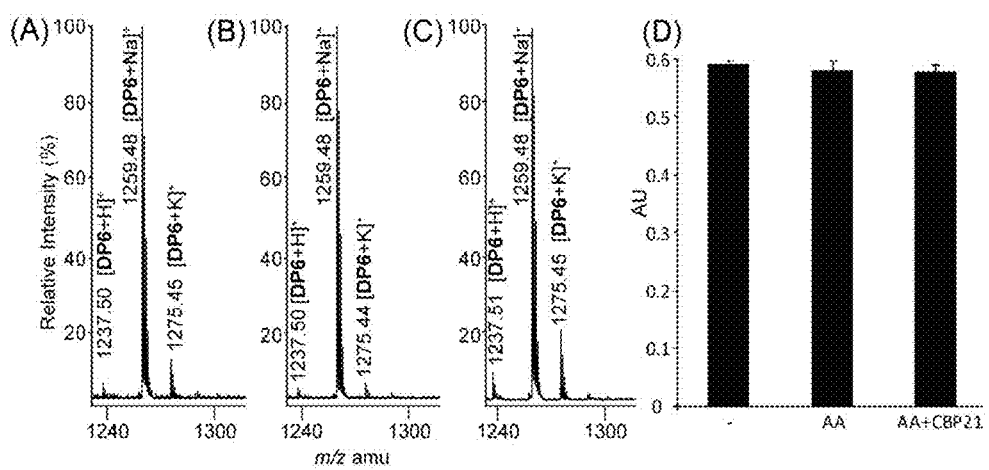
FIGS. 13A, 13B, 13C, and 13D show the effect of CBP21 on soluble native oligosaccharides. Earlier studies (Vaaje-Kolstad et al., 2005, *J. Biol. Chem.* 280: 11313; Suzuki et al., 1998, *Biosci. Biotechnol. Biochem.* 62: 128) have shown that CBP21 binds specifically to beta-chitin and not to soluble or amorphous forms of chitin. With the results presented here in mind, the ability of CBP21 to oxidize and/or hydrolyze native oligosaccharides of chitin was investigated. A solution containing 100 µM GlcNAc$_6$ in 20 mM Tris pH 8.0 was incubated for 16 hours in the presence of buffer only, 1.0 mM ascorbic acid (AA) or 1.0 mM ascorbic acid and 1.0 µM CBP21 and reaction products were analyzed by MALDI-TOF MS (FIGS. 13A, 13B, and 13C, respectively) and quantified by HPLC (FIG. 13D). No degradation or oxidation of GlcNAc$_6$ was observed. Similar experiments were performed with the soluble polymeric chitin-derivative chitosan; again, no degradation or oxidation products could be detected (results not shown). 100% relative intensity represents $5.7 \times 10^3$, $1.4 \times 10^4$ and $4.0 \times 10^4$ a.u. for FIGS. 13A, 13B, and 13C, respectively.
Figure 14:
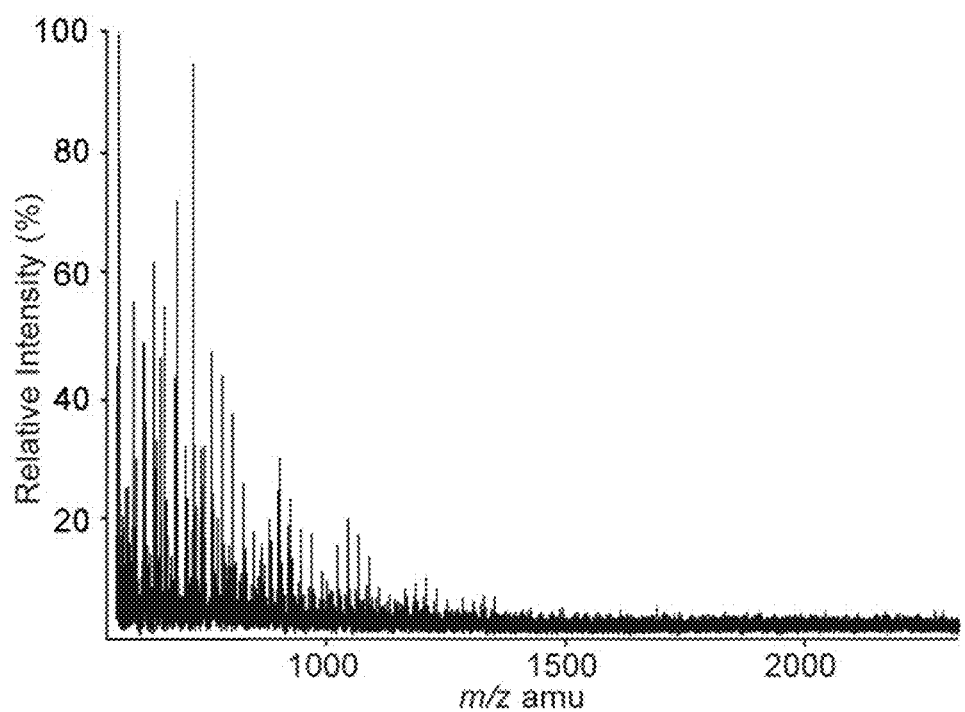
FIG. 14 shows the possible effect of Fenton chemistry on beta-chitin solubilization. It could be envisaged that the observed CBP21 mediated oxidohydrolytic cleavage of beta-chitin is related to generation of conditions leading to Fenton type chemistry (analogous to what has been proposed for cellulose degradation by cellobiose dehydrogenases (Hammel et al., 2002, *Enzyme. Microb. Tech.* 30: 445; Henriksson et al., 2000, *J. Biotechnol.* 78: 93; Hyde & Wood, 1997, *Microbiol-Uk* 143: 259). Although, Fenton chemistry is not particularly effective at the pH used in this study (8.0), we did check whether Fenton-like processes might occur. Fenton chemistry is well known to depolymerize polysaccharides and could yield oxidized products similar to those generated by CBP21. 2.0 mg/mL beta-chitin was incubated for 16 hours with 0.03% $H_2O_2$ and 5.0 mM Fe(II)SO$_4$ in 20 mM Tris pH 8.0, at 37° C. The soluble phase of the reaction was analyzed by MALDI-TOF MS. The mass spectrum shown in the figure did not reveal formation of soluble products. As controls, MALDI-TOF experiments were repeated using various dilutions of the original sample; samples from reactions where the $H_2O_2$ concentration was 0.3% or 0.003% were also analyzed. Soluble products were never observed (results not shown). 100% relative intensity represents $1.2 \times 10^4$ a.u.

We conducted numerous control experiments that all confirmed the conclusion that formation of oxidized products only occurs in the presence of CBP21 and crystalline substrates. The presence of reductants alone did not yield oxidized products (FIG. 12) and did not potentiate or inhibit chitinase action (FIGS. 4 and 10B). When incubated under optimal conditions with hexameric N-acetylglucosamine, neither degradation products nor oxidized oligosaccharides were observed FIGS. 13A, 13B, 13C, and 13D). We also studied the possibility that CBP21 would work without directly interacting with the cleaved bond itself, since one could envisage some sort of CBP21-induced "destructuring" mechanism making the substrate more accessible for the action of reactive oxygen species generated in a CBP21-independent manner, e.g., by Fenton chemistry. We could however not detect any soluble products upon subjecting beta-chitin to Fenton chemistry (FIG. 14). All these experiments confirm that CBP21 actively participates in the oxidohydrolytic cleavage reaction.

Figures 11A, 11B:
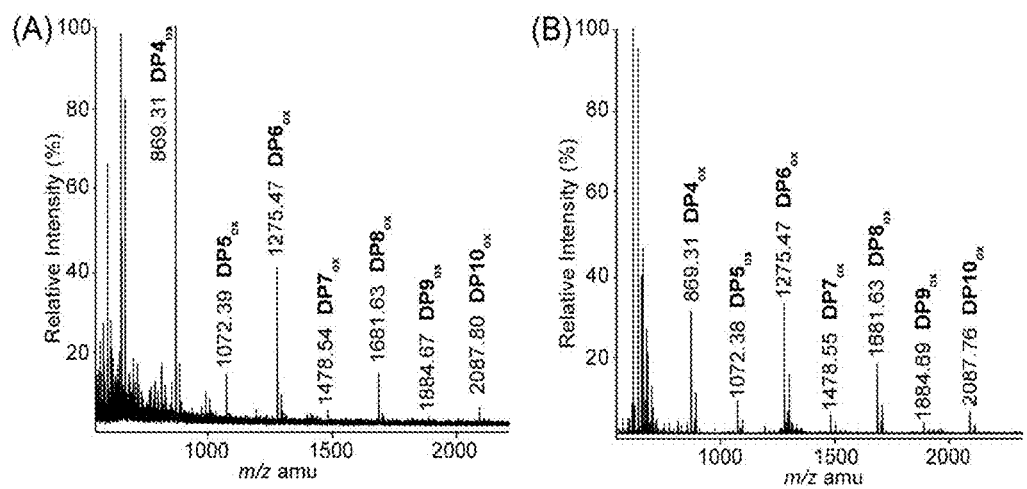
FIGS. 11A and 11B show the effect of other reductants on CBP21 activity. Reaction products obtained upon incubating 2.0 mg/mL beta-chitin for 16 hours at 37° C. in the presence of 1.0 µM CBP21 and (FIG. 11A) 1.0 mM reduced glutathione or (FIG. 11B) in 1.0 mM Fe(II)SO$_4$, in 20 mM Tris pH 8.0. Note that the observed product profiles are highly similar to those obtained in the presence of ascorbic acid (FIGS. 5A and 5B).

As shown in FIGS. 8A, 8B, 8C, and 8D, CBP21 activity is strongly inhibited by cyanide, a known $O_2$ mimic, but not by azide, a known inhibitor of haem proteins. Several reductants capable to function as electron donors boosted the activity of CBP21 (FIGS. 2C, 11A, and 11B). The experimental data indicate that the oxidation step catalyzed by CBP21 is co-factor independent and depends on an external electron donor. Co-factor independent oxygenases have been described before, but these enzymes are normally thought to use conjugated carbanions in the substrates as electron donors (Fetzner and Steiner, 2010, *Appl. Microbiol. Biotechnol.* 86:791), a mechanism that is not likely in the case of a polysaccharide substrate. If the oxidation step was to happen first, this would imply that CBP21 catalyzes co-factor independent oxygenation of a saturated carbon, which is unprecedented and perhaps not very likely. On the other hand, such a mechanism could yield an intermediate product, for example an ester bond, that may be more prone to hydrolysis than the original glycosidic bond. Alternatively, the hydrolytic step could occur first, which would imply that CBP21 is capable of hydrolyzing glycosidic bonds in a crystalline environment using a hitherto unknown mechanism. Such a hydrolytic step would require some degree of substrate distortion (Davies et al., 2003, Mapping the conformational itinerary of beta-glycosidases by X-ray crystallography. *Biochem. Soc. Trans.* 31: 523 and Vocadlo and Davies, 2008, Mechanistic insights into glycosidase chemistry. *Curr. Opin. Chem. Biol.* 12: 539), which seems challenging in a crystalline packing. However, in favour of this mechanism, the subsequent oxidation of the resulting sugar aldehyde ("reducing end") is more straightforward than oxidation of a saturated carbon.

CBP21 introduces chain breaks in what probably are the most inaccessible and rigid parts of crystalline polysaccharides substrates and its mode of action differs fundamentally from the mode of action of glycoside hydrolases. The key difference is that the glycoside hydrolases are designed to host a single "soluble" polysaccharide chain in their catalytic clefts or pockets and that their affinity and proximity to the crystalline substrate tends to be mediated by non-hydrolytic binding domains. In contrast, CBP21 and GH61 enzymes have flat surfaces (FIGS. 1D and 1E) that bind to the flat, solid, well-ordered surfaces of crystalline material and catalyze chain breaks by an oxidohydrolytic mechanism. The chain break will result in disruption of crystalline packing and increased substrate accessibility, an effect that may be augmented by the modification of one of the new chain ends. At the cleavage point one of the new ends is a normal non-reducing end (indicated by R—OH in FIG. 7D). The other new end would have been a new reducing end if the cleavage had been performed by a normal glycoside hydrolase. However, in this case the product is different and the last sugar is oxidized to become 2-(acetylamino)-2-deoxy-D-gluconic acid (FIGS. 2B and 7D; GlcNAcA). This new "acidic chain end" will interfere with normal crystal packing because it will not have the normal chair conformation of the sugar ring and because it carries a charge.

The enzyme activity demonstrated in this study is difficult to discover, because one depends on detecting products with low solubility and potentially a high tendency to remain attached to the crystalline material. In this sense, working with chitin is easier than working with cellulose because product solubilities are slightly higher and because crystalline packing is less compact (Eijsink et al., 2008, Trends Biotechnol. 26: 228). The experiment with the chitin deacetylase (FIGS. 2D and 2E) provided essential insights, but this approach can simply not be used for cellulose. Looking for chain-breaking activities of GH61 proteins with commonly used reducing end assays obviously will not work due to the oxidative mechanism.

Figures 16A, 16B:
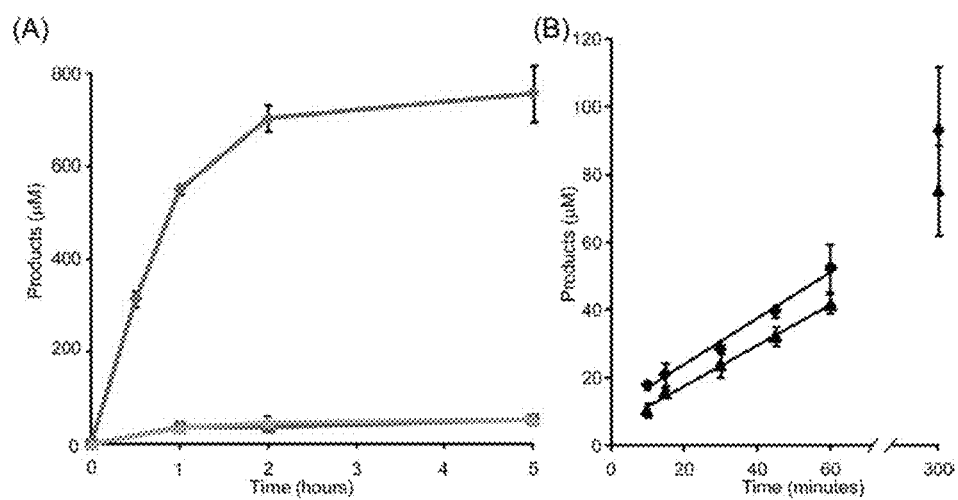
FIGS. 16A and 16B show the speed and extent of oxidative cleavage by CBP21 activity.

Using methods for quantification of oxidized products, we were able to estimate the speed and degree of oxidation under various conditions (FIGS. 16A and 16B). When CBP21 acts alone on beta-chitin under optimal conditions the oxidation rate is in the order of 1 per minute and the maximum extent of oxidation is about 7.6% of the sugars. Simultaneous degradation of beta-chitin with CBP21 and ChiC under optimal conditions led to oxidation of approximately 4.9% of the sugars. It must be noted that in nature enzymes such as CBP21 normally act simultaneously with at least one, and in the case of S. marcescens, three chitinases (Suzuki et al., 1998, Biosci. Biotechnol. Biochem. 62: 128).

Figure 15E:
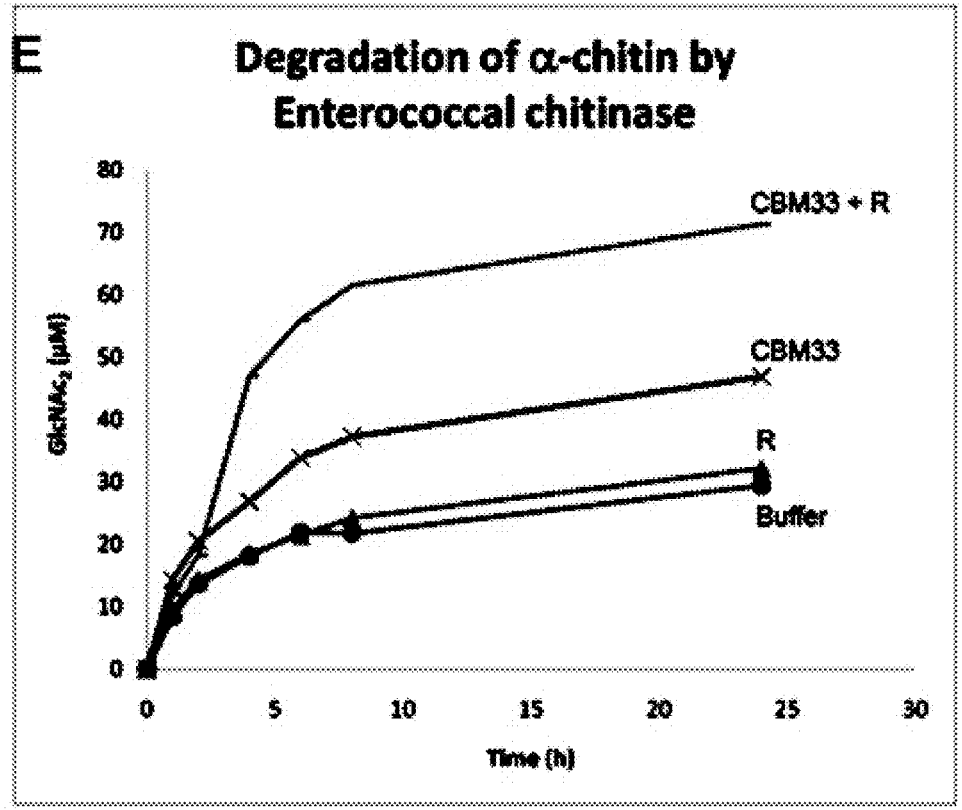
FIG. 15E shows n degradation of 2.0 mg/ml alpha-chitin (from shrimp shells) by 0.3 µM of the chitinase from *Enterococcus feacalis* (protein name (EF0361) in the presence or absence of 0.3 µM EfCBM33 and 1.0 mM reductant (R: reduced glutathione) incubated at 37° C. with agitation at 900 rpm. A boost of the chitinase activity is clearly observed in the presence of EfCBM33 and reductant.

The experiments conducted on CBM33 family protein EfCBM33 revealed that this protein is functionally similar to CBP21. The results of the MS analysis, depicted in FIG. 15D resemble those obtained with CBP21, clearly showing the formation of oxidized products and the oxidohydrolytic properties of this protein. It is interesting to note that EfCBM33 not only works on beta-chitin (FIG. 15D but also on alpha-chitin (FIG. 15E).

The efficacy of CBM33 proteins on cellulose as the substrate were examined. Mature wild type E7, CelS2 and a cellulase classified as a belonging to GH family 7 and originating from Trichoderma reesei called Cel7A (Harjunpaa et al., 1999, FEBS Letters 443: 149-153) were purified to ~95% purity using the cloning, expression and purification strategies described in the Material & Methods section. Finally, a cellulase mixture called CELLUCLAST™, which is an easily available and well known commercial product from Novozymes, was used.

To determine whether CelS2 and/or E7 had the ability to release soluble sugars from crystalline cellulose, CelS2 or E7 was incubated with AVICEL® in the presence or absence of an external electron donor (reduced glutathione or ascorbic acid). Putative reaction products were analyzed using MALDI-TOF MS for qualitative detection of product types and HPAEC (high pressure anion exchange chromatography), a chromatographic method enabling product identification and, in principle, quantification. Indeed, soluble oligomeric products were observed with both proteins (only shown for CelS2; FIGS. 17-19) and with both detection methods. Native cellooligosaccharides were observed in both conditions with and without external electron donor, but in substantial larger amounts in the former condition. Oxidized cellooligosaccharides were only observed in experiments where an external electron donor was present.

More specifically, MALDI-TOF MS analysis revealed the presence of cellooligosaccharides with an oxidized reducing end (i.e., cellooligosaccharides with the reducing glucose moiety replaced with a gluconic acid moiety; FIGS. 17 and 18). The degree of polymerization (DP) of the released soluble oxidized oligosaccharides visible in FIG. 17 ranged from DP4 to DP7 and the product signals showed alternating intensity/quantity depending on the cellooligosaccharide being even or odd numbered in terms of DP (even numbered cellooligosaccharides dominated). HPAEC analysis of the same samples reflected the results provided by the MALDI-TOF MS analysis, showing the presence of peaks with alternating intensities representing oxidized cellooligosaccharides (FIG. 19).

The dominance of even numbered oligosaccharides is a logical consequence of the fact that CBM33 enzymes attack the polysaccharide chains in their crystalline environment. As the repeating unit of cellulose and chitin is a dimer, only every second sugar/glycosidic bond on the crystalline polysaccharide chain is prone for cleavage by the CBM33 enzyme, meaning that released products would tend to have an even-numbered DP. (NB. acid hydrolysis of either crystalline cellulose or chitin gives an even distribution of even and odd numbered oligosaccharides).

FIG. 19 shows that incubation with CelS2 in the presence of a reducing agent, leads to cleavage of the cellulose chains in the crystal in an oxidohydrolytic manner, releasing soluble oxidized cellooligosaccharides (light grey, upper line). This also leads to additional release of non-oxidized cellooligosaccharides, which is likely to result in part from the disruption the AVICEL® crystal surface that facilitates the release of shorter oligomers that are captured in the crystal. Additionally, chain cleavage by CelS2 near the reducing end of a cellulose chain will give rise to such products.

Reactions containing crystalline cellulose (filter paper) and cellulases (either a cellulase mixture called CELLUCLAST™, or a single component cellulase, Cel7A) were monitored for cellobiose and glucose release in the presence and absence of CelS2/E7 and/or an external electron donor.

When CELLUCLAST™ was incubated with filter paper in the presence of CelS2 or E7, the glucose yield was indeed higher than when the filter paper was incubated with only CELLUCLAST™ (FIG. 20; ~3.0 fold increase for CelS2 and E7 after 24 hours incubation and ~9 fold increase for CelS2 and ~3.5 fold increase for E7 after 120 hours incubation). When both CelS2 and an external electron donor were added, the glucose yields were even higher (FIG. 20; ~5 fold increase for CelS2 and 3.5-fold increase for E7 after 24 hours incubation and ~11 fold increase for CelS2 and ~4.5 fold increase for E7 after 120 hours incubation), indicating that the presence of an external electron donor indeed is of importance for the boosting effect of CelS2 and E7.

Since the CELLUCLAST™ product contains a complex mixture of hydrolytic activities that may complicate the interpretation of the results, a monocomponent cellulase (Cel7A) was purified from CELLUCLAST™ (Novozymes) and used to probe the boosting efficiency of CelS2. Effects similar to those observed when combining CELLUCLAST™ and CelS2 in the presence and absence of an external electron donor were also observed when incubating Cel7A with CelS2 (FIG. 21). In the absence of an external electron donor, CelS2 improved Cel7A activity (in terms of cellobiose yield) 5.5- and 7.3-fold after 18 and 40 hours incubation, respectively. In the presence of an external electron donor, CelS2 improved Cel7A activity 6.7- and 9.8-fold after 18 and 40 hours incubation, respectively.

FIGS. 20 and 21 show that in addition to boosting cellulose activity the presence of CelS2 in both cases also aids in maintaining the cellulase activity over time. Whereas the activity of the cellulases incubated in the presence or absence of an external electron donor comes to an almost complete stop within the first 18-24 hours, cellulase activity continues in the samples incubated with CelS2. This effect may be a partial explanation for the synergistic effects that CBM33 proteins have on the degradation of chitin or cellulose by hydrolytic enzymes (chitinase and cellulases, respectively).

The oxidized products generated by CelS2 in the presence of an external electron donor exists in an equilibrium of two forms, the glucono delta-lactone which gains in population at mildly acidic pH and the gluconic acid form that dominates at mildly alkaline pH. At mildly alkaline pH (e.g., pH 8.0) it is likely that the charge developing on the cellulose crystal surface due to CelS2 activity may aid the distortion and disruption/solubilization of the cellulose crystal and thus increase the accessibility of the substrate for the cellulases. However, it is conceivable that oxidized oligosaccharides and or oxidized chain ends in cellulose crystals may also inhibit certain cellulases (e.g., exo-acting enzymes), making it likely that the degree of CelS2/CBM33 activity should be carefully adjusted for optimal boosting efficiency.

When probing the cellulose boosting properties of CelS2 at various pHs using monocomponent Cel7A as the cellulose hydrolytic component, pH 5.5 came out as the optimal pH for activity. Less activity was seen at pH 6.5 and no activity could be detected at pH 8.0 (data not shown). The most obvious reason for the decrease in cellulose hydrolysis at increasing pH is the pH stability and efficiency of Cel7A. The cellulase is close to inactive at pH 8.0, which is a common trait for fungal cellulases in general (Garg & Neelakantan, 1981, *Biotechnology and Bioengineering* 23: 1653-1659 and Wood, 1985, *Biochemical Society Transactions* 13: 407-410.). CelS2 is a bacterial enzyme that originates from *Streptomyces* species that are known to grow optimally on cellulosic substrates in approximately neutral pH conditions (Kontro et al., 2005, *Letters in Applied Microbiology* 41: 32-38.). The data presented in FIG. 19 show that CelS2 is active at pH 8.0.

Because of the pH-dependent properties of the cellulases, the synergy experiments reported here were performed at slightly acidic pH, which may be suboptimal for the particular CBM33 used (primarily CelS2 from *Streptomyces*). It is thus possible that the observed effects of CelS2 are smaller than they could be under conditions optimized for CelS2 activity.

More generally, an expert in the field will know that natural enzymes vary in terms of their optimum pH and temperatures for activity. The expert will know that this will also apply to hydrolytic enzymes, such as cellulases and chitinases and to oxidohydrolytic enzymes, such as CBP21 and CelS2. It is obvious that for obtaining optimal overall reaction efficiency and/or for maximizing the boosting effect of a CBM33, one needs to take into account the pH optima and temperature optima of both the CBM33 and the hydrolytic enzymes. One may obtain enzymes with varying pH and temperature optima by selecting appropriate enzymes from nature or by modification of properties such as pH optimum of natural enzymes using protein engineering type of technologies.

It is conceivable that pH affects the performance of a CBM33+hydrolase(s) type of enzymatic system because pH affects the equilibrium between lactone and the acid form of the oxidized products, which again may affect the efficiency of the hydrolytic enzymes. The pH may also affect the reductant.

These experiments show that some family 33 CBMs, like CelS2 and E7, are active on crystalline cellulose, boost cellulase activity in both the absence and presence of an external electron donor, but show substantially higher activity/boosting effect with the electron donor present. These observations, as well as the results previously obtained for CBP21 acting on chitin, indicate that the oxidation of one of the newly generated chain ends is important for the function of these CBM33 enzymes. That the oxidation indeed also is part of the mechanism for CBM33s that act on cellulose is further supported by data showing that cyanide, a well known oxygen mimic, inhibits the generation of oxidized cellooligosaccharides when CelS2 is incubated with AVICEL® in the presence of an external electron donor (FIG. 22).

Additionally, a variant of CelS2 was generated containing a mutation of a putatively essential conserved residue, histidine 144, to alanine. This histidine is one of the strongly conserved residues in the metal binding motif characteristic for family 33 CBMs and corresponds to His114 in CBP21 (FIGS. 1D and 1F; FIGS. 10A and 10B; Vaaje-Kolstad et al., 2010, *Science* 330: 219-222). FIGS. 23A and 23B show that CelS2-H144A was unable to generate oxidized cellooligosaccharides in the presence of an external electron donor.

It is important to emphasize once more that experiments have been performed at only one pH, which is likely to be not optimal for one of the two enzyme components (CBM33 or hydrolytic enzyme), as discussed above. The cellulases used work optimally at the acidic range of the pH scale, while the cellulose oxidating CBM33s are more active at the basic range of the pH scale. An expert in the field will understand that one may get different and better results when adapting the pH of the reaction and/or by selecting enzyme variants that are better suited for the pH used here and to work together at this particular pH. The full potential of the oxidative boosting effect may thus not be seen in these experiments.

Finally, other cellulosic variants (filter paper and steam exploded sawdust from poplar) were also probed as substrates for CelS2. Soluble oxidized cellooligosaccharides were not observed by MALDI-TOF MS analysis (results not shown). This is most likely due to the high DP of the cellulose in these substrates; cleavages on the crystalline surfaces will not easily lead to release of soluble (=short) cellooligosaccharides when the overall DP is very high. AVICEL® is special in that it is a form of microcrystalline cellulose that has a very low DP (~60-100; Wallis et al., 1992, *Carbohydrate Polymers* 17: 103-110 and Mormann and U, 2002, *Carbohydrate Polymers* 50: 349-353) compared to that of the other substrates tested.

However, when the cellulase boosting effect of the CBM33s, in this case CelS2, was probed with a more "natural" substrate (represented by steam exploded sawdust from poplar), the effect of CelS2 was indeed present as shown by a ~2-fold increase; FIG. 24). The data shown for the boosted CELLUCLAST™ effect on steam exploded sawdust from poplar, which represents a substrate more like what is used in industrial biomass degrading applications, also show that CelS2 activity does not dependent on the substrate being of high purity. Clearly, CelS2 also acts on cellulose present in a more natural environment (i.e., embedded in a plant/wood cell wall matrix).

Apart from showing a completely novel enzyme activity for modifying solid polysaccharide surfaces, our results point into new directions for enzymatic conversion of recalcitrant polysaccharides. Clearly, CBM33 family proteins (such as CBP21, EfCBM33 (FIGS. 15A, 15B, 15C, 15D, and 15E), E7 and CelS2 (FIGS. 17-22, 23A, 23B, and 24)) and GH61 family proteins (such as the GH61 proteins found in *T. terrestris, Phanerochaete chrysosporium* or *Hypocrea jecorina*) can dramatically increase the efficiency of hydrolytic enzyme mixtures for chitin and cellulose and a first glimpse of the potential of GH61 proteins for cellulose conversion has indeed been presented very recently (Harris et al., 2010, *Biochemistry* 49: 3305). The present invention shows how the beneficial effects of CBM33 and GH61 family proteins may be boosted by adjusting the reaction conditions, i.e., the combined presence of an appropriate metal ion and agents that are reducing and/or generate reactive oxygen species. Clearly, the dependency of these oxidohydrolases on the presence of molecular oxygen and reductants acting as external electron donors provides guidelines for process design.

Example 2: Effects of CelS2 on Cellulose Degradation by Cellulases, in the Presence of Reduced Glutathione FIGS. 20 and 21 show that one of the effects of CelS2 and E7 is to prolong cellulase activity. While reactions with CELLUCLAST™ alone or Cel7A alone hardly produce any additional soluble glucose after the first time point (24 hours in FIG. 20, 18 hours in FIG. 21), release of soluble glucose continues in most cases where a CBM33 protein is present and this effect is increased in the presence of a reductant. To further analyze this, we conducted a time course experiment to examine the effect of CelS2 on CELLUCLAST™ activity over time.

Materials and Methods

As in Example 1. Further experimental details, including minor deviations from the standard protocols described in Example 1 are provided in the figure legends, where necessary, for this Example and the Examples which follow.

Results

The results (FIG. 25) clearly show that the production of soluble glucose by CELLUCLAST™ levels off, while production of soluble glucose continues if CelS2 is present. This effect is increased if a reducing agent is also present. It is conceivable that CelS2 somehow prevents the cellulases from becoming irreversibly and non-productively bound to the substrate by modifying the surface of the cellulosic substrate, a phenomenon that is generally considered to reduce cellulase efficiency (Jalak and Väljamäe, 2010, *Biotechnology and Bioengineering* 106:871-883).

Example 3: Effects of CelS2 and Cel7A on Cellulose Degradation by Cellulases in the Presence of Reduced Glutathione To examine the functionality of CelS2, including its effect on prolonging cellulase activity, in more detail, the effect of CelS2 on the efficiency of a monocomponent cellulase was studied. The monocomponent enzyme was HjCel7A, obtained by purification from a mixture of cellulases from *Hypocrea jecorina* (*Trichoderma reesei*).

Materials and Methods

As in Example 1.

Results

The results, depicted in FIG. 26 clearly show that CelS2 boosts the activity of the cellulase, Cel7A, and that this boosting effect is larger in the presence of a reductant. The results also show that the presence of CelS2 prolongs the activity of Cel7A.

Example 4: Effects of Different Reductants on CBM33 Efficiency—Studies with Recombinantly Produced N-Terminal CBM33 Domain of CelS2

To check for the functionality of different reductants the recombinantly produced N-terminal CBM33 domain of CelS2 was incubated with 0.8 mM of reduced glutathione, gallic acid or ascorbic acid and the release of oxidized oligosaccharides from AVICEL® was monitored, Materials and Methods As in Example 1.

Results

FIG. 27 shows that all of the tested reductants boosted the activity of the CBM33 protein, although to a different extent. The choice of optimal reductant will, among other things, depend on pH, the substrate and the type of GH61/CBM33 protein.

Example 5: Effects of Reductant on the Boosting Effect of E7 on Cellulase Activity According to the Pfam bioinformatic analysis (pfam.org), E7 is a single domain CBM33 protein (Uniprot ID: Q47QG3; E7) whereas CelS2 (Uniprot ID: Q9RJY2) comprises a CBM33 domain with a CBM2 (Carbohydrate-Binding Module 2; see cazy.org) attached on the C-terminal side of the protein. It is important to note that single domain proteins such as E7 are active by themselves, as illustrated in FIG. 20. To further illustrate this, FIG. 28 was prepared which shows the degradation of cellulose by CELLUCLAST™ or a combination of CELLUCLAST™ and E7 in the presence or absence of reductant.

Materials and Methods

As in Example 1.

Results

It is clearly seen in FIG. 28 that E7 acts in synergy with CELLUCLAST™, and that the presence of reductants has a boosting effect on E7. Note also that FIG. 28 shows that one of the effects of E7 is that it prolongs cellulase activity over time, similar to what was observed for CelS2, as described above. FIG. 29 shows a MALDI spectrum of the oxidized products produced by E7 upon incubation with AVICEL® and a reductant.

Example 6: Effects of Additional CBMs (the N-Terminal CBM33 Domain of CelS2 and the C-Terminal CBM2 Domain of CelS2)

As noted in Example 6, E7 is a single domain CBM33 protein, whereas CelS2 comprises a CBM33 domain with a CBM2 attached on the C-terminal side of the protein. It is important to note that single domain proteins such as E7 are active by themselves, as illustrated in FIG. 28. To further illustrate this, FIG. 30 was prepared which shows the products released from cellulose by full length CelS2, the recombinantly expressed N-terminal CBM33 domain of CelS2, and the recombinantly expressed C-terminal CBM2 domain of CelS2.

Materials and Methods

As in Example 1. The sequence of the recombinantly produced N-terminal CBM33 domain is:

(SEQ ID NO: 22)
HGVAMMPGSRTYLCQLDAKTGTGALDPTNPACQAALDQSGATALYNWF

AVLDSNAGGRGAGYVPDGTLCSAGDRSPYDFSAYNAARSDWPRTHLTS

-continued

```
GATIPVEYSNWAAHPGDFRVYLTKPGWSPTSELGWDDLELIQTVTNPP

QQGSPGTDGGHYYWDLALPSGRSGDALIFMQWVRSDSQENFFSCSDVV

FDGG.
```

Results

As expected the CBM2 domain alone did not show any activity on cellulose (FIG. 30). However, the CBM33 domain shows activity on AVICEL® without its CBM2, although lower than the activity of the whole protein.

These data clearly show that CBM33 domains alone can act synergistically with cellulases and that the activity of these single domains is stimulated by the presence of reductants (see also FIG. 27). The data also show that the presence of additional CBM domains, such as the CBM2 in CelS2, may be beneficial for CBM33 activity. By analogy to what is known in the scientific literature about the effects of adding various types of CBMs to various types of carbohydrate-active enzymes, it will be understood that the activity and efficiencies of naturally occurring CBM33 and GH61 proteins may be manipulated by removing, adding or changing additional CBMs that are fused to the CBM33 or GH61 domain.

Example 7: Metal Activation of CelS2

To identify which is the preferred metal for CelS2, the activity of the N-terminal CBM33 domain of CelS2 was inhibited by EDTA and different metals were tested to reactivate the protein.

Materials and Methods

As in Example 1.

Results

FIG. 31 clearly shows that under the conditions used in this experiment, including very low metal concentrations (compared to, e.g., the concentrations used in FIG. 9) only copper of the tested metals was able to reactivate CelS2 (10 µM metal concentration in the presence of 20 µM EDTA). Thus, copper ions may be the preferred metal ion for CelS2. It should be noted though that at slightly higher (but still low) concentrations, many other metal ions will also work, at least for practical purposes (Vaaje-Kolstad et al., 2010, supra; Harris et al., 2010, supra; FIG. 9).

Exactly which metal ion is employed by CBM33s and GH61s remains somewhat uncertain, but for practical purposes, several metal ions will work at low (1 mM range) concentrations. If CBM33s and GH61 prefer copper, the fact that other bivalent metal ions have been observed to activate both CBM33 and GH61 enzymes (e.g., FIG. 9 and Harris et al., 2010, supra) may be due to the following: $Cu^{2+}$ ions naturally present in very low amounts in the reaction mixtures (e.g., as part of the substrate) may be inaccessible to the enzyme because they are bound to, e.g., the substrate. By adding other bivalent metal ions that tend to bind to the same "binding sites", bound copper ions may be released and thus become available for the enzymes (they are "outcompeted" from the binding sites by the added bivalent metals). At concentrations in the 1 mM range, that work well for other metals, $Cu^{2+}$ inhibits CBM33 action which may be due to unspecific binding (not shown).

Example 9: Sequence and Activity Comparisons

GH61 enzymes that are known to be active on cellulose (TtGh61E, Harris et al., 2010, supra) or that are likely to be active on cellulose by analogy, such as the two GH61 proteins encoded on the genome of *Hypocrea jecorina* (or *Trichoderma reesei*; HjGH61A & HjGH61B) share several conserved residues in addition to the two histidines making up the metal binding site (FIGS. 32A and 32B). Interestingly, these same residues are conserved in cellulose-active E7, whereas several of them are absent in the chitin-active CBP21 (FIGS. 33A, 33B, and 33C).

Example 10: Cleavage of Cellulose by GH61 Proteins in the Presence of Reductants GH61 proteins TtGH61E (SEQ ID NO: 1) and TaGH61A (SEQ ID NO: 2) were incubated with cellulose and ascorbic acid to demonstrate that these proteins can cleave cellulose and yield oxidized products in the presence of ascorbic acid. The two proteins were cloned and produced as described in Harris et al., 2010, supra. FIG. 34 clearly shows that TtGH61E cuts cellulose producing oxidized and native celluoligosaccharides in a similar way as CBM33 proteins. While the product pattern is similar to that obtained with CBM33s, it is not identical. The patterns typically obtained with CBM33s acting on cellulose in the presence of reductants (FIGS. 19, 22, 27, 30, and 31) show different peridiodicities (i.e., relative abundances of the various products, both oxidized and native oligosaccharides). This may indicate that TtGH61E acts on the substrate in a slightly different way, e.g., by attacking another face of the crystal. Clearly, however, the overall outcome of the reaction of TtGH61E in the presence of the reductant is similar to the outcome of reactions of CBM33s on cellulose in the presence of reductant. FIG. 34 also shows that TaGH61A is much less active than TtGH61E, at least on this substrate, the production of oxidized sugars being very low. Notably, this enzyme produces relatively more native cello-oligosaccharides, i.e., a product pattern that is clearly different from the product patterns obtained with TtGH61E and the CBM33s, which again may indicate slight variations in substrate binding specificity.

Example 11: Effect of Reductants on Cellic™ CTec2, a Cellulase Preparation Containing GH61

Since the commercially available cellulase preparation Cellic™ CTec2 contains GH61 proteins, the effect of ascorbic acid on the efficiency of this enzyme preparation was tested. In this experiment the effect of ascorbic acid on glucose release from cellulose by Cellic™ CTec2 was investigated. FIG. 35 shows that the presence of ascorbic acid increased the release of glucose from both Filter Paper and AVICEL® by about 30%, demonstrating the beneficial effects of ascorbic acid.

What is claimed is:

1. A process for producing a fermentation product, comprising:
   (a) degrading or hydrolyzing a cellulosic material with an enzyme composition comprising a GH61 protein and one or more enzymes selected from the group consisting of a cellulase, a hemicellulase, an esterase, an expansin, a laccase, a ligninolytic enzyme, a pectinase, a peroxidase, a protease, and a swollenin, wherein the degrading or hydrolyzing is carried out in the presence of at least one reducing agent and at least one divalent metal ion, wherein the at least one reducing agent is selected from the group consisting of ascorbic acid, coumaric acid, ferulic acid, gallic acid, glucose, glucosamine, N-acetylglucosamine, reduced glutathione, humic acid, succinic acid, and lignin or fragments thereof, wherein the at least one divalent metal ion is selected from the group consisting of $Ca^{2+}$, $Co^{2+}$, $Cu^{2+}$, $Mg^{2+}$, $Mn^{2+}$, $Ni^{2+}$, and $Zn^{2+}$, and wherein the degrading or hydrolyzing of the cellulosic material is increased by the presence of the GH61 protein in combination with the at least one reducing agent and the at least one divalent metal ion relative to without the combination;
   (b) fermenting the degraded cellulosic material with one or more fermenting microorganisms to produce the fermentation product; and
   (c) recovering the fermentation product from the fermentation.

2. The process of claim 1, wherein the cellulosic material is pretreated.

3. The process of claim 1, wherein the cellulase is one or more enzymes selected from the group consisting of an endoglucanase, a cellobiohydrolase, and a beta-glucosidase.

4. The process of claim 1, wherein the hemicellulase is one or more enzymes selected from the group consisting of a xylanase, an acetylxylan esterase, a feruloyl esterase, an arabinofuranosidase, a xylosidase, and a glucuronidase.

5. The process of claim 1, wherein steps (a) and (b) are performed simultaneously in a simultaneous saccharification and fermentation.

6. The process of claim 1, wherein the fermentation product is an alcohol, an alkane, a cycloalkane, an alkene, an amino acid, a gas, isoprene, a ketone, an organic acid, or polyketide.

7. The process of claim 1, wherein said reducing agent is ascorbic acid.

8. The process of claim 1, wherein said divalent metal ion is $Cu^{2+}$.

9. The process of claim 1, wherein the GH61 protein comprises the amino acid sequence of SEQ ID NO: 1, 2, 3, 15, or 16, or a sequence with at least 90% sequence identity thereto.

10. The process of claim 1, wherein the GH61 protein comprises the amino acid sequence of SEQ ID NO: 1, 2, 3, 15, or 16.

* * * * *